US009624278B2

(12) United States Patent
Mechali et al.

(10) Patent No.: US 9,624,278 B2
(45) Date of Patent: Apr. 18, 2017

(54) PROTEIN COMPLEX COMPRISING MCM8 AND MCM9 PROTEINS AND THEIR USE

(75) Inventors: Marcel Mechali, Montferrier sur Lez (FR); Malik Lutzmann, Montpellier (FR); Sabine Traver, Montpellier (FR); Bernard De Massy, Montpellier (FR); Corinne Grey, Montpellier (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 423 days.

(21) Appl. No.: 14/240,959

(22) PCT Filed: Aug. 30, 2012

(86) PCT No.: PCT/EP2012/066904
§ 371 (c)(1),
(2), (4) Date: Apr. 23, 2014

(87) PCT Pub. No.: WO2013/030302
PCT Pub. Date: Mar. 7, 2013

(65) Prior Publication Data
US 2014/0227280 A1 Aug. 14, 2014

(30) Foreign Application Priority Data

Aug. 30, 2011 (EP) .................... 11306082

(51) Int. Cl.
*C07K 14/47* (2006.01)
*A61K 38/17* (2006.01)
*C12N 9/12* (2006.01)
*C07K 16/18* (2006.01)

(52) U.S. Cl.
CPC .......... *C07K 14/47* (2013.01); *A61K 38/1709* (2013.01); *C07K 14/4738* (2013.01); *C07K 16/18* (2013.01); *C12N 9/1252* (2013.01); *C07K 2319/00* (2013.01)

(58) Field of Classification Search
None
See application file for complete search history.

(56) References Cited

FOREIGN PATENT DOCUMENTS

WO 2006/084694 A2 8/2006
WO 2006/120019 A2 11/2006

OTHER PUBLICATIONS

Klug et al., Concepts of Genetics, 4th edition, 1994, Prentice Hall, pp. 30-36.*
Curcio et al., J Biol Chem. Dec. 5, 1986;261(34):16126-32.*
Donovan, S., et al.: "Cdc6p-dependent loading of Mcm proteins onto pre-replicative chromatin in budding yeast" (1997) Proc Natl Acad Sci USA 94,5611-5616.

Maiorano, et al.; "Stepwise Regulated Chromatin Assembly of MCM2-7 Proteins", The Journal of Biological Chemistry by the American Society for Biochemistry and Molecular Biology, Inc. vol. 275, No. 12, Issue of Mar. 24, pp. 8426-8431, 2000.
Liu, Y., et al.: "Ancient diversification of eukaryotic MCM DNA replication proteins" (2009). BMC Evolutionary Biology 2009, 9:60, Received: Sep. 29, 2008, Published: Mar. 17, 2009.
Maiorano, D., et al.: "MCM8 Is an MCM2-7-Related Protein that Functions as a DNA Helicase during Replication Elongation and Not Initiation" Cell, vol. 120, 315-328, Feb. 11, 2005, Copyright © 2005 by Elsevier Inc.
Lutzmann, M et al. : "MCM9 Binds Cdt1 and Is Required for the Assembly of Prereplication Complexes" Molecular Cell 31, 190-200, Jul. 25, 2008 ª2008 Elsevier Inc.
Volkening, M et al.: "Involvement of Human MCM8 in Prereplication Complex Assembly by Recruiting hcdc6 to Chromatin" Molecular and Cellular Biology, Feb. 2005, p. 1560-1568, vol. 25, No. 4, Received Oct. 22, 2004/Accepted Nov. 10, 2004.
Gozuacik, D. et al.: Identification and functional characterization of a new member of the human Mcm protein family: hMcm8" 570-579 Nucleic Acids Research, 2003, vol. 31, No. 2, Received Oct. 16, 2002; Revised and Accepted Nov. 6, 2002.
Blanton, H. L. et al.: "REC, Drosophila MCM8, Drives Formation of Meiotic Crossovers" Sep. 2005 vol. 1, Issue 3, e40, PLoS Genetics, Received Jul. 6, 2005; Accepted Aug. 17, 2005; Published Sep. 23, 2005.
He, C. et al.:"Genome-wide association studies identify loci associated with age at menarche and age at natural menopause" (2009) Nat Genet 41, 724-728,Received Sep. 22, 2008; accepted Apr. 21, 2009; published online May 17, 2009, vol. 41.
Stolk, L. et al.: "Loci at chromosomes 13, 19 and 20 influence age at natural menopause" Received Sep. 4, 2008; accepted Apr. 21, 2009; published online May 17, 2009, (2009) Nat Genet 41,645-647.
Arnaudeau, C. et al.: "DNA Double-strand Breaks Associated with Replication Forks are Predominantly Repaired by Homologous Recombination Involving an Exchange Mechanism in Mammalian Cells", J Mol Bioi 307,1235-1245, (2001).
Petermann, E. et al.: "Hydroxyurea-Stalled Replication Forks Become Progressively Inactivated and Require Two Different RAD51-Mediated Pathways for Restart and Repair" Molecular Cell 37, 492-502, Feb. 26, 2010.
Pittman, D. L. et al.: "Meiotic Prophase Arrest with Failure of Chromosome Synapsis in Mice Deficient for Dmc1, a Germline-Specific RecA Homolog" Molecular Cell, vol. 1, 697-705, Apr. 1998, Copyright 1998 by Cell Press.
Handel, M. A. et al.: "Genetics of mammalian meiosis: regulation, dynamics and impact on fertility".Macmillan Publishers Limited, Published online Jan. 6, 2010, vol. 1, 124-136.
Groth, A. et al.: "Human Asf1 Regulates the Flow of S Phase Histones during Replicational Stress" Molecular Cell, vol. 17, 301-311, Jan. 21, 2005.

(Continued)

Primary Examiner — Michael Szperka
(74) Attorney, Agent, or Firm — Young & Thompson

(57) ABSTRACT

The composition includes either an isolated protein complex including MCM8 and MCM9 proteins, or nucleic acid molecules coding for the proteins that constitute the complex, or compounds inhibiting the formation and/or the stability, or the activity of the complex, for its use for enhancing or reducing animal, preferably mammal, fertility.

4 Claims, 30 Drawing Sheets

(56) References Cited

OTHER PUBLICATIONS

Lutzmann et al.: "Identification of full genes and proteins of MCM9. a novel, vertebrate-specific member of the MCM2-8, protein family", Gene vol. 362. Dec. 5, 2005 (Dec. 5, 2005), pp. 51-56. XP005162054, Elsevier. Amsterdam. NL ISSN: 0378-1119. DOI: 10.1016/J.GENE.2005.07.031 the whole document.

Schalk, J.A.C.et al.: "Localization of SCP2 and SCP3 protein molecules within synaptonemal complexes of the rat Chromosoma" Received: Jun. 25, 1998; in revised form: Aug. 4, 1998 / Accepted: Aug. 7, 1998, 540-548.

De Vries, F. A. et al: "Mouse Sycp1 functions in synaptonemal complex assembly, meiotic recombination, and XY body formation" Genes Dev 19, 1376-1389, (2005) Received Nov. 1, 2004; revised version accepted Apr. 18, 2005.

Keeney, S et al.: "Meiosis-Specific DNA Double-Strand Breaks Are Catalyzed by Spo11, a Member of a Widely Conserved Protein Family", Cell, vol. 88, 375-384, Feb. 7, 1997, Department of Molecular and Cellular Biology Harvard University.

Chuang, C. H. et al.: "Incremental Genetic Perturbations to MCM2-7 Expression and Subcellular Distribution Reveal Exquisite Sensitivity of Mice to DNA Replication Stress" Sep. 2010, vol. 6, Issue 9, Retrieved Jun. 1, 2010; Accepted Aug. 3, 2010; Published Sep. 9, 2010.

Naim, V. et al.: "The FANC pathway and mitosis" A replication legacy, vol. 8 Issue 18, Cell Cycle 8, 2907-2911 (2009), Landes Bioscience, Sep. 15, 2009.

Chan, K. L., et al.: "Replication stress induces sister-chromatid bridging at fragile site loci in mitosis" Nature Cell Biology, vol. 11, 753-760, (2009) Received Nov. 19, 2008; accepted Feb. 9, 2009; published online May 24, 2009.

Maya-Mendoza, A. et al.: "Chk1 regulates the density of active replication origins during the vertebrate S phase" The EMBO Journal 26, 2719-2731, (2007), Received: Oct. 24, 2006; accepted: Apr. 17, 2007; published online: May 10, 2007.

Hashimoto, Y., et al.: "Rad51 protects nascent DNA from Mre11-dependent degradation and promotes continuous DNA synthesis", Nat Struct Mol Bioi 17, 1305-1311, (2010), Received Apr. 29; accepted Sep. 8; published online Oct. 10, 2010.

Wang J. et al.: "RelA/p65 functions to maintain cellular senescence by regulating genomic stability and DNA repair", EMBO reports, vol. 10, N. 11, 2009—1272-1278, European Molecular Biology Organization.

Byun, T. S. et al.: "Functional uncoupling of MCM helicase and DNA polymerase activities activates the ATR-dependent checkpoint" Genes & Development 19, 1040-1052, (2005), Received Jan. 25, 2005; revised version accepted Mar. 8, 2005.

Wang, Y. et al.: "BASC, a super complex of BRCA1-associated proteins involved in the recognition and repair of aberrant DNA structures", Genes & Development 14, 927-939 (2000), Received Jan. 21, 2000; revised version accepted Mar. 2, 2000.

Grenon, M., et al.: "Checkpoint activation in response to double-strand breaks requires the Mre11/Rad50/Xrs2 complex" Nature Cell Biology 3, 844-847, (2001).

Lisby, M.et al.: "Choreography of the DNA Damage Response: Spatiotemporal Relationships among Checkpoint and Repair Proteins", Cell, vol. 118, 699-713, Sep. 17, 2004.

Jazayeri, A. et al.: "ATM- and cell cycle-dependent regulation of ATR in response to DNA double-strand breaks" Nature Cell BIOLOGY8, 37-45, (2006), Received Sep. 2, 2005; accepted Nov. 4, 2005; published online: Dec. 4, 2005.

Harrison, et al: "Surviving the Breakup: The DNA Damage Checkpoint" Annu Rev Genet 40,209-235, (2006), First published online as a Review in Advance on Jun. 28, 2006.

Bernstein, K. A. et al.: "At Loose Ends: Resecting a Double-Strand Break" Leading Edge, Minireview, Cell 137, 807-810, (2009) Columbia University Medical Center, Department of Genetics & Development.

Lutzmann Mali K et al.: "MCM8- and MCM9-Deficient Mice Reveal Gametogenesis Defects and Genome Instability Due to Impaired Homologous Recombination.", Molecular Cell Aug. 24, 2012 LNKDPUBMED: 22771120, vol. 47, No. 4, Aug. 24, 2012 (Aug. 24, 2012), pp. 523-534, XP002684750, ISSN: 1097-4164 the whole document.

Khanna, K. K et al.: "DNA double-strand breaks: signaling, repair and the cancer connection" nature genetics 27,247-254, (2001) Received Oct. 25, 2000; accepted Jan. 29, 2001.

Shrivastav, M. et al.: "Regulation of DNA double-strand break repair pathway choice" Cell Res 18, 134-147, (2008), 1Department of Molecular Genetics and Microbiology, University of New Mexico School of Medicine and Cancer Center.

De Villartay, J. P. et al.: "The Mechanisms of Immune Diversification and Their Disorders" Nat Rev Immunol 3, 962-972, (2003).

Blow, J. J. et al.: "How dormant origins promote complete genome replication" Trends in Biochemical Sciences Aug. 2011, vol. 36, No. 8.

Zou, L. et al.: "Sensing DNA Damage Through Atrip Recognition of RPA-ssDNA Complexes" Feb. 18, 2003; accepted May 6, 2003, Published online May 22, 2003, Science 300, 1542-1548, (2003).

Choi et al.: "Reconstitution of RPA-covered single-stranded DNA-activated ATR-Ghk1 signaling" Proc Natl Aced Sci USA 107, 13660-13665, (2010).

Maiorano D et al.: "MCM proteins and DNA replication", Current Opinion in Cell Biology, vol. 18. No. 2. Apr. 1, 2006 (Apr. 1, 2006), pp. 130-136. X10024960173, Current Science. London. GB, ISSN: 0955-0674, DOI:10.1016/J.CEB.2006.02.006 [retrieved on Apr. 1, 2006] the whole document.

Hartford et al.: "Minichromosome maintenance helicase paralog MCM9 is dispensable for DNA replication but functions in germ-line stem cells and tumor suppression.", Proceedings of the National Academy of Sciences of the United States of America, Oct. 25, 2011;108(43):17702-7.

International Search Report, dated Jan. 22, 2013, from corresponding PCT application.

* cited by examiner

MCM8 +/+

MCM8 -/-

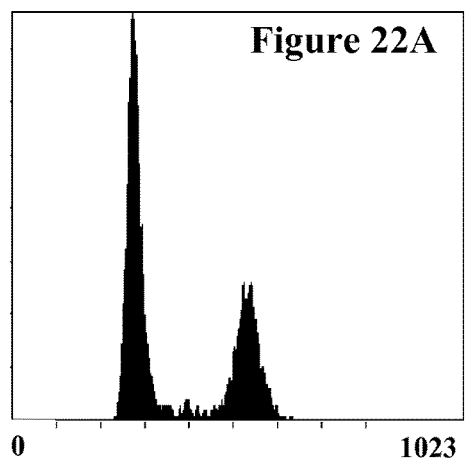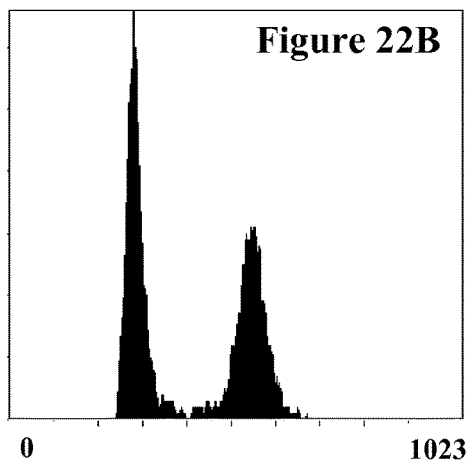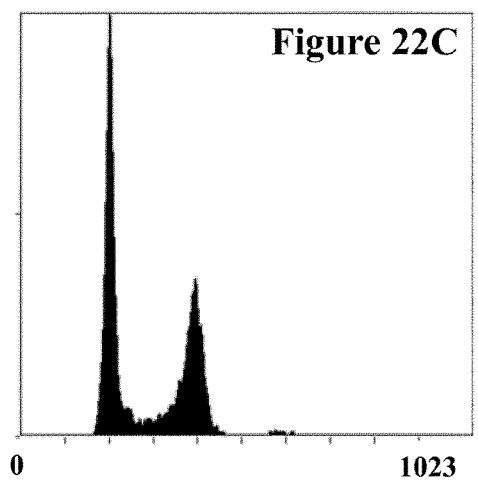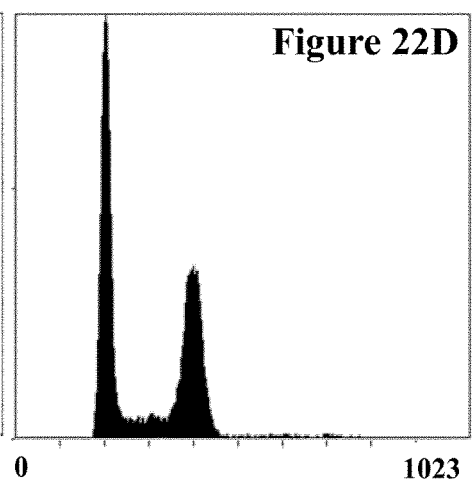

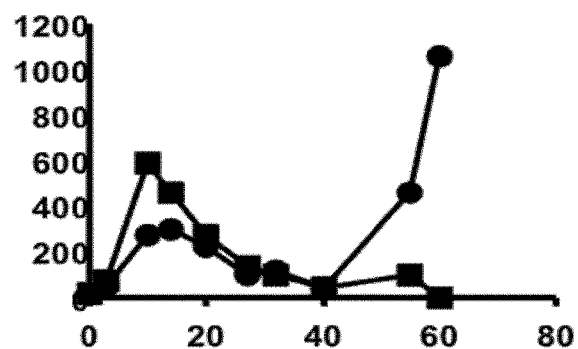
Figure 27
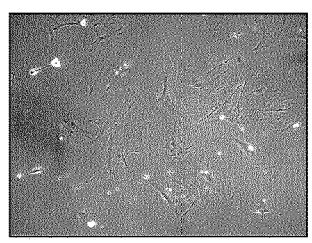 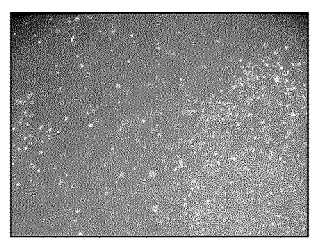 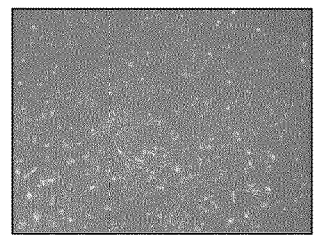
Figure 28A     Figure 28B     Figure 28C
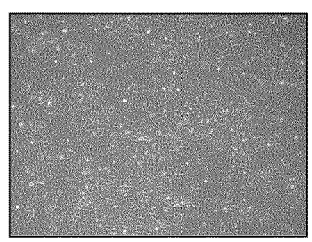 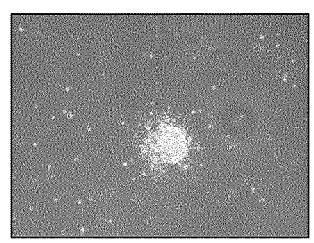 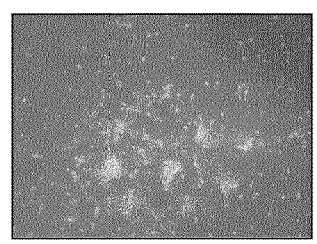
Figure 28D     Figure 28E     Figure 28F
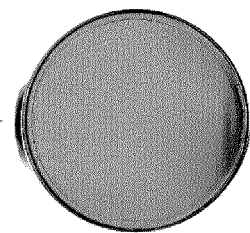 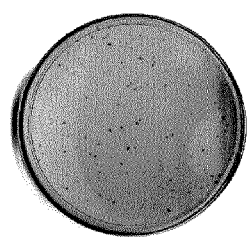
Figure 28G     Figure 28H

SEQUENCE LISTING

```
<160> NUMBER OF SEQ ID NOS: 20

<210> SEQ ID NO 1
<211> LENGTH: 824
<212> TYPE: PRT
<213> ORGANISM: Homo sapiens

<400> SEQUENCE: 1

Met Asn Gly Glu Tyr Arg Gly Arg Gly Phe Gly Arg Gly Arg Phe Gln
1               5                   10                  15

Ser Trp Lys Arg Gly Arg Gly Gly Asn Phe Ser Gly Lys Trp Arg
            20                  25                  30

Glu Arg Glu His Arg Pro Asp Leu Ser Lys Thr Thr Gly Lys Arg Thr
        35                  40                  45

Ser Glu Gln Thr Pro Gln Phe Leu Leu Ser Thr Lys Thr Pro Gln Ser
    50                  55                  60
```

```
Met Gln Ser Thr Leu Asp Arg Phe Ile Pro Tyr Lys Gly Trp Lys Leu
 65                  70                  75                  80

Tyr Phe Ser Glu Val Tyr Ser Asp Ser Ser Pro Leu Ile Glu Lys Ile
                 85                  90                  95

Gln Ala Phe Glu Lys Phe Phe Thr Arg His Ile Asp Leu Tyr Asp Lys
            100                 105                 110

Asp Glu Ile Glu Arg Lys Gly Ser Ile Leu Val Asp Phe Lys Glu Leu
        115                 120                 125

Thr Glu Gly Gly Glu Val Thr Asn Leu Ile Pro Asp Ile Ala Thr Glu
    130                 135                 140

Leu Arg Asp Ala Pro Glu Lys Thr Leu Ala Cys Met Gly Leu Ala Ile
145                 150                 155                 160

His Gln Val Leu Thr Lys Asp Leu Glu Arg His Ala Ala Glu Leu Gln
                165                 170                 175

Ala Gln Glu Gly Leu Ser Asn Asp Gly Glu Thr Met Val Asn Val Pro
            180                 185                 190

His Ile His Ala Arg Val Tyr Asn Tyr Glu Pro Leu Thr Gln Leu Lys
        195                 200                 205

Asn Val Arg Ala Asn Tyr Tyr Gly Lys Tyr Ile Ala Leu Arg Gly Thr
    210                 215                 220

Val Val Arg Val Ser Asn Ile Lys Pro Leu Cys Thr Lys Met Ala Phe
225                 230                 235                 240

Leu Cys Ala Ala Cys Gly Glu Ile Gln Ser Phe Pro Leu Pro Asp Gly
                245                 250                 255

Lys Tyr Ser Leu Pro Thr Lys Cys Pro Val Pro Val Cys Arg Gly Arg
            260                 265                 270

Ser Phe Thr Ala Leu Arg Ser Ser Pro Leu Thr Val Thr Met Asp Trp
        275                 280                 285

Gln Ser Ile Lys Ile Gln Glu Leu Met Ser Asp Gln Arg Glu Ala
    290                 295                 300

Gly Arg Ile Pro Arg Thr Ile Glu Cys Glu Leu Val His Asp Leu Val
305                 310                 315                 320

Asp Ser Cys Val Pro Gly Asp Thr Val Thr Ile Thr Gly Ile Val Lys
                325                 330                 335

Val Ser Asn Ala Glu Glu Ala Asn Ser Ile Ser Asn Ser Lys Gly Gln
            340                 345                 350

Lys Thr Lys Ser Ser Glu Asp Gly Cys Lys His Gly Met Leu Met Glu
        355                 360                 365

Phe Ser Leu Lys Asp Leu Tyr Ala Ile Gln Glu Ile Gln Ala Glu Glu
    370                 375                 380

Asn Leu Phe Lys Leu Ile Val Asn Ser Leu Cys Pro Val Ile Phe Gly
385                 390                 395                 400

His Glu Leu Val Lys Ala Gly Leu Ala Leu Ala Leu Phe Gly Gly Ser
                405                 410                 415

Gln Lys Tyr Ala Asp Asp Lys Asn Arg Ile Pro Ile Arg Gly Asp Pro
            420                 425                 430

His Ile Leu Val Val Gly Asp Pro Gly Leu Gly Lys Ser Gln Met Leu
        435                 440                 445

Gln Ala Ala Cys Asn Val Ala Pro Arg Gly Val Tyr Val Cys Gly Asn
    450                 455                 460

Thr Thr Thr Thr Ser Gly Leu Thr Val Thr Leu Ser Lys Asp Ser Ser
465                 470                 475                 480
```

```
Ser Gly Asp Phe Ala Leu Glu Ala Gly Ala Leu Val Leu Gly Asp Gln
            485                 490                 495

Gly Ile Cys Gly Ile Asp Glu Phe Asp Lys Met Gly Asn Gln His Gln
        500                 505                 510

Ala Leu Leu Glu Ala Met Glu Gln Gln Ser Ile Ser Leu Ala Lys Ala
        515                 520                 525

Gly Val Val Cys Ser Leu Pro Ala Arg Thr Ser Ile Ile Ala Ala Ala
        530                 535                 540

Asn Pro Val Gly Gly His Tyr Asn Lys Ala Lys Thr Val Ser Glu Asn
545                 550                 555                 560

Leu Lys Met Gly Ser Ala Leu Leu Ser Arg Phe Asp Leu Val Phe Ile
            565                 570                 575

Leu Leu Asp Thr Pro Asn Glu His His Asp His Leu Leu Ser Glu His
            580                 585                 590

Val Ile Ala Ile Arg Ala Gly Lys Gln Arg Thr Ile Ser Ser Ala Thr
            595                 600                 605

Val Ala Arg Met Asn Ser Gln Asp Ser Asn Thr Ser Val Leu Glu Val
        610                 615                 620

Val Ser Glu Lys Pro Leu Ser Glu Arg Leu Lys Val Val Pro Gly Glu
625                 630                 635                 640

Thr Ile Asp Pro Ile Pro His Gln Leu Leu Arg Lys Tyr Ile Gly Tyr
            645                 650                 655

Ala Arg Gln Tyr Val Tyr Pro Arg Leu Ser Thr Glu Ala Ala Arg Val
            660                 665                 670

Leu Gln Asp Phe Tyr Leu Glu Leu Arg Lys Gln Ser Gln Arg Leu Asn
        675                 680                 685

Ser Ser Pro Ile Thr Thr Arg Gln Leu Glu Ser Leu Ile Arg Leu Thr
690                 695                 700

Glu Ala Arg Ala Arg Leu Glu Leu Arg Glu Glu Ala Thr Lys Glu Asp
705                 710                 715                 720

Ala Glu Asp Ile Val Glu Ile Met Lys Tyr Ser Met Leu Gly Thr Tyr
            725                 730                 735

Ser Asp Glu Phe Gly Asn Leu Asp Phe Glu Arg Ser Gln His Gly Ser
        740                 745                 750

Gly Met Ser Asn Arg Ser Thr Ala Lys Arg Phe Ile Ser Ala Leu Asn
        755                 760                 765

Asn Val Ala Glu Arg Thr Tyr Asn Asn Ile Phe Gln Phe His Gln Leu
        770                 775                 780

Arg Gln Ile Ala Lys Glu Leu Asn Ile Gln Val Ala Asp Phe Glu Asn
785                 790                 795                 800

Phe Ile Gly Ser Leu Asn Asp Gln Gly Tyr Leu Leu Lys Lys Gly Pro
            805                 810                 815

Lys Val Tyr Gln Leu Gln Thr Met
            820

<210> SEQ ID NO 2
<211> LENGTH: 1143
<212> TYPE: PRT
<213> ORGANISM: Homo sapiens

<400> SEQUENCE: 2

Met Asn Ser Asp Gln Val Thr Leu Val Gly Gln Val Phe Glu Ser Tyr
1               5                   10                  15

Val Ser Glu Tyr His Lys Asn Asp Ile Leu Leu Ile Leu Lys Glu Arg
            20                  25                  30
```

-continued

```
Asp Glu Asp Ala His Tyr Pro Val Val Asn Ala Met Thr Leu Phe
         35                  40                  45

Glu Thr Asn Met Glu Ile Gly Glu Tyr Phe Asn Met Phe Pro Ser Glu
 50                  55                  60

Val Leu Thr Ile Phe Asp Ser Ala Leu Arg Arg Ser Ala Leu Thr Ile
 65                  70                  75                  80

Leu Gln Ser Leu Ser Gln Pro Glu Ala Val Ser Met Lys Gln Asn Leu
                 85                  90                  95

His Ala Arg Ile Ser Gly Leu Pro Val Cys Pro Glu Leu Val Arg Glu
            100                 105                 110

His Ile Pro Lys Thr Lys Asp Val Gly His Phe Leu Ser Val Thr Gly
            115                 120                 125

Thr Val Ile Arg Thr Ser Leu Val Lys Val Leu Glu Phe Glu Arg Asp
130                 135                 140

Tyr Met Cys Asn Lys Cys Lys His Val Phe Val Ile Lys Ala Asp Phe
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
            180                 185                 190

Pro Thr Arg Cys Arg Asp Tyr Gln Glu Ile Lys Ile Gln Glu Gln Val
            195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240

Tyr Gly Ile Val Met Gln Arg Trp Lys Pro Phe Gln Gln Asp Val Arg
                245                 250                 255

Cys Glu Val Glu Ile Val Leu Lys Ala Asn Tyr Ile Gln Val Asn Asn
            260                 265                 270

Glu Gln Ser Ser Gly Ile Ile Met Asp Glu Glu Val Gln Lys Glu Phe
            275                 280                 285

Glu Asp Phe Trp Glu Tyr Tyr Lys Ser Asp Pro Phe Ala Gly Arg Asn
290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                325                 330                 335

Ala Thr Gly Thr Arg Val Arg Gly Glu Ser His Leu Leu Val Gly
            340                 345                 350

Asp Pro Gly Thr Gly Lys Ser Gln Phe Leu Lys Tyr Ala Ala Lys Ile
            355                 360                 365

Thr Pro Arg Ser Val Leu Thr Thr Gly Ile Gly Ser Thr Ser Ala Gly
    370                 375                 380

Leu Thr Val Thr Ala Val Lys Asp Ser Gly Glu Trp Asn Leu Glu Ala
385                 390                 395                 400

Gly Ala Leu Val Leu Ala Asp Ala Gly Leu Cys Cys Ile Asp Glu Phe
                405                 410                 415

Asn Ser Leu Lys Glu His Asp Arg Thr Ser Ile His Glu Ala Met Glu
            420                 425                 430

Gln Gln Thr Ile Ser Val Ala Lys Ala Gly Leu Val Cys Lys Leu Asn
            435                 440                 445
```

```
Thr Arg Thr Thr Ile Leu Ala Ala Thr Asn Pro Lys Gly Gln Tyr Asp
    450                 455                 460

Pro Gln Glu Ser Val Ser Val Asn Ile Ala Leu Gly Ser Pro Leu Leu
465                 470                 475                 480

Ser Arg Phe Asp Leu Ile Leu Val Leu Leu Asp Thr Lys Asn Glu Asp
                485                 490                 495

Trp Asp Arg Ile Ile Ser Ser Phe Ile Leu Glu Asn Lys Gly Tyr Pro
            500                 505                 510

Ser Lys Ser Glu Lys Leu Trp Ser Met Glu Lys Met Lys Thr Tyr Phe
        515                 520                 525

Cys Leu Ile Arg Asn Leu Gln Pro Thr Leu Ser Asp Val Gly Asn Gln
530                 535                 540

Val Leu Leu Arg Tyr Tyr Gln Met Gln Arg Gln Ser Asp Cys Arg Asn
545                 550                 555                 560

Ala Ala Arg Thr Thr Ile Arg Leu Leu Glu Ser Leu Ile Arg Leu Ala
                565                 570                 575

Glu Ala His Ala Arg Leu Met Phe Arg Asp Thr Val Thr Leu Glu Asp
            580                 585                 590

Ala Ile Thr Val Val Ser Val Met Glu Ser Ser Met Gln Gly Gly Ala
        595                 600                 605

Leu Leu Gly Gly Val Asn Ala Leu His Thr Ser Phe Pro Glu Asn Pro
610                 615                 620

Gly Glu Gln Tyr Gln Arg Gln Cys Glu Leu Ile Leu Glu Lys Leu Glu
625                 630                 635                 640

Leu Gln Ser Leu Leu Ser Glu Glu Leu Arg Arg Leu Glu Arg Leu Gln
                645                 650                 655

Asn Gln Ser Val His Gln Ser Gln Pro Arg Val Leu Glu Val Glu Thr
            660                 665                 670

Thr Pro Gly Ser Leu Arg Asn Gly Pro Gly Glu Glu Ser Asn Phe Arg
        675                 680                 685

Thr Ser Ser Gln Gln Glu Ile Asn Tyr Ser Thr His Ile Phe Ser Pro
690                 695                 700

Gly Gly Ser Pro Glu Gly Ser Pro Val Leu Asp Pro Pro His Leu
705                 710                 715                 720

Glu Pro Asn Arg Ser Thr Ser Arg Lys His Ser Ala Gln His Lys Asn
                725                 730                 735

Asn Arg Asp Asp Ser Leu Asp Trp Phe Asp Phe Met Ala Thr His Gln
            740                 745                 750

Ser Glu Pro Lys Asn Thr Val Val Ser Pro His Pro Lys Thr Ser
        755                 760                 765

Gly Glu Asn Met Ala Ser Lys Ile Ser Asn Ser Thr Ser Gln Gly Lys
770                 775                 780

Glu Lys Ser Glu Pro Gly Gln Arg Ser Lys Val Asp Ile Gly Leu Leu
785                 790                 795                 800

Pro Ser Pro Gly Glu Thr Gly Val Pro Trp Arg Ala Asp Asn Val Glu
                805                 810                 815

Ser Asn Lys Lys Lys Arg Leu Ala Leu Asp Ser Glu Ala Ala Val Ser
            820                 825                 830

Ala Asp Lys Pro Asp Ser Val Leu Thr His His Val Pro Arg Asn Leu
        835                 840                 845

Gln Lys Leu Cys Lys Glu Arg Ala Gln Lys Leu Cys Arg Asn Ser Thr
850                 855                 860
```

```
Arg Val Pro Ala Gln Cys Thr Val Pro Ser His Pro Gln Ser Thr Pro
865                 870                 875                 880

Val His Ser Pro Asp Arg Arg Leu Asp Ser Pro Lys Arg Lys Arg Pro
                885                 890                 895

Lys Ser Leu Ala Gln Val Glu Glu Pro Ala Ile Glu Asn Val Lys Pro
            900                 905                 910

Pro Gly Ser Pro Val Ala Lys Leu Ala Lys Phe Thr Phe Lys Gln Lys
        915                 920                 925

Ser Lys Leu Ile His Ser Phe Glu Asp His Ser His Val Ser Pro Gly
    930                 935                 940

Ala Thr Lys Ile Ala Val His Ser Pro Lys Ile Ser Gln Arg Arg Thr
945                 950                 955                 960

Arg Arg Asp Ala Ala Leu Pro Val Lys Arg Pro Gly Lys Leu Thr Ser
                965                 970                 975

Thr Pro Gly Asn Gln Ile Ser Ser Gln Pro Gln Gly Glu Thr Lys Glu
            980                 985                 990

Val Ser Gln Gln Pro Pro Glu Lys His Gly Pro Arg Glu Lys Val Met
        995                 1000                1005

Cys Ala Pro Glu Lys Arg Ile Ile Gln Pro Glu Leu Glu Leu Gly
    1010                1015                1020

Asn Glu Thr Gly Cys Ala His Leu Thr Cys Glu Gly Asp Lys Lys
    1025                1030                1035

Glu Glu Val Ser Gly Ser Asn Lys Ser Gly Lys Val His Ala Cys
    1040                1045                1050

Thr Leu Ala Arg Leu Ala Asn Phe Cys Phe Thr Pro Pro Ser Glu
    1055                1060                1065

Ser Lys Ser Lys Ser Pro Pro Glu Arg Lys Asn Arg Gly Glu
    1070                1075                1080

Arg Gly Pro Ser Ser Pro Thr Thr Thr Ala Pro Met Arg Val
    1085                1090                1095

Ser Lys Arg Lys Ser Phe Gln Leu Arg Gly Ser Thr Glu Lys Leu
    1100                1105                1110

Ile Val Ser Lys Glu Ser Leu Phe Thr Leu Pro Glu Leu Gly Asp
    1115                1120                1125

Glu Ala Phe Asp Cys Asp Trp Asp Glu Glu Met Arg Lys Lys Ser
    1130                1135                1140

<210> SEQ ID NO 3
<211> LENGTH: 833
<212> TYPE: PRT
<213> ORGANISM: Mus musculus

<400> SEQUENCE: 3

Met Ser Gly Ala Tyr Arg Gly Arg Gly Phe Gly Arg Gly Arg Phe Gln
1               5                   10                  15

Ser Trp Lys Arg Gly Arg Gly Gly Asn Phe Ser Gly Arg Trp Arg
            20                  25                  30

Glu Arg Glu Asn Arg Val Asp Leu Asn Glu Ala Ser Gly Lys His Ala
            35                  40                  45

Ser Ala Gln Ala Ser Gln Pro Leu Leu Gln Gln Ser Thr Leu Asp Gln
        50                  55                  60

Phe Ile Pro Tyr Lys Gly Trp Lys Leu Tyr Ser Glu Val Tyr Ser
65                  70                  75                  80

Asn Asn Ser Pro Phe Ile Glu Lys Ile Gln Ala Phe Glu Lys Phe Phe
                85                  90                  95
```

```
Thr Arg His Ile Asp Leu Tyr Asp Lys Asp Glu Ile Glu Arg Lys Gly
                100                 105                 110

Ser Ile Leu Val Asp Phe Lys Glu Leu Thr Lys Ala Asp Glu Ile Thr
            115                 120                 125

Asn Leu Ile Pro Asp Ile Glu Asn Ala Leu Arg Asp Ala Pro Glu Lys
        130                 135                 140

Thr Leu Ala Cys Met Gly Leu Ala Ile His Gln Val Leu Thr Lys Asp
145                 150                 155                 160

Leu Glu Arg His Ala Ala Glu Leu Gln Ala Gln Glu Gly Leu Ser Asn
                165                 170                 175

Gly Gly Glu Thr Met Val Asn Val Pro His Ile Tyr Ala Arg Val Tyr
            180                 185                 190

Asn Tyr Glu Pro Leu Thr His Leu Lys Asn Ile Arg Ala Thr Cys Tyr
        195                 200                 205

Gly Lys Tyr Ile Ser Ile Arg Gly Thr Val Val Arg Val Ser Asn Ile
210                 215                 220

Lys Pro Leu Cys Thr Asn Met Ala Phe Gln Cys Ala Ala Cys Gly Glu
225                 230                 235                 240

Ile Gln Ser Phe Pro Leu Pro Asp Gly Lys Tyr Thr Leu Pro Thr Lys
                245                 250                 255

Cys Pro Val Pro Ala Cys Arg Gly Arg Ser Phe Ala Pro Leu Arg Ser
            260                 265                 270

Ser Pro Leu Thr Val Thr Leu Asp Trp Gln Leu Ile Lys Ile Gln Glu
        275                 280                 285

Leu Met Ser Asp Ala Gln Arg Glu Ala Gly Arg Ile Pro Arg Thr Ile
290                 295                 300

Glu Cys Glu Leu Val His Asp Leu Val Asp Ser Cys Val Pro Gly Asp
305                 310                 315                 320

Thr Val Thr Val Thr Gly Ile Val Lys Val Ser Asn Ser Glu Glu Gly
                325                 330                 335

Ser Arg Asn Lys Asn Asp Lys Cys Met Phe Leu Leu Tyr Ile Glu Ala
            340                 345                 350

Asn Ser Val Ser Asn Ser Lys Gly Pro Lys Ala Gln Thr Ala Glu Asp
        355                 360                 365

Gly Cys Lys His Gly Thr Leu Met Glu Phe Ser Leu Lys Asp Leu Tyr
370                 375                 380

Ala Ile Arg Glu Ile Gln Ala Glu Glu Asn Leu Leu Lys Leu Val Val
385                 390                 395                 400

Asn Ser Leu Cys Pro Val Ile Phe Gly His Glu Leu Val Lys Ala Gly
                405                 410                 415

Leu Thr Leu Ala Leu Phe Gly Gly Ser Gln Lys Tyr Ala Asp Asp Lys
            420                 425                 430

Asn Arg Ile Pro Ile Arg Gly Asp Pro His Val Leu Ile Val Gly Asp
        435                 440                 445

Pro Gly Leu Gly Lys Ser Gln Met Leu Gln Ala Ala Cys Asn Val Ala
450                 455                 460

Pro Arg Gly Val Tyr Val Cys Gly Asn Thr Thr Thr Ser Ser Gly Leu
465                 470                 475                 480

Thr Val Thr Leu Ser Lys Asp Ser Ser Gly Asp Phe Ala Leu Glu
                485                 490                 495

Ala Gly Ala Leu Val Leu Gly Asp Gln Gly Ile Cys Gly Ile Asp Glu
            500                 505                 510
```

```
Phe Asp Lys Met Gly Asn Gln His Gln Ala Leu Leu Glu Ala Met Glu
            515                 520                 525

Gln Gln Ser Ile Ser Leu Ala Lys Ala Gly Val Val Cys Ser Leu Pro
        530                 535                 540

Ala Arg Thr Ser Ile Val Ala Ala Asn Pro Val Gly Gly His Tyr
545                 550                 555                 560

Asn Lys Ala Arg Thr Val Ser Glu Asn Leu Lys Met Gly Ser Ala Leu
                565                 570                 575

Leu Ser Arg Phe Asp Leu Val Phe Ile Leu Leu Asp Thr Pro Asn Glu
            580                 585                 590

Gln His Asp His Leu Leu Ser Glu His Val Ile Ala Ile Arg Ala Gly
        595                 600                 605

Lys Gln Lys Ala Val Ser Ser Ala Thr Val Thr Arg Val Leu Ser Gln
    610                 615                 620

Asp Ser Asn Thr Ser Val Leu Glu Val Val Ser Glu Lys Pro Leu Ser
625                 630                 635                 640

Glu Arg Leu Lys Val Ala Pro Gly Glu Gln Thr Asp Pro Ile Pro His
                645                 650                 655

Gln Leu Leu Arg Lys Tyr Ile Gly Tyr Ala Arg Gln Tyr Val His Pro
            660                 665                 670

Arg Leu Ser Thr Asp Ala Ala Gln Ala Leu Gln Asp Phe Tyr Leu Glu
        675                 680                 685

Leu Arg Lys Gln Ser Gln Arg Val Gly Ser Ser Pro Ile Thr Thr Arg
    690                 695                 700

Gln Leu Glu Ser Leu Ile Arg Leu Thr Glu Ala Arg Ala Arg Leu Glu
705                 710                 715                 720

Leu Arg Glu Glu Ala Thr Arg Glu Asp Ala Glu Asp Ile Ile Glu Ile
                725                 730                 735

Met Lys His Ser Met Leu Gly Thr Tyr Ser Asp Glu Phe Gly Asn Leu
            740                 745                 750

Asp Phe Glu Arg Ser Gln His Gly Ser Gly Met Ser Asn Arg Ser Thr
        755                 760                 765

Ala Lys Arg Phe Ile Ser Ala Leu Asn Ser Ile Ala Glu Arg Thr Tyr
    770                 775                 780

Asn Asn Ile Phe Gln Tyr His Gln Leu Arg Gln Ile Ala Lys Glu Leu
785                 790                 795                 800

Asn Ile Gln Val Ala Asp Phe Glu Asn Phe Ile Gly Ser Leu Asn Asp
                805                 810                 815

Gln Gly Tyr Leu Leu Lys Lys Gly Pro Lys Ile Tyr Gln Leu Gln Thr
            820                 825                 830

Met

<210> SEQ ID NO 4
<211> LENGTH: 1290
<212> TYPE: PRT
<213> ORGANISM: Mus musculus

<400> SEQUENCE: 4

Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
                20                  25                  30

Arg Leu Val Arg Pro Lys Pro Arg Leu Gln Leu Pro Glu Ser Arg Leu
            35                  40                  45
```

-continued

```
Ser Pro Cys Ser Arg Leu Pro Leu Ala Asp Ser Ser Val Arg Pro Gly
     50                  55                  60
Ala Arg Pro Pro Ala Ser Ala Pro Gly Arg Ser Pro Ser Gly Arg Lys
 65                  70                  75                  80
Val Glu Ala Val Arg Gly Ser Gly Ser Ala Gly Ser Ser Ser Pro Ser
                 85                  90                  95
Glu Ala Glu Arg Glu Gln Arg Glu Glu Ala Cys Ala Pro Pro Arg Lys
            100                 105                 110
Ala Ala Pro Ser Ser Gly Arg Ala His Ala Pro Pro Pro Thr Pro
        115                 120                 125
Arg Gly Ser Gly Trp Gly Asp His Gly Arg Ser Ala Val Pro Ala Thr
130                 135                 140
Lys Thr Val Arg Val Glu Pro Tyr Pro Pro Phe Lys Met Asn Ser Glu
145                 150                 155                 160
Gln Val Thr Leu Val Gly Gln Val Phe Glu Ser Tyr Val Ser Glu Tyr
                165                 170                 175
His Lys Asn Asp Ile Leu Leu Ile Leu Lys Glu Arg Asp Glu Asp Ala
            180                 185                 190
His Tyr Pro Val Val Asn Ala Met Ser Leu Phe Glu Thr Asn Met
        195                 200                 205
Glu Ile Gly Asp Tyr Phe Thr Val Phe Pro Asn Glu Val Leu Thr Val
210                 215                 220
Phe Asp Ser Ala Leu Arg Arg Ser Ala Leu Ala Ile Leu Gln Ser Leu
225                 230                 235                 240
Pro Glu Thr Glu Gly Leu Ser Met Lys Gln Asn Leu His Ala Arg Ile
                245                 250                 255
Ser Gly Leu Pro Val Cys Pro Glu Leu Val Arg Glu His Ile Pro Lys
            260                 265                 270
Thr Lys Asp Val Gly His Phe Leu Ser Val Thr Gly Thr Val Ile Arg
        275                 280                 285
Thr Ser Leu Val Lys Val Leu Glu Phe Glu Arg Asp Tyr Met Cys Asn
290                 295                 300
Lys Cys Lys His Val Phe Met Val Glu Ala Asp Phe Glu Gln Tyr Tyr
305                 310                 315                 320
Thr Phe Ser Arg Pro Ser Ser Cys Pro Ser Leu Ala Ser Cys Asp Ser
                325                 330                 335
Ser Lys Phe Ser Cys Leu Ser Asp Leu Ser Ser Pro Ala Arg Cys
            340                 345                 350
Arg Asp Tyr Gln Glu Ile Lys Ile Gln Glu Gln Val Gln Arg Leu Ser
        355                 360                 365
Val Gly Ser Ile Pro Arg Ser Met Lys Val Ile Leu Glu Asp Asp Leu
370                 375                 380
Val Asp Ser Cys Lys Ser Gly Asp Asp Leu Thr Ile Tyr Gly Val Val
385                 390                 395                 400
Met Gln Arg Trp Lys Pro Phe Gln Arg Asp Val Arg Cys Glu Val Glu
                405                 410                 415
Ile Val Leu Lys Ala Asn Tyr Val Gln Val Asn Glu Gln Ser Ser
            420                 425                 430
Gly Met Val Met Asp Glu Asp Thr Arg Lys Glu Phe Glu Asp Phe Trp
        435                 440                 445
Glu His Tyr Lys Ser Asp Pro Phe Ala Gly Arg Asn Glu Ile Leu Ala
450                 455                 460
```

-continued

```
Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala Gly Leu Thr Val Thr
    530                 535                 540

Ala Val Lys Asp Ser Gly Glu Trp Asn Leu Glu Ala Gly Ala Leu Val
545                 550                 555                 560

Leu Ala Asp Ala Gly Leu Cys Cys Ile Asp Glu Phe Asn Ser Leu Lys
                565                 570                 575

Glu His Asp Arg Thr Ser Ile His Glu Ala Met Glu Gln Gln Thr Ile
            580                 585                 590

Ser Val Ala Lys Ala Gly Leu Val Cys Lys Leu Asn Thr Arg Thr Thr
        595                 600                 605

Ile Leu Ala Ala Thr Asn Pro Lys Gly Gln Tyr Asp Pro Lys Glu Ser
    610                 615                 620

Val Ser Val Asn Ile Ala Leu Gly Ser Pro Leu Leu Ser Arg Phe Asp
625                 630                 635                 640

Leu Val Leu Val Leu Leu Asp Thr Arg Asn Glu Asp Trp Asp Arg Ile
                645                 650                 655

Ile Ser Ser Phe Ile Leu Glu Asn Lys Gly Tyr Pro Ser Lys Ser Glu
            660                 665                 670

Asn Leu Trp Ser Met Glu Lys Met Lys Thr Tyr Phe Cys Leu Ile Arg
        675                 680                 685

Asn Leu His Pro Thr Leu Ser Glu Val Ser Asn Gln Val Leu Leu Arg
    690                 695                 700

Tyr Tyr Gln Met Gln Arg Gln Ser Asp Ser Arg Asn Ala Ala Arg Thr
705                 710                 715                 720

Thr Ile Arg Leu Leu Glu Ser Leu Ile Arg Leu Ala Glu Ala His Ala
                725                 730                 735

Arg Leu Met Phe Arg Ser Ala Val Thr Leu Glu Asp Ala Val Thr Ala
            740                 745                 750

Val Ser Val Met Glu Ser Ser Met Gln Gly Ala Leu Leu Gly Gly
        755                 760                 765

Val Asn Ala Leu His Thr Ser Phe Pro Glu Asn Pro Arg Ala Gln Tyr
    770                 775                 780

Gln Arg Gln Cys Glu Leu Ile Leu Glu Lys Leu Glu Leu Gln Gly Leu
785                 790                 795                 800

Leu Gln Glu Glu Leu Arg Arg Leu Glu Arg Leu Gln Asn Glu Ser Val
                805                 810                 815

His Gln Cys Gln Ser His Ser Leu Glu Glu Val Ala Pro Gly Ser
            820                 825                 830

Cys Arg Asn Asp Pro Arg Asp Lys Pro Arg Leu Arg Thr Ser Thr Gln
        835                 840                 845

Gln Glu Gln Ser Cys Ser Trp Ser Ser Thr Gly Arg Ser Gly Ala Asp
    850                 855                 860

Ser Pro Pro Gly Pro Gly Leu Asn Arg Pro Thr Ser Cys Asn Asn Ser
865                 870                 875                 880
```

```
Ala Glu Asn Arg Asp Gly Arg Gly Asp Gly Leu Asp Trp Leu Asp Pro
                885                 890                 895

Thr Ser Ser Pro Glu Ile Ala Pro Glu Ser Thr Ile Val Ser Pro Asn
            900                 905                 910

Val Lys Thr Thr Glu Lys Asn Val Asn Leu Lys Ile Ser Asn Asn Lys
        915                 920                 925

Ser Gln Gly Lys Glu Lys His Gly Pro Gln Arg Ser Lys Leu Leu
    930                 935                 940

Glu Ala Gly His Leu Pro Ser Ser Gly Ala Met Asn Ala Pro Leu Arg
945                 950                 955                 960

Ser His Gly Val Lys Arg Thr Lys Ala Ser Gln Ala Val Val Ser
                965                 970                 975

Glu Ala Gly Arg Gly Asp Glu Glu Asp Ser Val Pro Arg Arg Leu Pro
            980                 985                 990

Lys Leu Leu Lys Glu Gly Ser Gln Asn Val Cys Arg Ser Thr Thr Arg
                995                 1000                1005

Val Arg Pro Leu Pro Pro Thr Val Pro Leu Ser Leu Ser Ile Pro
    1010                1015                1020

Ser Pro Gly Ser Gly Lys Arg Ser Gly Thr Pro Lys Arg Lys Arg
    1025                1030                1035

Arg Lys Ser Ala Gln Val Glu Glu Pro Glu Pro Glu Gly Met Glu
    1040                1045                1050

Thr Pro Thr Val Lys Leu Ala Lys Phe Thr Phe Lys Gln Lys Thr
    1055                1060                1065

Lys Leu Thr His Ser Pro Glu Gly Gln Gly Pro Ile Pro Pro Ser
    1070                1075                1080

Ala Ser Glu Ile Ala Val Asp Ser Ser Lys Ile Pro Gln Gln Arg
    1085                1090                1095

Thr Arg Arg Glu Ala Ala Val Pro Val Val Ala Pro Gly Lys Ser
    1100                1105                1110

Thr Ser Thr Ser Gly Asp Arg Cys Ser Asp Gln Leu His Gly Lys
    1115                1120                1125

Thr Lys Glu Leu Ser Arg Gln Pro Pro Asp Ser Asn Pro Pro Arg
    1130                1135                1140

Glu Glu Arg Glu Gln Gly Pro Lys Arg Arg Val Ile Gln Pro Lys
    1145                1150                1155

Pro Glu Leu Gly Asn Gln Ala Gly His Ser His Leu Ala Cys Glu
    1160                1165                1170

Lys Asp Arg Lys Glu Gly Val Ser Cys Gly Asn Lys Ser Ser Lys
    1175                1180                1185

Val His Ala Gly Thr Ile Ala Arg Leu Ala Ser Phe Ser Phe Thr
    1190                1195                1200

Ser Pro Ser Glu Ser Lys Ser Glu Ser Leu Pro Pro Glu Arg Lys
    1205                1210                1215

Asp Ser Arg Asp Ser Arg Asp Ser Arg Asp Ser Arg Asp Arg Cys
    1220                1225                1230

His Ser Pro Pro Ala Thr Thr Ala Pro Val Leu Gly Gln Gln Arg
    1235                1240                1245

Gln Thr Phe Gln Leu Gln Gln Pro Thr Glu Arg Ala Asn Leu Ser
    1250                1255                1260
```

```
Thr Leu Ser Leu Phe Thr Leu Ser Glu Leu Asp Asp Glu Ala Leu
    1265            1270            1275

Asp Phe Asp Trp Glu Glu Glu Met Arg Lys Lys Pro
    1280            1285            1290
```

```
<210> SEQ ID NO 5
<211> LENGTH: 24
<212> TYPE: DNA
<213> ORGANISM: Artificial Sequence
<220> FEATURE:
<223> OTHER INFORMATION: derived from MCM9

<400> SEQUENCE: 5
atgaatagtg agcaggtcac cctg                                          24

<210> SEQ ID NO 6
<211> LENGTH: 24
<212> TYPE: DNA
<213> ORGANISM: Artificial Sequence
<220> FEATURE:
<223> OTHER INFORMATION: derived from MCM9

<400> SEQUENCE: 6
tcatggcttt ttcctcatct cttc                                          24

<210> SEQ ID NO 7
<211> LENGTH: 22
<212> TYPE: DNA
<213> ORGANISM: Artificial Sequence
<220> FEATURE:
<223> OTHER INFORMATION: derived from actin

<400> SEQUENCE: 7
gccggcttac actgcgcttc tt                                            22

<210> SEQ ID NO 8
<211> LENGTH: 20
<212> TYPE: DNA
<213> ORGANISM: Artificial Sequence
<220> FEATURE:
<223> OTHER INFORMATION: derived from actin

<400> SEQUENCE: 8
ttctggccca tgcccaccat                                               20

<210> SEQ ID NO 9
<211> LENGTH: 20
<212> TYPE: DNA
<213> ORGANISM: Artificial Sequence
<220> FEATURE:
<223> OTHER INFORMATION: derived from MCM9

<400> SEQUENCE: 9
agaccgtggg atacttccaa                                               20

<210> SEQ ID NO 10
<211> LENGTH: 20
<212> TYPE: DNA
<213> ORGANISM: Artificial Sequence
<220> FEATURE:
<223> OTHER INFORMATION: derived from MCM9

<400> SEQUENCE: 10
gatgtcggga ttaccaggaa                                               20
```

-continued

```
<210> SEQ ID NO 11
<211> LENGTH: 18
<212> TYPE: DNA
<213> ORGANISM: Artificial Sequence
<220> FEATURE:
<223> OTHER INFORMATION: derived MCM8

<400> SEQUENCE: 11
gcttggggaa gagtcaga                                                 18

<210> SEQ ID NO 12
<211> LENGTH: 24
<212> TYPE: DNA
<213> ORGANISM: Artificial Sequence
<220> FEATURE:
<223> OTHER INFORMATION: derived from MCM8

<400> SEQUENCE: 12
ggtatttcca caaacataca cacc                                          24

<210> SEQ ID NO 13
<211> LENGTH: 19
<212> TYPE: RNA
<213> ORGANISM: Artificial Sequence
<220> FEATURE:
<223> OTHER INFORMATION: siRNA derived from MCM8

<400> SEQUENCE: 13
ggcaauacau cagguguua                                                19

<210> SEQ ID NO 14
<211> LENGTH: 19
<212> TYPE: RNA
<213> ORGANISM: Artificial Sequence
<220> FEATURE:
<223> OTHER INFORMATION: siRNA derived from MCM8

<400> SEQUENCE: 14
gaacauguga uugcaauaa                                                19

<210> SEQ ID NO 15
<211> LENGTH: 19
<212> TYPE: RNA
<213> ORGANISM: Artificial Sequence
<220> FEATURE:
<223> OTHER INFORMATION: /siRNA derived from MCM8

<400> SEQUENCE: 15
ugauggaguu cucacuuaa                                                19

<210> SEQ ID NO 16
<211> LENGTH: 19
<212> TYPE: RNA
<213> ORGANISM: Artificial Sequence
<220> FEATURE:
<223> OTHER INFORMATION: siRNA derived from MCM8

<400> SEQUENCE: 16
gaaaguacau uggcuaugc                                                19

<210> SEQ ID NO 17
<211> LENGTH: 19
<212> TYPE: RNA
<213> ORGANISM: Artificial Sequence
<220> FEATURE:
<223> OTHER INFORMATION: siRNA derived from MCM9
```

```
<400> SEQUENCE: 17
gaagaugacu uaguggaua                                                19

<210> SEQ ID NO 18
<211> LENGTH: 19
<212> TYPE: RNA
<213> ORGANISM: Artificial Sequence
<220> FEATURE:
<223> OTHER INFORMATION: siRNA derived from MCM9

<400> SEQUENCE: 18
gaaagcaaau uacauccaa                                                19

<210> SEQ ID NO 19
<211> LENGTH: 19
<212> TYPE: RNA
<213> ORGANISM: Artificial Sequence
<220> FEATURE:
<223> OTHER INFORMATION: /siRNA derived from MCM9

<400> SEQUENCE: 19
gaauagcgau caaguuaca                                                19

<210> SEQ ID NO 20
<211> LENGTH: 19
<212> TYPE: RNA
<213> ORGANISM: Artificial Sequence
<220> FEATURE:
<223> OTHER INFORMATION: siRNA derived from MCM9

<400> SEQUENCE: 20
agucauaugu uucggaaua                                                19
```

PROTEIN COMPLEX COMPRISING MCM8 AND MCM9 PROTEINS AND THEIR USE

The present invention relates to a protein complex, inhibitors thereof, and their use as drugs.

At earlier times in history, populations were controlled exclusively by two broad natural processes, mortality control and fertility control. When animal populations exceed the carrying capacity of their environment, animals die from starvation and disease as well as predation. At the same time, high densities among populations lead to a decrease in reproductive success; animals delay the onset of reproduction at early ages, they produce fewer offspring, and juvenile mortality rates increase.

Urbanization and modern agricultural development led to the destruction of predators, and regulated hunting and trapping soon replaced the predators as population control devices. Therefore, there is a need to control expansion of some animals, for which no predators still exist, and treat some infertile animals, including humans, for biodiversity reasons, such as preserving species.

Fertility is the natural capability of giving life. As a measure, "fertility rate" is the number of children born per couple, person or population. Fertility differs from fecundity, which is defined as the potential for reproduction (influenced by gamete production, fertilisation and carrying a pregnancy to term). A lack of fecundity would be called sterility.

Thus, to be fertile, animals need to produce sufficient and efficient germ cells.

Meiosis is the unique and ultimate event of germ cells on which sexual reproduction is based. Meiosis comprises two meiotic divisions. During the first division, exchange between maternal and paternal genes take place before the pairs of chromosomes are separated into the two daughter cells. These contain only half the number (1 n) of chromosomes and 2c DNA. The second meiotic division proceeds without a DNA synthesis. This division therefore results in the formation of the haploid germ cells with only 1c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted.

Meiosis in females is not completed until after fertilization, and results in only one ovum and two abortive polar bodies per germ cell.

In contrast, only some of the male germ cells enter meiosis from puberty and leave a stem population of germ cells throughout life. Once initiated, meiosis in the male cell proceeds without significant delay and produces spermatozoa.

A mechanism essential to preserve genome integrity during both mitotic cell division and the formation of germ cells at meiosis is the repair of double strand DNA breaks by homologous recombination (HR).

The art discloses many compositions that can be used for the control of fertility.

For instance, the international patent application WO 99/61010 describes a pharmaceutical composition comprising c-AMP-increasing compound in low dose so that, when used for the treatment of infertility in mammals, it leads to meiotic maturation without inducing meiotic arrest.

Of the nine MCM family proteins (MCM2-9), MCM2-MCM7 is the major replicative DNA helicase omnipresent in eukaryotes and form an heterohexamer that is recruited at the pre-replication complex (pre-RC) in G1 [Donovan, S., et al. (1997) *Proc Natl Acad Sci USA* 94, 5611-5616; Maiorano, et al. (2000) *J Biol Chem* 275, 8426-8431]. The more recently discovered MCM8 and MCM9 genes are present in all vertebrates, but are missing in the genomes of yeast, *C. elegans* and some other eukaryotic taxa [Liu, Y, et al. (2009) *BMC Evol Biol* 9, 60]. Their function is poorly documented, but they have been involved in DNA replication [Maiorano, D., et al. (2005) *Cell* 120, 315-328, Volkening and Hoffman, 2005 *Mol Cell Biol*, February; 25(4):1560-8; Lutzmann, M & Mechali, M. (2008) *Mol Cell* 31, 190-200]. In *Xenopus* eggs MCM8 is involved at the elongation stage [Maiorano, D., et al. (2005) *Cell* 120, 315-328], whereas in somatic cells it appears involved either in initiation [Volkening, M. & Hoffmann, I. (2005) *Mol Cell Biol* 25, 1560-1568], or elongation [Gozuacik, D. et al. (2003) *Nucleic Acids Res* 31, 570-579].

In *Drosophila*, the REC protein (Recombination Defective) is the *Drosophila* orthologous of MCM8, and Rec mutant flies are defective in the formation of meiotic crossovers, [Blanton et al., 2005, *PLoS Genet.* 1(3), pp: 343-354].

Recently, papers reported that the fertile life span of woman correlates with single nucleotide polymorphisms (SNPs) in the human MCM8 gene [He, C. et al. (2009) *Nat Genet.* 41, 724-728; Stolk, L. et al. (2009) *Nat Genet.* 41, 645-647].

However, these documents remain ambiguous regarding the correlation between the SNP and the precocity/retardation of the menopause.

Thus, to date, it is unclear if the MCM proteins control or not the fertility/sterility in animals.

So there is a need to provide new means for controlling fertility or sterility, acting on the gametes development, said means being not compounds or molecules influencing the hormonal regulation of fertility.

One aim of the invention is to provide a method for controlling fertility or sterility.

Another aim of the invention is to provide a new efficient therapy for treating sterility in animals, in particular mammals.

Also, one ain of the invention is to provide efficient drug controlling fertility, or sterility in animals, in particular mammals.

The invention relates to the use of a composition comprising:
- either an isolated protein complex comprising MCM8 and MCM9 proteins, said MCM8 and MCM9 proteins being two distinct proteins,
- or nucleic acid molecules coding for the proteins that constitute said complex,
- or compounds inhibiting the formation and/or the stability, or the activity of said complex, for enhancing or reducing animal, preferably mammal, fertility, provided that said composition does not modify the germ line genetic identity of human beings.

The present invention is based on the unexpected observation made by the Inventors that lack of MCM8/MCM9 complex induces animal sterility, as observed in mice.

Therefore, the invention is drawn to a composition:
either restoring the absent MCM8/MCM9 complex in sterile animals, rendering them fertile, or inhibiting the formation and/or the stability and/or the activity of said MCM8/MCM9 complex in fertile animals, rendering them sterile.

In the invention "fertility" is used to describe fertility per se, and also fecundity.

The composition according to the invention is used to modulate fertility, i.e. for increasing fertility or reducing fertility.

By "increasing fertility", it is meant in the invention that
- either sterile animals receiving the composition, become fertile,
- or the substerile animals (having a very low fertility) receiving the composition, become fertile.

When said animals become fertile as mentioned above, they are able to reproduce themselves at a level which is similar to the one of the same animal that are non sterile or non substerile. The following example illustrates this purpose:

Fertile mice are able to produce 4 to 8 time a litter of 3-14 young. Sterile mice are unable to obtain young after copulation, and substerile mice have a reduce period of pregnancy over the year and/or reduced litters.

This example applies mutatis mutandis for animals, regarding the definitions of fertile, sterile and substerile.

By "reducing fertility", it is meant in the invention that fertile animals receiving the composition, become sterile or substerile as defined above.

For example, the composition will inhibit or activate the formation of the MCM8-MCM9 complex, or inhibits its DNA helicase activity. In case of humans, the composition will by no means modify the germinal genetic identity, as there will be no modification of the germ line.

The composition according to the invention comprises an isolated complex comprising MCM8 and MCM9 proteins. This complex is "isolated" which means that it as been removed from its natural counterpart.

For instance, the complex can be:
- isolated from animal extracts by the means of immunoprecipitations using antibodies specifically directed against MCM8 and/or MCM9 proteins, or
- isolated from animal extracts by means of affinity/salinity/ion exchange/activity column fractionation,
- isolated from cells that produce recombinant MCM8 and MCM9 or any other methods commonly used by the person having ordinary skilled in biochemistry and in protein complex purifications.

The MCM8/MCM9 complex according to the invention essentially contains the MCM8 protein and the MCM9 protein, said proteins being two distinct proteins.

By "being two distinct proteins", it is meant that MCM8 and MCM9 proteins can be separated from each other in order to provide isolated MCM8 protein and isolated MCM9 protein, under drastic fractionation procedure (high salt concentration, presence of high concentration of reducing agent, high concentration of surfactant, ionic surfactant such as Sodium Dodecil Sulfate . . . ).

Thus, a fusion protein consisting of the fusion of MCM8 immediately upstream to MCM9, or the fusion of MCM9 immediately upstream to MCM9, is excluded from the invention. However, a fusion protein comprising a peptidic sequence between MCM8 and MCM9 sequences or between the MCM9 and the MCM8 sequence, peptidic sequence being a protease site (allowing the proteolysis site-specific in order to produce separated MCM8 and MCM9 proteins) is covered by the invention.

In other words, the fusion proteins excluded from the invention are the ones where the last amino acid of MCM9 is directly linked to the first amino acid of MCM8, and where the last amino acid of MCM8 is directly linked to the first amino acid of MCM9.

The composition according to the invention may also comprise nucleic acid molecules coding for said MCM8 and said MCM9.

Advantageously, said nucleic acid molecules are contained in a vector, said vector comprising the means allowing the expression (transcription and translation) of said nucleic acid molecule, such that MCM8 and MCM9 proteins are expressed.

Said nucleic acid molecules, at least one coding for MCM8 protein and at least one coding for MCM9 protein, can be
- contained in separate vectors: i.e. the composition then comprises at least a first vector comprising a nucleic acid molecule coding for MCM8 and a second vector comprising a nucleic acid molecule coding for MCM9, or
- contained in one vector: i.e. the composition then comprises at least one vector comprising a nucleic acid molecule coding for MCM8 and a nucleic acid molecule coding for MCM9, for instance separated by an Internal Ribosome Entry Site (IRES) sequence, or controlled by two independent promoters (one promoter controlling the expression of MCM8 and another promoter controlling the expression of MCM9, the two promoters being identical or differents).

These alternative are well known for the one skilled in the art.

With the above composition, comprising nucleic acid molecules coding for said MCM8 and MCM9 proteins, it is possible to produce said MCM8/MCM9 complex:
- either by producing said complex in an in vivo or ex vivo systems (bacteria, yeast, insect cells, Reticulocyte lysate, Wheat germ lysate, *E. coli* free cell extract, . . . ),
- or directly produced in vivo; i.e. nucleic acid molecules are expressed in the organism in which the composition has been administered, such that the complex can be formed.

The nucleic acid molecules will then allow the production of both MCM8 and MCM9 protein, which will associate to each other to form the MCM8/MCM9 complex.

Further, in one advantageous embodiment, the MCM8/MCM9 complex, after its isolation, can be stabilized by means of crosslinking (UV or chemical cross linking), association with other proteins or nucleic acid molecules (DNA, RNA, small RNA . . . ), or any other means.

The composition according to the invention can also comprise compounds inhibiting the formation and/or the stability, or the activity of the MCM8/MCM9 complex.

Said compounds can then
- inhibit the formation of the MCM8/MCM9 complex, by interfering with the interactions between MCM8 and MCM9, and/or
- inhibit the stability of said complex, as disclosed in the example, and/or
- inhibit the activity of the complex, for instance by modifying its enzymatic function, inducing its delocalization, inducing its interaction with an interfering molecule . . . .

The DNA helicase activity of the MCM8-MCM9 complex can be activated or inhibited according to the invention.

For example:
  small molecules that inhibit the active site of one or both proteins, competitive or not, like analogs of ATP,
  small molecules that bind or change the interaction/binding sites of MCM8/MCM9 so that a complex formation is reduced/destabilized or the structure of the complex is changed affecting stability or ATPase, helicase activity,
  small molecules that bind or change the chromatin binding sites of MCM8/MCM9 so that the activity of the complex is blocked or reduced,
  peptides that mimic or constitute binding moieties for MCM8 or MCM9 so that complex formation is reduced or blocked.

The inhibition of the formation of the complex can be measured, for instance by immunoprecipitation, by precipitating one of the members of the complex, and identify if the second member is present, as illustrated in example.

One example of test can be as follows:

Cells are transiently transfected with vectors allowing the expression of MCM8 and MCM9 proteins, preferably tagged (for instance by using 6His-, Hemaglutinin (Ha)-, Flag-, Myc-, Glutathion S transferase (GST)-, Maltose Binding Protein (MBP)-tag, V5-tag . . . ); the tag added to MCM8 being different from the tag added to MCM9.

About 24 hours after transfection, compounds liable to interfere with the MCM8/MCM9 formation are added to transfected cells.

After an appropriate incubation, from 10 min to 72 h, cells are collected, lysed into an appropriate buffer (for instance 150 mM NaCl, 50 mM Tris pH 7.5, 5 mM EDTA, 0.3% NP40, 10% glycerol, Phosphatase-inhibitors (Calbiochem), protease-inhibitors Leupeptin, Aprotinin and Pepstatin at a concentration of 10 μg/ml). The lysate is centrifuged at 4° C. for 15 min at 16'000 g. The supernatant is then incubated with the appropriate antibody (anti MCM8 antibody or anti MCM9 antibody, or antibody directed against the tag added to MCM8, or antibody directed against the tag added to MCM9) for 2 h at 4° C. on a turning wheel. 5 μl of ProtA-Agarose beads (Roche) were then added and incubated for another hour. Beads were recovered and washed 6 times with IP buffer and tubes were changed after the first and before the last wash. Beads were finally boiled in three times Laemmli SDS buffer. Immunoprecipitated proteins are then separated by using western blot technique.

If the immunoprecipitation was carried out by using an anti MCM8 antibody or antibody directed against the tag added to MCM8, the membrane is first labelled with an anti MCM9 antibody, or antibody directed against the tag added to MCM9. Further, the membrane is labelled with an anti MCM8 antibody, or antibody directed against the tag added to MCM8.

If the immunoprecipitated protein is present, along with the other protein, thus the compound used does not affect the formation of the complex (for instance, in the case of Ha-MCM8 and Myc-MCM9 and immunoprecipitation using anti Ha-tag, if revelation of the presence of Myc tagged protein is positive, as well as the revelation of Ha-tagged protein, the complex exist, and the complex is formed).

On the contrary, if only the immunoprecipitated protein is detectable, the complex does not exist, and the compound added to cells interfere with the complex formation.

Examples are also provided in the Example section.

Similarly, the formation of the MCM8/MCM9 complex can be measured with in vitro translated MCM8 and MCM9, possibly tagged, proteins.

The formation of the MCM8/MCM9 complex can also be purified by the previously known TAP-tag purification method. A fusion protein with one or two labels FLAG and HA tandem placed on the N or C-terminus is generated (Nakatani and Ogryzko, Methods Enzymol. 2003). Cells expressing the tagged protein are generated by retroviral transduction. After expression of protein FLAG-HA-MCM9 or FLAG-HA-MCM8, nuclear extracts are realised. Purification of the complex is performed by an antibody directed against the FLAG tag and elution with the FLAG peptide. The second purification is performed using the HA tag and also eluted with the corresponding peptide. This double purification eliminates a maximum of nonspecific interactions.

The skilled person knows how to easily adapt the protocol consequently, since these experiments are routine proceedings.

The inhibition of the stability of the complex can be measured, as for the measure of the inhibition of the formation of the complex, but by evaluating over the time, the existence of the complex.

The inhibition of the activity complex can be measured by proceeding to an homologous recombination test, in vitro. If the recombination is defective, the complex has lost its activity.

Recombination assay can be carried out according to Pierce at al. [Pierce et al. (1999) *Genes Dev* 13(20): 2633-2638].

Briefly, cellular clones containing the GFP vector disclosed in Pierce at al., either lacking MCM8 and/or MCM9, or WT, are transfected with nucleic acid molecules coding for MCM8 and MCM9 proteins, in order to allow the formation of the complex. Cells are then treated with compounds liable to modulate the activity of the complex.

If the complex is active, the I-Sce I induced Double Strand Break (DSB) is repaired, and an active GFP gene is generated, allowing the expression of an active (fluorescent) GFP protein. Cells are then analysed for their GFP expression, for instance using Flow cytometer, or fluorescent microscopy.

On the contrary, if the complex is inactive, the I-Sce I induced Double Strand Break (DSB) is not repaired, and no active GFP gene is generated. Thus, no active GFP protein is expressed.

In fine, the compounds mentioned above interfere with the MCM8/MCM9 function in fertility.

Said compounds can be advantageously:
  blocking antibodies directed against MCM8 and/or MCM9 proteins, such that they inhibit the interaction between the two proteins,
  interfering molecules inhibiting the expression of one or both MCM8 and MCM9 proteins, such that siRNA, shRNA, or antisense nucleic acid molecules.
  any chemical compounds able to act as blocking antibodies or interfering molecules as mentioned above.

The invention also relates to a method for enhancing or reducing animal, preferably mammal, fertility, said method comprising the administration of a pharmaceutically acceptable effective amount of a composition comprising:
  either an isolated protein complex comprising MCM8 and MCM9 proteins, said MCM8 and MCM9 proteins being two distinct proteins,
  or nucleic acid molecules coding for the proteins that constitute said complex,
  or compounds inhibiting the formation and/or the stability, or the activity of said complex, in particular provided that said composition does not modify the germ line genetic identity of animal beings, in particular when said animal is a human being.

In the invention, animals are vertebrate animals, in particular mammals. Human and domestic animals are more advantageous, but wild animals are not excluded.

In one advantageous embodiment, the invention relates to the use of a composition as defined above, comprising:
  either an isolated protein complex comprising MCM8 and MCM9 proteins, said MCM8 and MCM9 proteins being two independent proteins,
  or nucleic acid molecules coding for the proteins that constitute said complex,
for enhancing animal, preferably mammal, fertility,
provided that said composition does not modify the germ line genetic identity of human beings.

In one another advantageous embodiment, the invention relates to the use of a composition as defined above, comprising compounds inhibiting the stability or the activity of said complex
for reducing animal, preferably mammal, fertility,
provided that said composition does not modify the germ line genetic identity of animal beings, in particular when said animal is a human being.

Another advantageous embodiment of the invention relates to the use of a composition as defined above, wherein said protein complex is devoid of nucleic acid molecules and possibly formed in vitro.

By "devoid of nucleic acid molecules", it is meant in the invention that the complex according to the invention is not linked to, or associated to, a deoxyribonucleic acid (DNA) molecule which is naturally modified by said MCM8/MCM9 complex. In other words, the MCM8/MCM9 complex repairs DSB and it associates to DSB DNA. Thus the DSB DNA is not present in the isolated complex according to the invention.

In other words, since the MCM8/MCM9 complex acts during homologous recombination, the MCM8/MCM9 complex is linked to DNA in order to allow said recombination. The purified complex according to the invention is not linked to such nucleic acid molecule.

In still another advantageous embodiment, the invention relates to a composition as defined above, wherein said complex is devoid of proteins belonging to the group consisting of MCM2-7, Cdtl and Geminin.

MCM2-7 means MCM2, MCM3, MCM4, MCM5, MCM6 and MCM7 proteins.

Another advantageous embodiment of the invention relates to the use of a composition as defined above, wherein said protein complex essentially consists of MCM8 and MCM9 proteins.

In this advantageous aspect of the invention, the complex contains essentially both MCM 8 and MCM9 proteins, but no other proteins.

The terms "essentially consists" and "essentially contains" means that the MCM8 and MCM9 proteins represents at least 90% of the component of the complex, but some impurities, due to the isolation protocol, can be present, without interfering with the complex formation, stability and activity.

Another advantageous embodiment of the invention relates to a composition previously defined, wherein said MCM8 and said MCM9 proteins are bounded to each other by means of hydrogen bonds, covalent link or any means allowing the formation, the stabilisation and the activity of the complex.

In still another advantageous embodiment, the invention relates to a composition as defined above wherein said MCM8 and MCM9 proteins are present in a molar ratio from 5/1 to 1/5, preferably from 4/1 to 1/4, more preferably from 3/1 to 1/3, more preferably from 2/1 to 1/2, in particular of 1/1.

Said complex can also be a multimer of MCM8 and MCM9 proteins, according to the above ratio.

Thus, if a complex comprises 9 molecules of MCM8 and 3 molecules of MCM9, the ratio is 3/1, but the complex is a multimer.

Another advantageous embodiment of the invention relates to the use of a composition as defined above, wherein
  said MCM8 consists of the amino acid sequence consisting of SEQ ID NO: 1, or a protein sequence substantially identical to SEQ ID NO: 1, and
  said MCM9 consists of the amino acid sequence consisting of SEQ ID NO: 2, or a protein sequence substantially identical to SEQ ID NO: 2.

SEQ ID NO: 1 represents the human MCM8 protein and SEQ ID NO: 2 represent the human MCM9 protein.

The invention is based on the identification by the inventors that MCM8/MCM9 complex acts for controlling homologous recombination, and meiotic crossing-overs.

A "substantially identical" protein sequence differs from a given sequence of MCM8 or MCM9 only by conservative amino acid substitutions or by one or more non-conservative substitutions, deletions, or insertions located at positions which do not destroy the function of the polypeptide compared to wild-type MCM8 or MCM9.

Substantially identical protein sequences also encompass splicing variant, generated by the use of alternative splicing sites, and proteins translated from internal methionine.

Another advantageous embodiment of the invention relates to a composition according to the previous definition, wherein
  said MCM8 consists of the amino acid sequence consisting of SEQ ID NO: 1, or
  said MCM9 consists of the amino acid sequence consisting of SEQ ID NO: 2, or
  said MCM8 consists of the amino acid sequence consisting of SEQ ID NO: 1 and said MCM9 consists of the amino acid sequence consisting of SEQ ID NO: 2.

Another advantageous embodiment of the invention relates to a composition according to the previous definition, wherein
  said MCM8 consists of the amino acid sequence consisting of SEQ ID NO: 3, or
  said MCM9 consists of the amino acid sequence consisting of SEQ ID NO: 4, or
  said MCM8 consists of the amino acid sequence consisting of SEQ ID NO: 3, and said MCM9 consists of the amino acid sequence consisting of SEQ ID NO: 4.

SEQ ID NO: 3 represents the mouse MCM8 protein and SEQ ID NO: 4 represents the mouse MCM9 protein.

Another advantageous embodiment of the invention relates to a composition according to the previous definition, wherein
  said MCM8 consists of the amino acid sequence consisting of SEQ ID NO: 1 or 3, or any homologous MCM8 protein from vertebrate, or
  said MCM9 consists of the amino acid sequence consisting of SEQ ID NO: 2 or 4, or any homologous MCM9 protein from vertebrate, or
  said MCM8 consists of the amino acid sequence consisting of SEQ ID NO: 1 or 3 or any homologous MCM8 protein from vertebrate, and said MCM9 consists of the amino acid sequence consisting of SEQ ID NO: 2 or 4, or any homologous MCM9 protein from vertebrate.

The animal encompassed by the present invention are mouse, rat, cow, pig, chicken, rabbit, horse, wild boar, turkey, goose, goat, sheep, dog, cat, elephant, ostrich, pigeon, ferret, guinea pig, dolphin, opossum, mink, chinchilla, crocodile, xenope . . . without any limitation among vertebrates.

The skilled person can easily obtain the corresponding sequences of the above listed animal either by consulting sequences databases (EBI, GenBank . . . ) or by sequence homology with SEQ ID NO: 1 or 2 and SEQ ID NO: 3 or 4, by using Blast Software. Advantageously, the complex as defined above is such that MCM8 and MCM9 proteins are from the same species. Then, if a human complex is required, it is advantageous that human MCM8 and MCM9 proteins constitute said MCM8/MCM9 complex.

This applies mutatis mutandis for other animals.

The invention also relates to an isolated protein complex comprising MCM8 and MCM9 proteins, said complex being devoid of nucleic acid molecules, said MCM8 and MCM9 proteins being two distinct proteins.

The Complex is substantially pure, and isolated as defined above.

In one advantageous embodiment, the invention relates to an isolated protein complex as defined above, wherein said complex is devoid of proteins belonging to the group consisting of MCM2-7, Cdt1 and Geminin.

In one another advantageous embodiment, the invention relates to an isolated protein complex previously defined, said complex consisting of MCM8 and MCM9 proteins.

Another advantageous embodiment of the invention relates to an isolated protein complex as defined above, wherein
said MCM8 consists of the amino acid sequence consisting of SEQ ID NO: 1 or 3, or any homologous MCM8 protein from vertebrate, or
said MCM9 consists of the amino acid sequence consisting of SEQ ID NO: 2 or 4, or any homologous MCM9 protein from vertebrate, or
said MCM8 consists of the amino acid sequence consisting of SEQ ID NO: 1 or 3 or any homologous MCM8 protein from vertebrate, and said MCM9 consists of the amino acid sequence consisting of SEQ ID NO: 2 or 4, or any homologous MCM9 protein from vertebrate.

Another advantageous embodiment of the invention relates to an isolated protein complex as defined above, wherein
said MCM8 consists of the amino acid sequence consisting of SEQ ID NO: 1, or a protein sequence substantially identical to SEQ ID NO: 1, and
said MCM9 consists of the amino acid sequence consisting of SEQ ID NO: 2, or a protein sequence substantially identical to SEQ ID NO: 2.

The invention also relates to the use of the protein complex previously defined, for the in vitro or in vivo homologous recombination or repair of nucleic acid molecules.

The inventors have demonstrated that the MCM8/MCM9 complex is important during meiosis, essentially during the formation of crossing-over.

The invention also relates to an isolated protein complex previously defined, for its use as medicine.

In the invention, the complex contains MCM8 and MCM9 proteins as defined above, or salts, in particular pharmaceutically acceptable salts, of MCM8 and MCM9 proteins.

The invention also relates to a composition, in particular a pharmaceutical composition comprising as active substance an isolated protein complex as defined above, in association with a pharmaceutically acceptable carrier.

The invention also relates to an isolated protein complex previously defined, for its use for the treatment of infertility or of damage of nucleic acid molecules.

The invention also relates to the use of an isolated complex as defined above, for the preparation of a medicament for the treatment of pathologies related to infertility.

Dosage of the active substance depends on the administration route, and can be easily determined by a skilled person. The pharmaceutical composition according to the invention can be administered by intravenous route, subcutaneous route, systemic route, or can be administered locally by infiltration, or per os.

The pharmaceutical composition according to the invention can be administered at a dosage from about 0.1 µg/kg/day to about 10 g/kg/day, according to the administration route.

In particular, the pharmaceutical compositions according to the invention may be administered at a dosage from about 2 to about 5 g/day in adults, or from about 50 mg to about 100 mg/kg/day for children.

Advantageous, unitary doses are from about 0.1 µg to about 10 g, and can be adjusted according to the galenical form of the composition.

The MCM8/MCM9 complex is implicated in human pathologies that show a reduced or an enhanced frequency of homologous recombination or of DNA damage repair and that affect or block fertility (Ataxia telangiectasia, Bloom's syndrome, Fanconi anemia, Werner syndrome, Rothmund-Thomson syndrome and others). Therefore, modulating the activity or presence of the MCM8/MCM9 complex constitutes not only ways to "modulate" fertility but also treats such human diseases.

An advantageous embodiment of the invention relates to an isolated protein complex as defined above, wherein said infertility is caused by reduction or absence of mature sexual cells.

Another advantageous embodiment of the invention relates to an isolated protein complex previously defined for its use as defined above, wherein infertility consists of oligospermia, azoospermia, teratospermia or necrospermia.

Another advantageous embodiment of the invention relates to an isolated protein complex previously defined for its use as defined above, wherein pathologies related to infertility belong to the group consisting of a reduction and an absence of ovum or the developmental block of ovum.

The invention relates to a composition comprising at least one nucleic acid molecule coding for the proteins that constitute the protein complex previously defined for its use for the treatment of infertility,
provided that said composition does not modify the germ line genetic identity of human beings, in particular when said animal is a human being.

An advantageous embodiment of the invention relates to a Composition as defined above, comprising a first nucleic acid molecule coding for the MCM8 protein and a second nucleic acid molecule coding for MCM9 protein, said MCM8 and MCM9 proteins constituting the protein complex according the definition mentioned above, for its use for the treatment of infertility
in particular provided that said composition does not modify the germ line genetic identity of human beings, in particular when said animal is a human being.

The invention also relates to the use of at least one compound inhibiting the formation and/or the stability or the activity of the complex as defined above, for inducing the animal sterility.

An advantageous embodiment of the invention relates to the use as defined above, provided that said compounds do not modify the germ line genetic identity of human being, in particular when said animal is a human being.

Advantageous composition comprises:
at least one antibody directed against MCM8 protein,
at least one antibody directed against MCM9 protein,
at least one siRNA directed against MCM8 protein,
at least one siRNA directed against MCM9 protein,
at least one shRNA directed against MCM8 protein,
at least one shRNA directed against MCM9 protein,
or a combination of the above.

Advantageous siRNA are
siRNA directed against MCM8, as set forth in SEQ ID NO: 13, SEQ ID NO: 14, SEQ ID NO: 15 and SEQ ID NO: 16, or
siRNA directed against MCM9, as set forth in SEQ ID NO: 17, SEQ ID NO: 18, SEQ ID NO: 19 and SEQ ID NO: 20.

Advantageous shRNA are
shRNA directed against MCM8, comprising one of the following sequence SEQ ID NO: 13, SEQ ID NO: 14, SEQ ID NO: 15 and SEQ ID NO: 16, and their respective complementary sequence or
shRNA directed against MCM9, comprising one of the following sequence in SEQ ID NO: 17, SEQ ID NO: 18, SEQ ID NO: 19 and SEQ ID NO: 20 and their respective complementary sequence.

The skilled person is able to determine the appropriate sequence of siRNA or shRNA that can be used, according to the species of the animal for which the complex MCM8/MC9 have to be destroyed.

An advantageous embodiment of the invention relates to the use according to the previous definition, wherein said compound is chosen among antibodies, small inhibiting RNA, small hairpin RNA and antisense nucleic acid molecule.

The invention also relates to a composition comprising:
either an isolated MCM9 proteins,
or nucleic acid molecules coding for said MCM9,
or compounds inhibiting the activity of said MCM9,
for its use for enhancing or reducing animal, preferably mammal, fertility,
in particular provided that said composition does not modify the germ line genetic identity of human beings, in particular when said animal is a human being.

The invention also relates to a composition comprising:
either an isolated MCM9 proteins,
or nucleic acid molecules coding for said MCM9,
for its use for enhancing animal, preferably mammal, fertility,
in particular provided that said composition does not modify the germ line genetic identity of human beings, in particular when said animal is a human being.

The invention also relates to a composition comprising compounds inhibiting the activity of MCM9, for its use for reducing animal, preferably mammal, fertility,
in particular provided that said composition does not modify the germ line genetic identity of human beings, in particular when said animal is a human being.

The invention also relates to the use of MCM9, for the in vitro homologous recombination or repair of nucleic acid molecules.

The invention will better illustrated by the following example and the following figures.

LEGEND TO THE FIGURE

FIGS. 1A-B: Strategy for the knock-outs of mouse MCM8 and MCM9 genes

FIG. 1A represents a schematic diagram of the targeting strategy for MCM8. Dark boxes labeled "E" depict exons. The location of the external probe used for southern blot analysis of the SpeI-digested targeted locus is also shown.

FIG. 1B represents a schematic diagram of the targeting strategy for MCM9. Dark boxes labeled "E" depict exons. The location of the external probe used for southern blot analysis of the SpeI-digested targeted locus is also shown.

FIGS. 2A-B: Characterization of the mouse-knock-outs for MCM8 and MCM9

FIG. 2A represents a Southern blot analysis of the targeted locus of MCM8. The WT allele (black arrow) yields a 5.4 kb band whereas the KO (white arrow) allele results in a band of 8.9 kb.

MW represents the molecular weight (in kilo bases (kb)); +/+ represents cells wherein both allele harbour undeleted MCM8 gene; +/− cells wherein one allele harbour a deleted MCM8 gene; −/− represents cells wherein both allele harbour deleted MCM8 gene. Lanes A, B, D, E, F and G, represent sample of mice resulting from the recombination, line C represents a positive control (wild type mouse).

FIG. 2B represents a Southern blot analysis of the targeted locus of MCM9. The WT allele (black arrow) yields a 13.1 kb band whereas the KO allele (white arrow) results in a band of 11.7 kb.

MW represents the molecular weight (in kilo bases (kb)); +/+ represents cells wherein both allele harbour undeleted MCM9 gene; +/− cells wherein one allele harbour a deleted MCM9 gene; −/− represents cells wherein both allele harbour deleted MCM9 gene. Lanes A-E represent sample of mice resulting from the recombination, line F represents a positive control (wild type mouse).

FIG. 3: Characterization of the mouse-knock-outs for MCM8 and MCM9—PCR method

FIG. 3 represents the PCR products of cDNA generated from mRNA extracted from WT- and MCM9-deficient testes as well as from MEF cells, amplifying a 2.4 kb fragment spanning from the beginning of exon 3 to exon 11, including the Walker A and B coding region. Shown is also the amplification of actin as a control (lower panels).

Lane A: PCR amplification product from WT testes DNA, Lane B PCR amplification product from MCM9-deficient testes DNA, Lane C: PCR amplification product from WT mouse embryonic fibroblasts (MEF) DNA, Lane D PCR amplification product from MCM9-deficient MEF DNA.

FIGS. 4A-B: Characterization of the mouse-knock-outs for MCM8 and MCM9—Western blot analysis FIG. 4A represents a Western blot analysis of testis extracts from WT- (Lane A), MCM8-deficient (Lane B) testes using the specific antibodies against MCM8. MCM8 protein is indicated by an arrow (93 kDa). A western blot for actin is shown as loading control (lower panel). kDa represent the molecular weight.

FIG. 4B represents a Western blot analysis of testis extracts from WT- (Lane A), MCM9-deficient (Lane B) testes using the specific antibodies against MCM9. MCM9 protein is indicated by an arrow (142 kDa) A western blot for actin is shown as loading control (lower panel). kDa represent the molecular weight.

FIG. 5: Characterization of the mouse-knock-outs for MCM8 and MCM9—Whole cell lysate analysis FIG. 5 represents a Western blot analysis of extracts from WT- (Lane A) and MCM9-deficient (Lane B) MEF cells of MCM9 (upper panel), Asfla and GAPDH (lower panel) as loading control.

FIGS. 6A-E: Histological analysis of gonads from MCM8- and MCM9-deficient mice.

FIGS. 7A-D: Histological analysis of newborn and 15 days post partum WT- and MCM8-deficient ovaries.

Figure 7A:
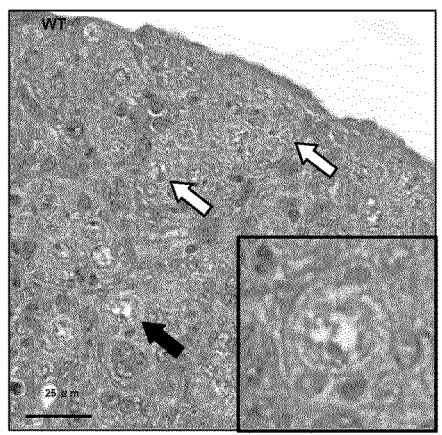

FIG. 7A represents HE-stained histological sections of ovaries of newborn WT-females. White arrows depict oocytes at dictate stage and black arrows depict primordial follicles. bar: 25 μm.

Figure 7B:
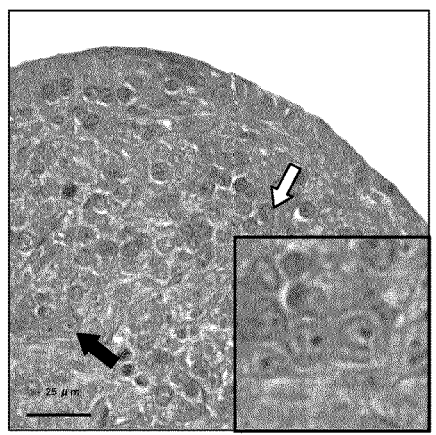

FIG. 7B represents HE-stained histological sections of ovaries of newborn MCM8 deficient females. White arrow indicates oocytes with condensed nuclei and black arrow highlights oocytes with condensed nuclei surrounded by granulocytes. Inlays depict primordial follicles. bar: 25 μm.

Figure 7C:
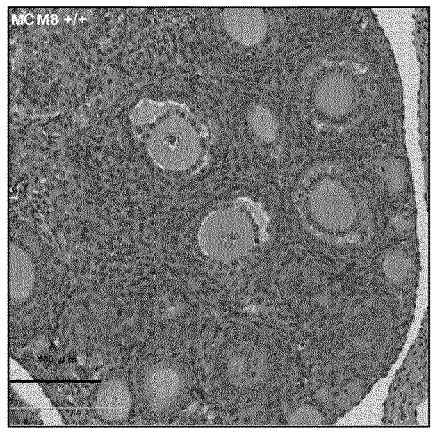

FIG. 7C represents HE-stained histological sections of ovaries of 15 days post partum WT-females. bar: 25 μm.

Figure 7D:

FIG. 7D represents HE-stained histological sections of ovaries of 15 days post partum MCM8 deficient females. bar: 25 μm.

FIGS. 8A-D: Photographs of testes.

Figure 8A:
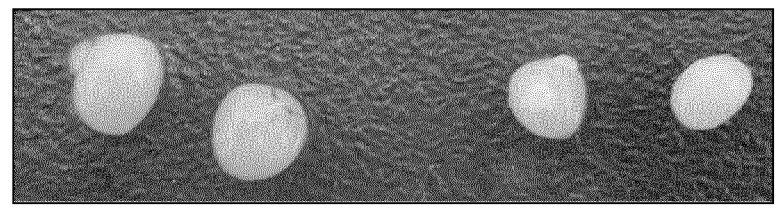

FIG. 8A represents photograph of testes of new born WT male (left) or of newborn MCM8 deficient male (right)

Figure 8B:
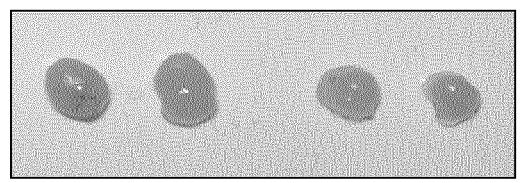

FIG. 8B represents photograph of testes of new born WT male (left) or of newborn MCM9 deficient male (right)

Figure 8C:
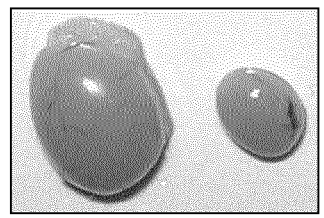

FIG. 8C represents photograph of testes of adult WT male (left) or of adult MCM8 deficient male (right).

Figure 8D:
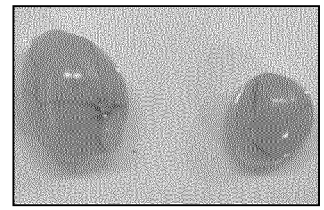

FIG. 8D represents photograph of testes of adult WT male (left) or of adult MCM9 deficient male (right).

Figure 9A:
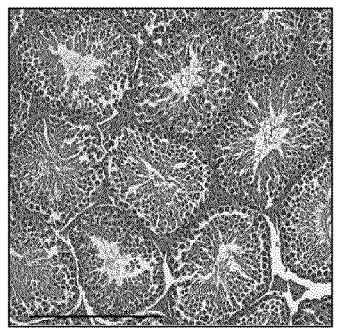
Figure 9B:
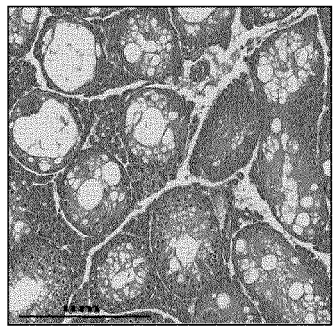
Figure 9C:
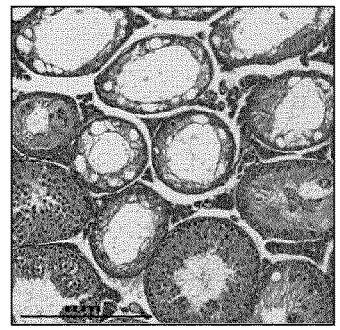

FIGS. 9A-C: Histological section of seminiferous tubule.

FIG. 9A represents HE-stained histological sections of testes from WT adult males. Seminiferous tubules are observable. bar: 250 μm.

FIG. 9B represents HE-stained histological sections of testes from MCM8 deficient adult males. Seminiferous tubules are observable. bar: 250 μm.

FIG. 9C represents HE-stained histological sections of testes from MCM9 deficient adult males. Seminiferous tubules are observable. bar: 250 μm.

FIGS. 10A-E: Histological section of tubules.

Figure 10A:
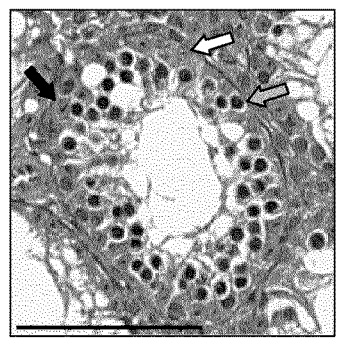

FIG. 10A represents HE-stained example of MCM8-deficient tubule that contains spermatogonia (white arrow) and also spermatocytes in leptonema/zygonema or that contain either only spermatogonia and sertoli cells (black arrows), Grey arrow depicts an eosin-dense stained (apoptotic) spermatocyte.

Figure 10B:
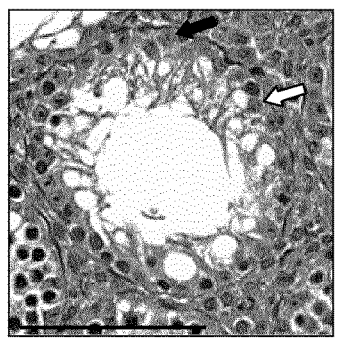

FIG. 10B represents HE-stained example of MCM8-d efficient tubule that contains spermatogonia (white arrow) and also spermatocytes in leptonema/zygonema or that contain either only spermatogonia and sertoli cells (black arrows).

Figure 10C:
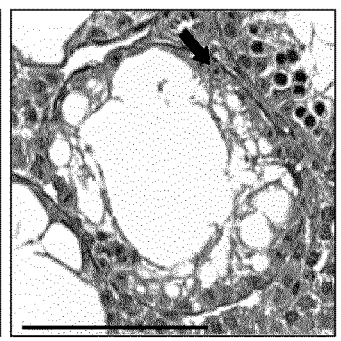

FIG. 10C represents HE-stained example of MCM8-deficient tubule that is even devoid of spermatogonia and expose a sertoli cell only phenotype.

Figure 10D:
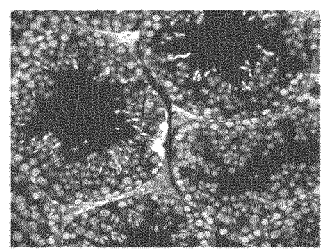

FIG. 10D represents TUNEL staining of testes section from control male mice

Figure 10E:
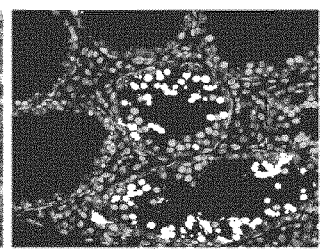

FIG. 10E represents TUNEL staining of testes section from MCM8-deficient male mice.

FIG. 11A-H: MCM8-deficient spermatocytes are blocked in meiotic prophase I Shown are nuclei in leptonema.

Figure 11:
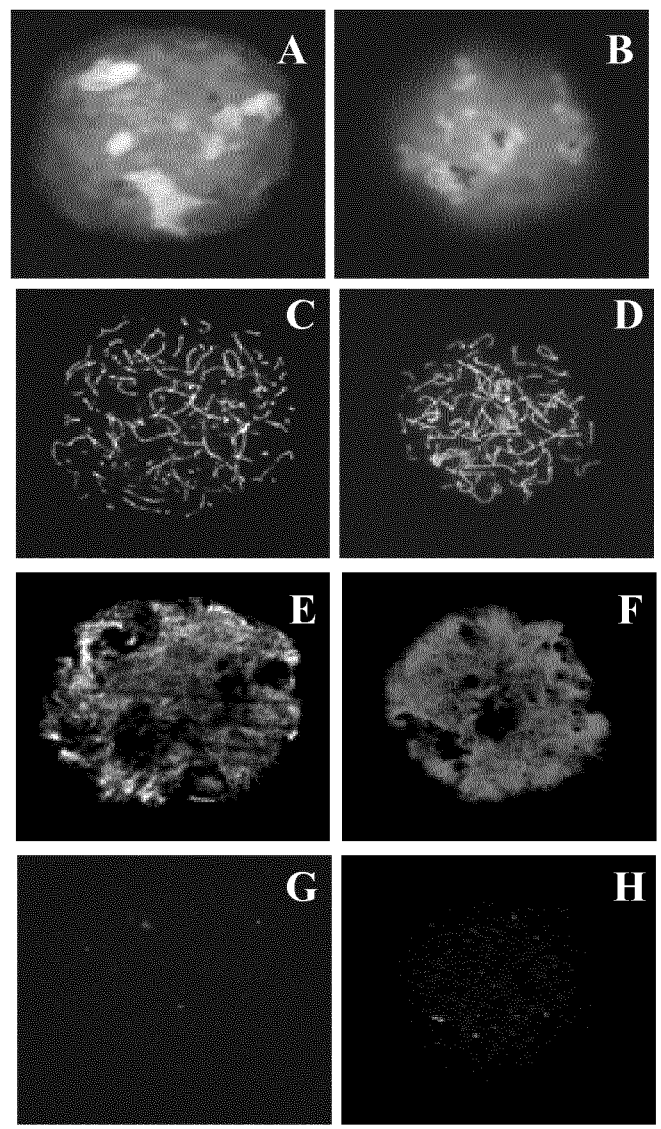

FIG. 11A represents a representative immunofluorescence of surface spreads from WT testes that were stained against DNA.

FIG. 11B represents a representative immunofluorescence of surface spreads from MCM8-deficient testes that were stained against DNA.

FIG. 11C represents a representative immunofluorescence of surface spreads from WT testes that were stained against SYCP3.

FIG. 11D represents a representative immunofluorescence of surface spreads from MCM8-deficient testes that were stained against SYCP3.

FIG. 11E represents a representative immunofluorescence of surface spreads from WT testes that were stained against γ-H2AX.

FIG. 11F represents a representative immunofluorescence of surface spreads from MCM8-deficient testes that were stained against γ-H2AX.

FIG. 11G represents a representative immunofluorescence of surface spreads from WT testes that were stained against SYCP1.

FIG. 11H represents a representative immunofluorescence of surface spreads from MCM8-deficient testes that were stained against SYCP1.

FIG. 12A-H: MCM8-deficient spermatocytes are blocked in meiotic prophase I Shown are nuclei in zygonema.

Figure 12:
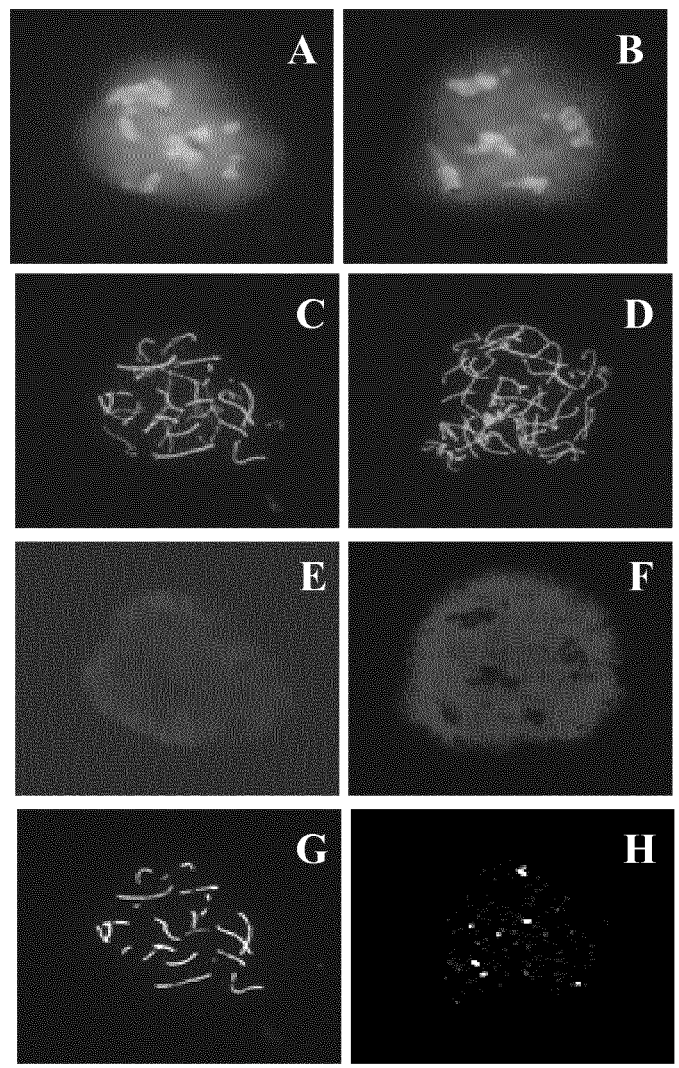

FIG. 12A represents a representative immunofluorescence of surface spreads from WT testes that were stained against DNA.

FIG. 12B represents a representative immunofluorescence of surface spreads from MCM8-deficient testes that were stained against DNA.

FIG. 12C represents a representative immunofluorescence of surface spreads from WT testes that were stained against SYCP3.

FIG. 12D represents a representative immunofluorescence of surface spreads from MCM8-deficient testes that were stained against SYCP3.

FIG. 12E represents a representative immunofluorescence of surface spreads from WT testes that were stained against γ-H2AX.

FIG. 12F represents a representative immunofluorescence of surface spreads from MCM8-deficient testes that were stained against γ-H2AX.

FIG. 12G represents a representative immunofluorescence of surface spreads from WT testes that were stained against SYCP 1.

FIG. 12H represents a representative immunofluorescence of surface spreads from MCM8-deficient testes that were stained against SYCP1.

FIGS. 13A-J: Co-localisation of SYCP1 and SYCP3.

Figure 13:
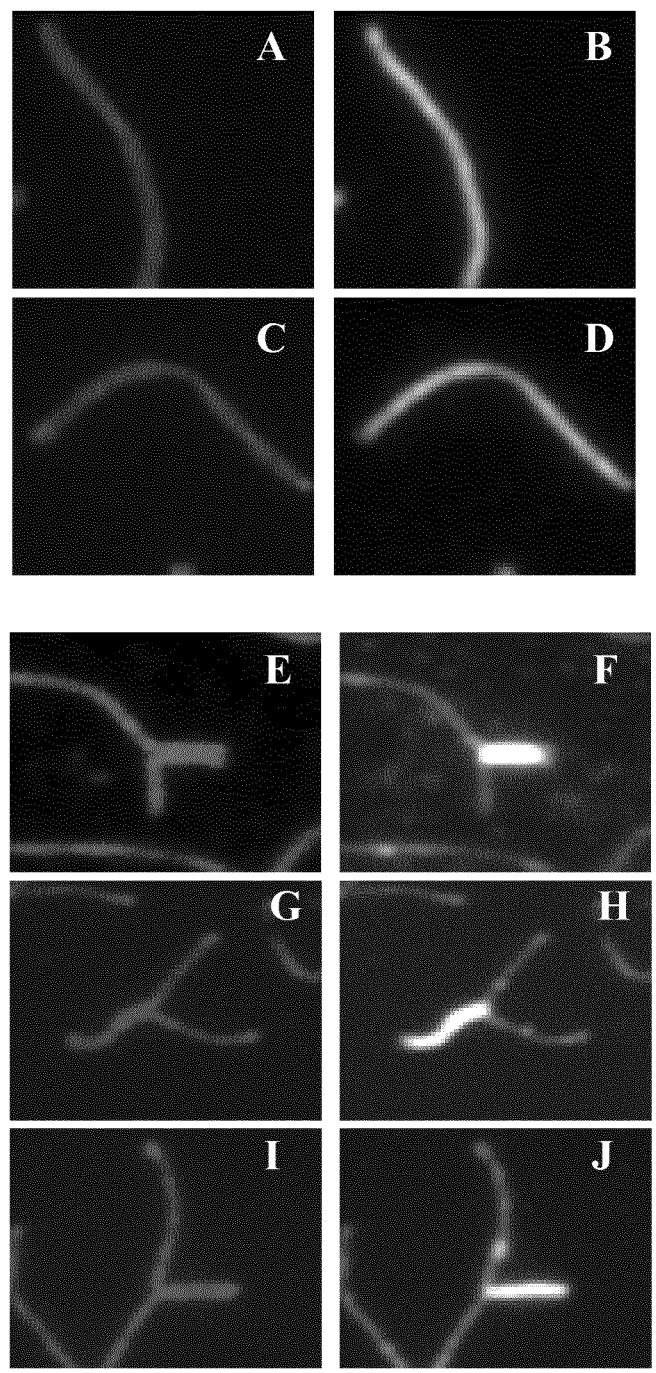

FIGS. 13 A and C represent immunofluorescence of DNA of WT testes labelled with anti SYCP3 antibody.

FIGS. 13 B and D represent immunofluorescence of DNA of WT testes labelled with anti SYCP1 and SYCP3 antibodies. The co-localisation is shown.

FIGS. 13 E, G and I represent immunofluorescence of DNA of MCM8 deficient testes labelled with anti SYCP3 antibody.

FIGS. 13 F, H and J represent immunofluorescence of DNA of MCM8 deficient testes labelled with anti SYCP1 and SYCP3 antibodies. The co-localisation of SYCP1 and SYCP3 is shown.

FIGS. 14A-F show a representative SYCP3- and DMC1-stainings in WT- and MCM8-deficient nuclei in leptonema.

Figure 14:
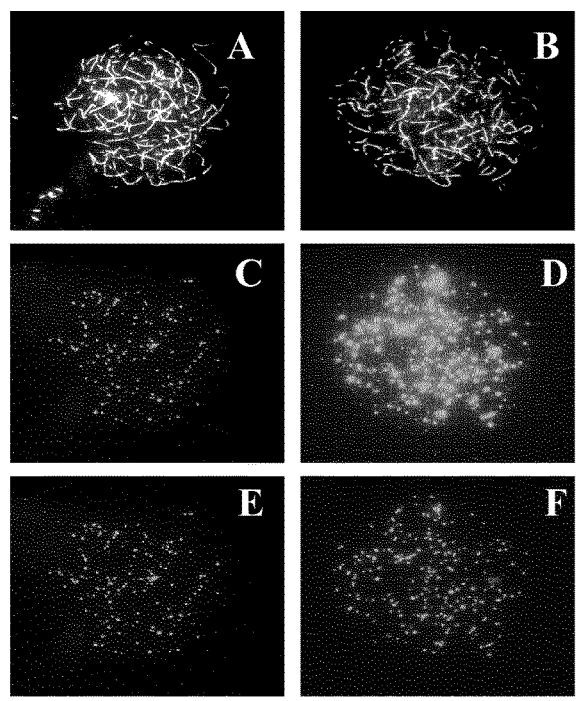

FIG. 14 A represents SYCP3 staining in WT nuclei.

FIG. 14 B represents SYCP3 staining in MCM8 deficient nuclei.

FIGS. 14C and E represent DMC1 staining in WT nuclei.

FIGS. 14 B and F represent DMC1 staining in MCM8 deficient nuclei.

Two exposures of the DMC1 signal from the MCM8-deficient nucleus, first an equal exposure for WT and KO nuclei (14C and 14D) and secondly an exposure of the KO nucleus that was adjusted to visualize best individual foci (14E and 14F).

Figure 15A:
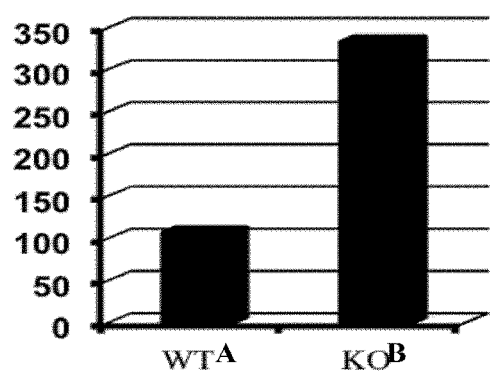
Figure 15B:
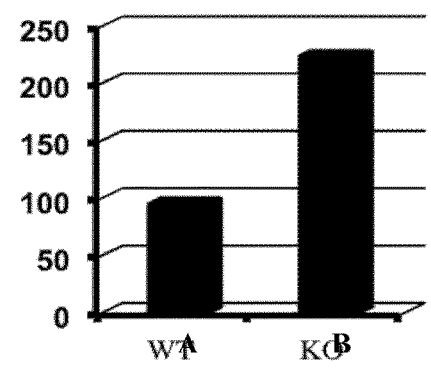

FIGS. 15A-B: Average number of DMC1-foci in WT- and MCM8-deficient spermatocytes in leptonema and zygonema.

Y-axis represents the number of DCM1 foci per nucleus.

FIG. 15A represents a graph showing the average number of DMC1-foci in WT-(A) and MCM8-deficient (B) spermatocytes in leptonema.

FIG. 15B represents a graph showing the average number of DMC1-foci in WT-(A) and MCM8-deficient (B) spermatocytes in zygonema.

Figure 16A:
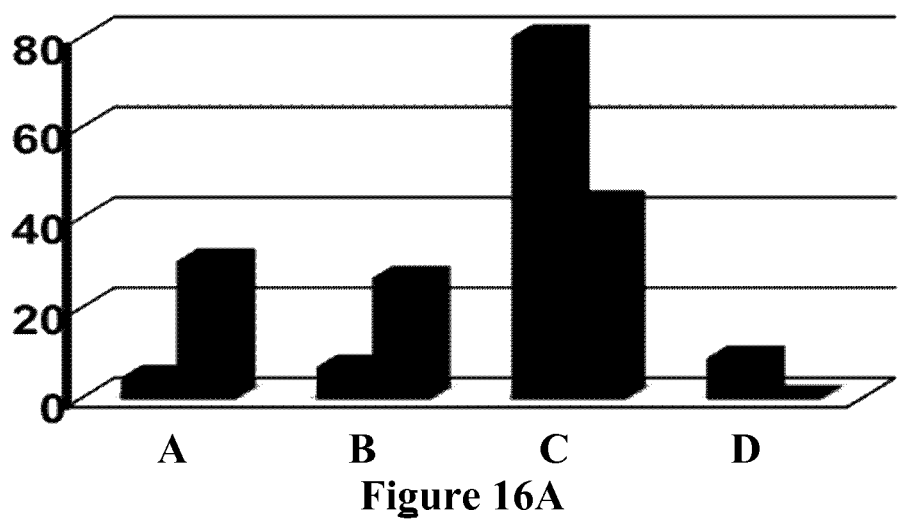
Figure 16B:
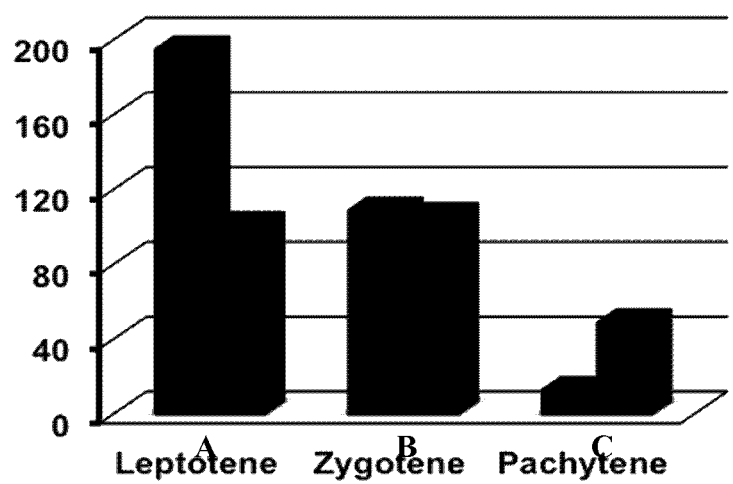

FIGS. 16A-B: Statistical analysis of the percentages of meiotic cells in leptonema, zygonema, pachynema and diplonema stage from control- and MCM9-deficient testes at 15 days post partum.

Dark grey column represents WT-testes, light grey column represents MCM9-deficient testes.

FIG. 16A represents a graph showing the percentage of spermatides in leptonema (A), zygonema (B), pachynema (C) and diplonema (D) stage.

FIG. 16B represents a graph showing the number of DMC1-foci per nucleus in leptonema (A), zygonema (B) and pachynema (C) stage.

FIGS. 17A-J: WT- and MCM9-deficient spermatocytes in diplonema

Figure 17:
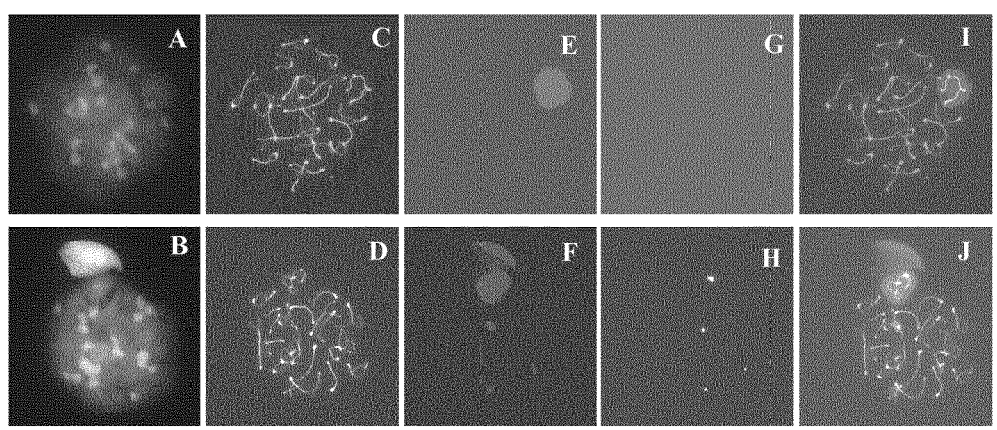

FIG. 17A is a representative example of WT-spermatocytes in diplonema stage stained for DNA.

FIG. 17B is a representative example of MCM9-deficient spermatocytes in diplonema stage stained for DNA.

FIG. 17C is a representative example of WT-spermatocytes in diplonema stage stained for SYCP3.

FIG. 17D is a representative example of MCM9-deficient spermatocytes in diplonema stage stained for SYCP3.

FIG. 17E is a representative example of WT-spermatocytes in diplonema stage stained for RPA.

FIG. 17F is a representative example of MCM9-deficient spermatocytes in diplonema stage stained for RPA.

FIG. 17G is a representative example of WT-spermatocytes in diplonema stage stained for γ-H2AX.

FIG. 17H is a representative example of MCM9-deficient spermatocytes in diplonema stage stained for γ-H2AX.

FIG. 17I is a representative example of WT-spermatocytes in diplonema stage, in which the staining for DNA, SYCP3, RPA and γ-H2AX are merged.

FIG. 17J is a representative example of MCM9-deficient spermatocytes in diplonema stage in which the staining for DNA, SYCP3, RPA and γ-H2AX are merged.

Figure 18A:
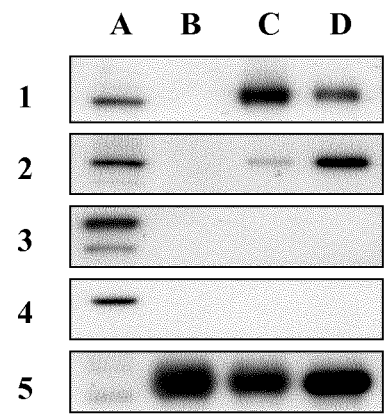
Figure 18B:
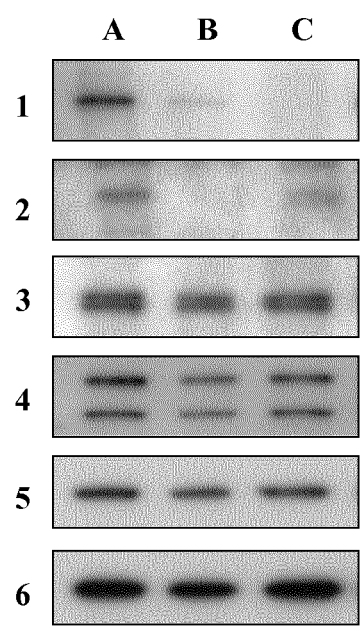
Figure 18C:
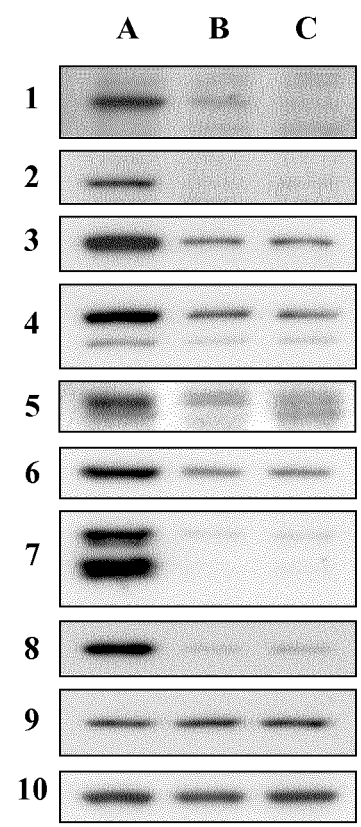

FIGS. 18A-C: MCM8 and MCM9 form a complex and KO MEF cells expose a growth defect, micronuclei and chromosome breaks FIG. 18A represents immunoprecipitations of MCM8 (IP anti-MCM8; lane C) and MCM9 (IP anti-MCM9; lane D) from testes extracts blotted against MCM9 (panel 1), MCM8 (panel 2), MCM2 (panel 3) and MCM5 (panel 4). To normalize the loading, IgGs of each IP are also shown (panel 5).

Lane A correspond to a cell extract, Lane B correspond to the immunoprecipitation with non relevant antibody FIG. 18B represents a western blot showing the interdependent protein stability of MCM8 and MCM9 in WT-(lane A), MCM8-deficient (lane B) and MCM9-deficient (lane C) MEF cell extracts blotted against MCM9 (panel 1), MCM8 (panel 2), MCM5 (panel 3), MCM2 (panel 4), and MCM7 (panel 5). To normalize the loading, GAPDH expression is also shown (panel 6).

FIG. 18C represents a western blot showing the interdependent protein stability of MCM8 and MCM9 in WT-(lane A), MCM8-deficient (lane B) and MCM9-deficient (lane C) testes extracts blotted against MCM9 (panel 1), MCM8 (panel 2), MCM5 (panel 3), MCM2 (panel 4), Cdtl (panel 5), PCNA (panel 6), SYCP3 (panel 7) and Rad51 (panel 8). To normalize the loading, GAPDH and actin expression are also shown (panels 9 and 10, respectively).

Figure 19A:
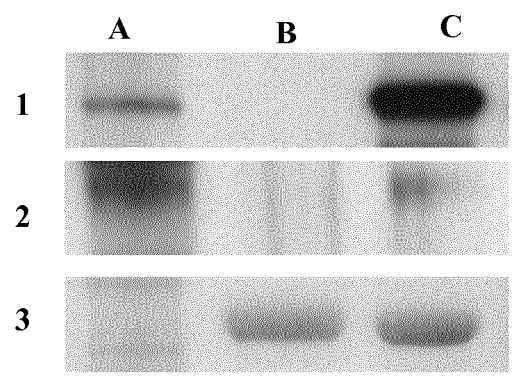
Figure 19B:
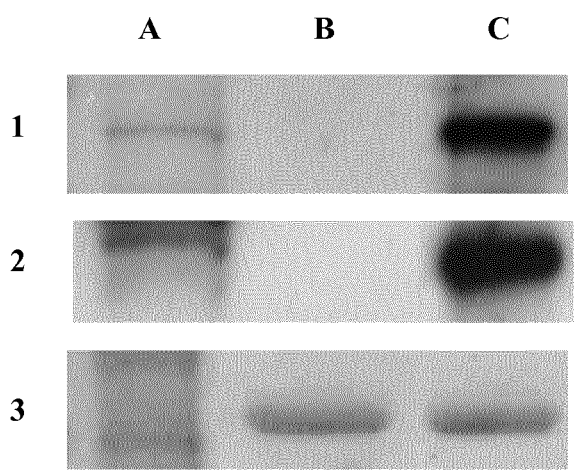
Figure 19C:
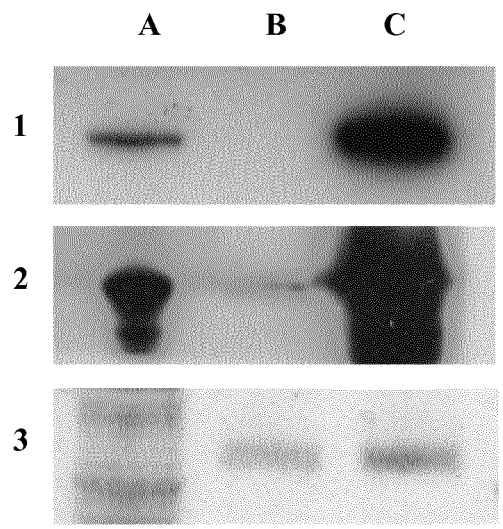

FIGS. 19A-C: Immunoprecipitation of the MCM8/MCM9 complex

FIG. 19 A represents a western blot analysis of the immunoprecipitation of MCM9 (lane C) from Hela cell extracts, with anti MCM9 (panel 1) and anti MCM8 (panel 2). To normalize the loading, IgGs of each IP are also shown (panel 3).

Lane A corresponds to the input, and lane B corresponds to the immunoprecipitation with non relevant antibodies.

FIG. 19 B represents a western blot analysis of the immunoprecipitation of MCM9 (lane C) from Hela S3 cell extracts transfected with MCM8 and Ha-MCM9 proteins, with anti Ha (panel 1) and anti MCM8 (panel 2). To normalize the loading, IgGs of each IP are also shown (panel 3).

Lane A corresponds to the input, and lane B corresponds to the immunoprecipitation with non relevant antibodies.

FIG. 19 C represents a western blot analysis of the immunoprecipitation of MCM9 (lane C) from U2OS cell extracts transfected with MCM8 and Ha-MCM9 proteins, with anti Ha (panel 1) and anti MCM8 (panel 2). To normalize the loading, IgGs of each IP are also shown (panel 3).

Lane A corresponds to the input, and lane B corresponds to the immunoprecipitation with non relevant antibodies.

Figure 19D:
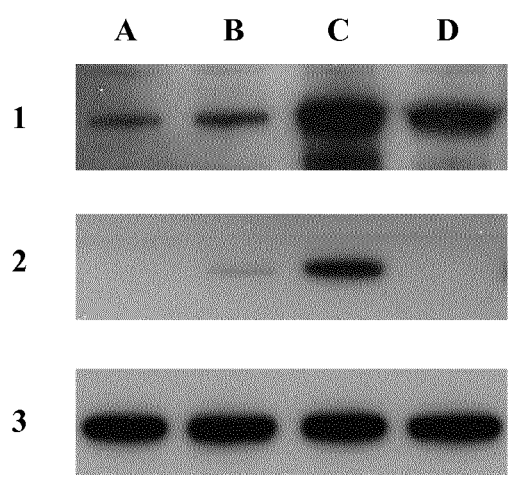

FIG. 19D represents a western blot (WB) of U2OS cells transfected with pcDNA3-FLAG-MCM8 (Lane B), pcDNA3-MCM9 (Lane D), pcDNA3-FLAG-MCM8 and pcDNA3-MCM9 (lane C) or only with pcDNA3 empty vector for the Mock condition (lane A). Cells were lysed in a lysis buffer (50 mM Tris-HCl pH 7.5, 100 mM NaCl, 5 mM EDTA, 1% Triton X-100, phosphatase and protease inhibitors) and 20 μg per lane of total lysate was used for WB. WB was performed using anti-MCM9 (panel 1), anti-FLAG (panel 2) and anti-Tubulin (Mouse, SIGMA; panel 3) antibodies for the loading control.

Figure 19E:
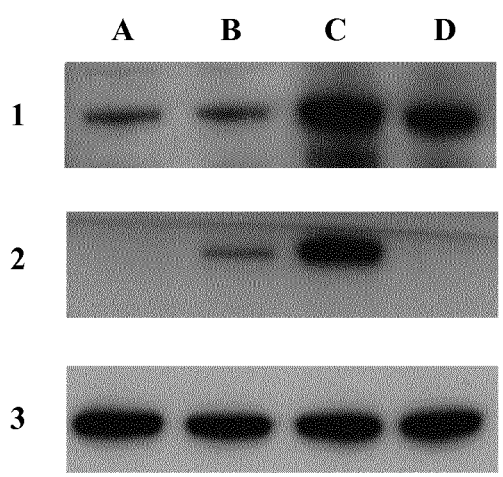

FIG. 19E represents a western blot (WB) of U2OS cells were transfected with pcDNA3-HA-MCM8 (lane B), pcDNA3-MCM9 (lane D), with pcDNA3-HA-MCM8 and/ pcDNA3-MCM9 (lane C) or only with pcDNA3 empty vector for the Mock condition (lane A). Cells were lysed in a lysis buffer (50 mM Tris-HCl pH 7.5, 100 mM NaCl, 5 mM EDTA, 1% Triton X-100, phosphatase and protease inhibitors) and 20 μg per lane of total lysate was used for WB. WB was performed using anti-MCM9 (panel 1), anti-HA (panel 2) and anti-Tubulin (Mouse, SIGMA; panel 3) antibodies for the loading control.

Figure 20:
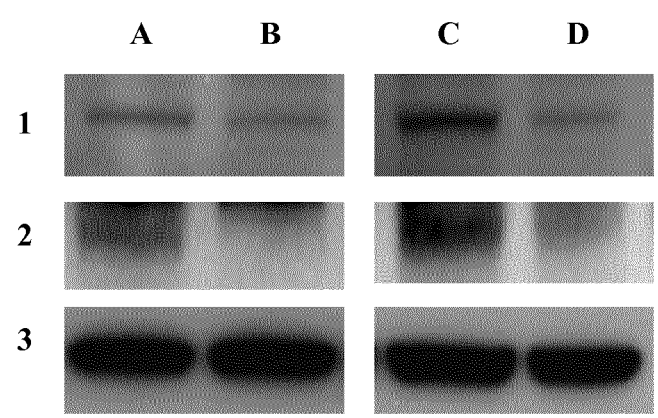

FIG. 20: Stabilisation of the complex

FIG. 20 represents the expression of MCM9 (panel 1) or MCM8 (panel 2) in cells treated with non relevant siRNA (lane A and C), or treated with siRNA ant MCM8 (lane B) or anti MCM9 (lane D). To normalize the loading, Tubulin expression is also shown (panel 3)

Figure 21A:
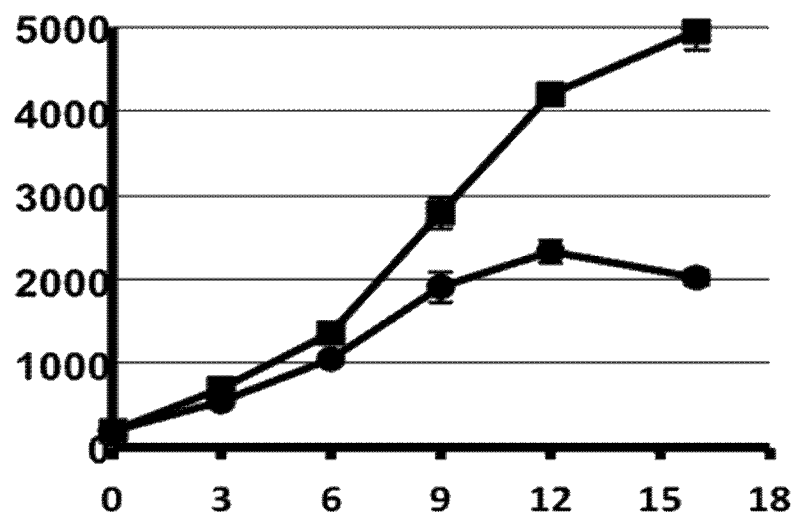
Figure 21B:
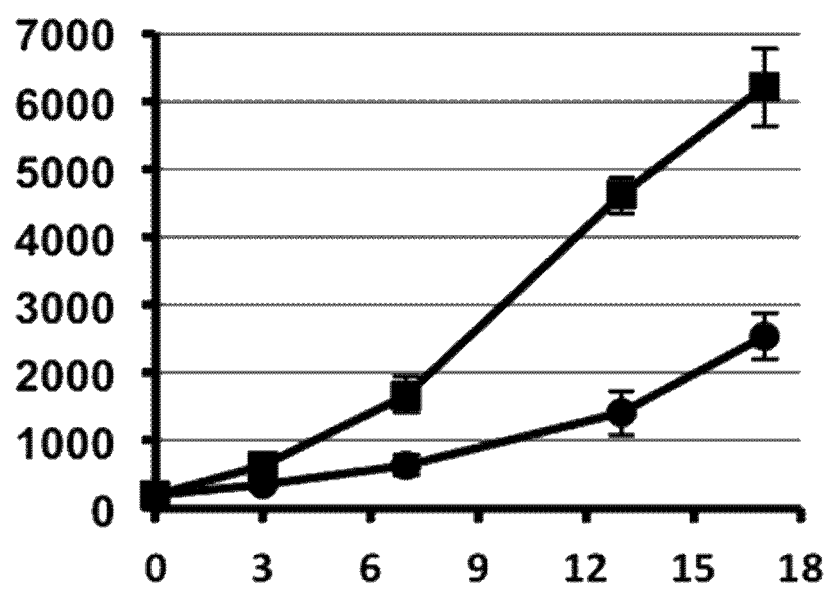

FIG. 21A-B Growth curves of WT- and KO MEF cell couples from same litters.

Y-axis represents the cell number×$10^3$, X axis represents the time in days.

FIG. 21A represents the cell growth of WT MEF cells (curve with squares) and the growth of MCM8 deficient MEF cells (curve with circles).

FIG. 21B represents the cell growth of WT MEF cells (curve with squares) and the growth of MCM9 deficient MEF cells (curve with circles).

FIGS. 22A-C: Cell cycle analysis.

FIG. 22A represents a flow cytometry analysis of the DNA content of exponentially growing WT MEF cells, DNA being labelled with Propidium iodine (PI).

FIG. 22B represents a flow cytometry analysis of the DNA content of exponentially growing MCM8-deficient MEF cells, DNA being labelled with Propidium iodine (PI).

FIG. 22C represents a flow cytometry analysis of the DNA content of exponentially growing WT MEF cells, DNA being labelled with Propidium iodine (PI).

FIG. 22D represents a flow cytometry analysis of the DNA content of exponentially growing MCM9-deficient MEF cells, DNA being labelled with Propidium iodine (PI).

FIGS. 23A-C: Representative examples of nuclei

Figure 23:
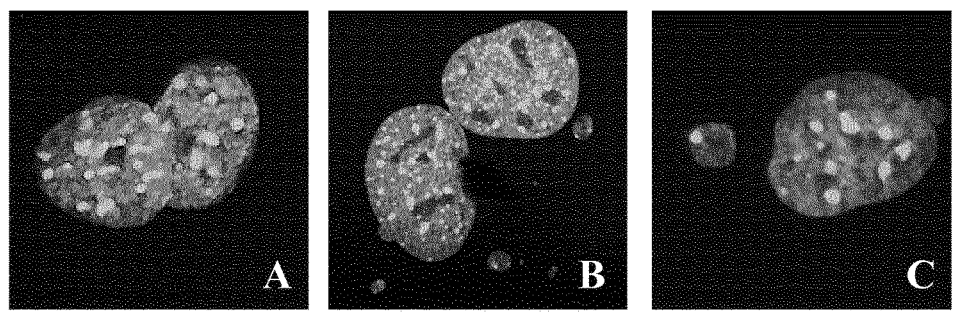

FIG. 23 A represents nuclei from WT-MEF cells in which DNA is labelled.

FIG. 23 B represents nuclei from MCM8 deficient MEF cells in which DNA is labelled.

FIG. 23 C represents nuclei from MCM9 deficient MEF cells in which DNA is labelled.

Figure 24:
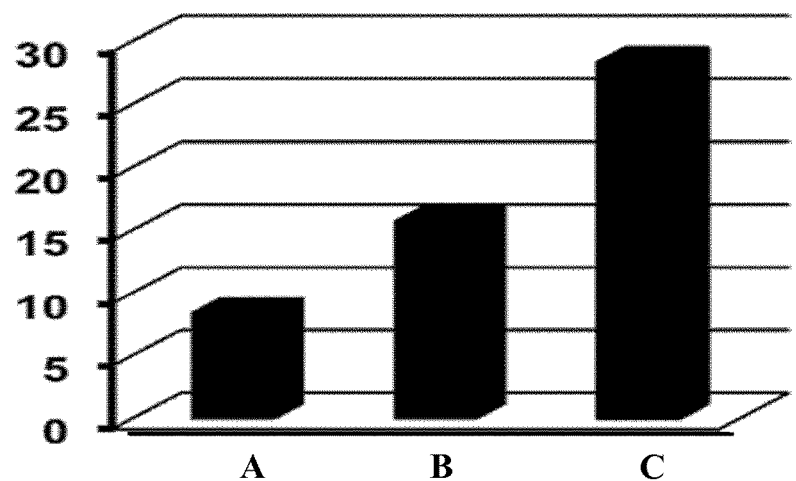

FIG. 24 represents a graph showing the percentage of cells with micronuclei, in WT MEF cells (A), MCM8-(B), or MCM9-deficient MEF cells (C)

Figure 25:
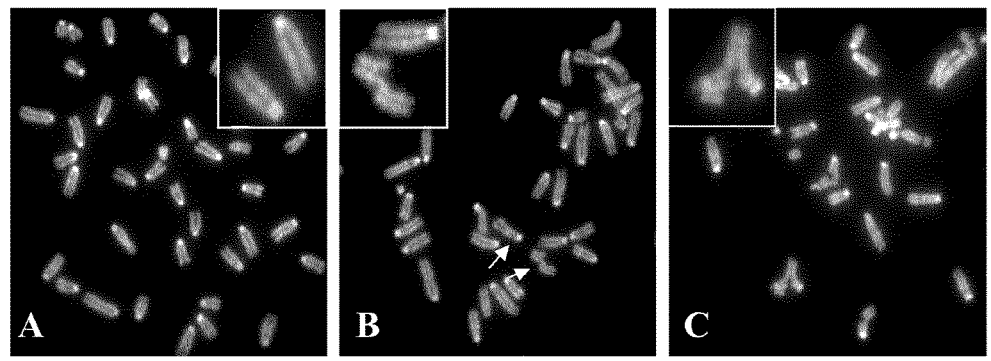

FIGS. 25 A-C: Images of metaphase spread from control- and KO MEF cells.

FIG. 25A represents image of metaphase spread from WT MEF cells

FIG. 25B represents image of metaphase spread from MCM8-deficient MEF cells

FIG. 25C represents image of metaphase spread from MCM9 deficient MEF cells

Figure 26:
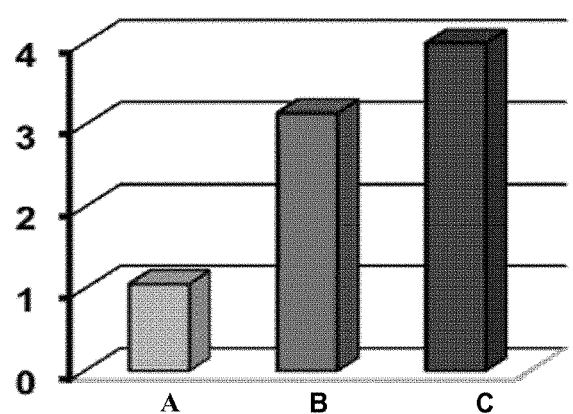

FIG. 26 represents a graph showing the percentages of broken chromosomes observed in metaphase spreads from WT-(A), MCM8-(B) and MCM9-deficient cells (C).

FIG. 27 represents a graph showing the multiplication of WT (curve with squares) or MCM8 deficient cells (curve with circles). Y axis represents the cell number×$10^3$, and X-axis le time in days.

FIG. 28 A-H: Immortalisation

FIG. 28A represents WT MEF cells after 40 days in culture.

FIG. 28B represents MCM8-deficient MEF cells after 40 days in culture.

FIGS. 28C and 28D represent confluent WT MEF cells.

FIGS. 28E and 28F represents confluent MCM8-deficient MEF cells.

FIG. 28G is a plate seeded with WT MEF cells.

FIG. 28H is a plate seeded with MCM8-deficient MEF cells, in which colonies are observable.

Figure 29:
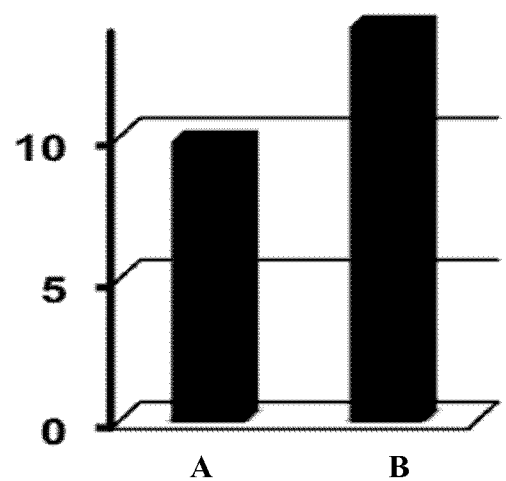

FIG. 29 is a graph representing the percentages of collapsed forks in WT-(A) and MCM9-(B) deficient MEF cells.

Figure 30:
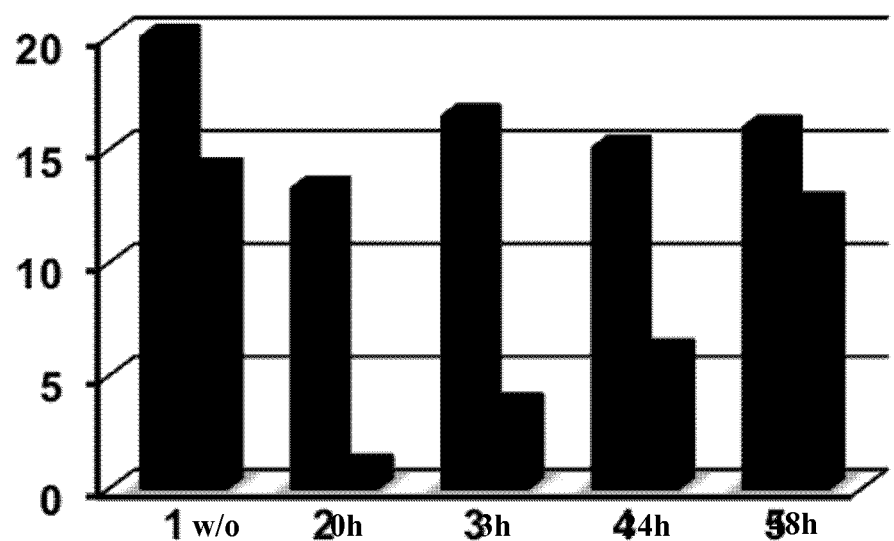

FIG. 30 is a graph representing the percentages of Bromo deoxyuridine (BrdU)-positive control-(light grey column) and MCM9-deficient (dark grey column) cells before (w/o), at the end (0 h) and at indicated time points after release from APH.

FIGS. 31A-T

Figure 31:
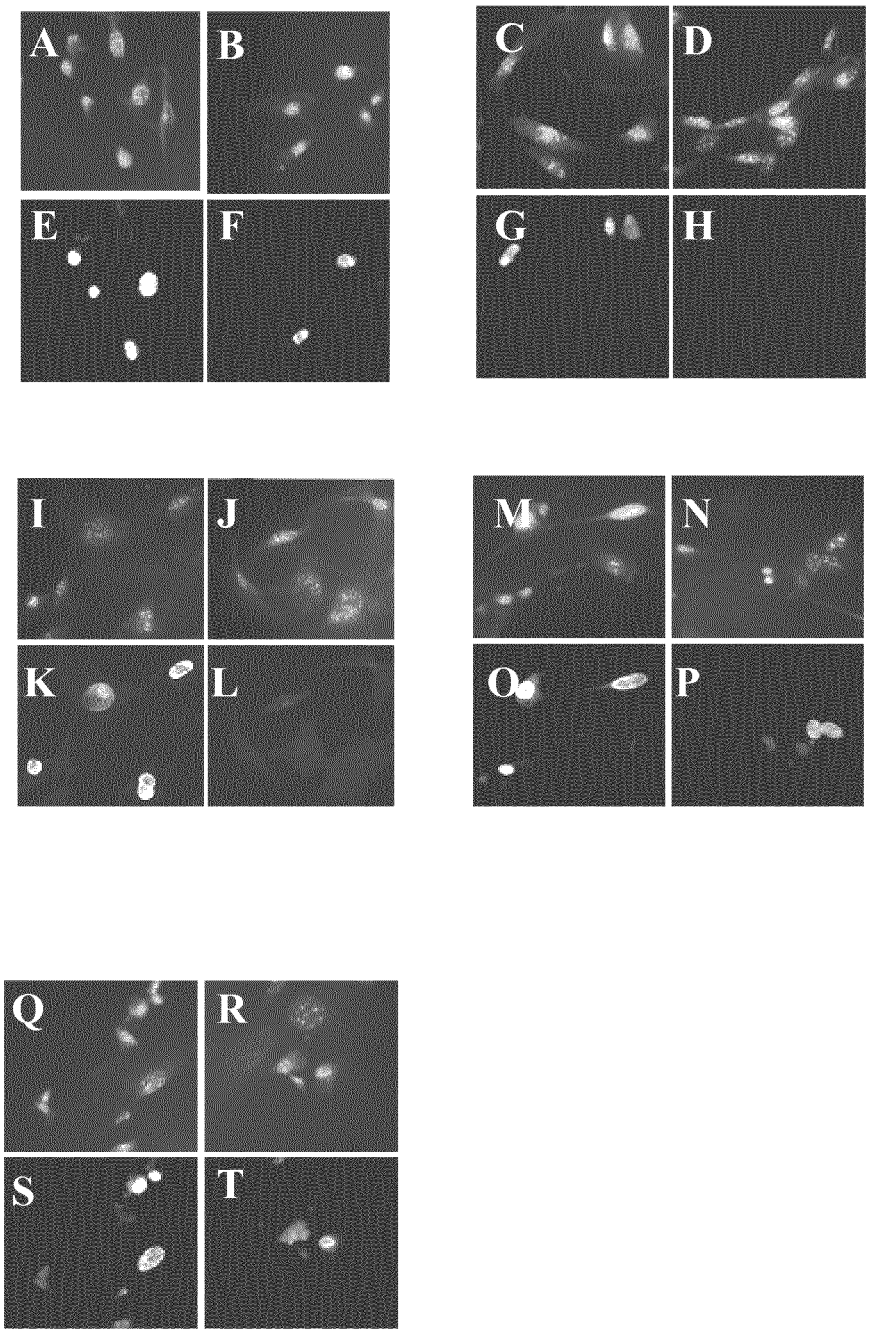

FIG. 31A represents WT nuclei stained for DNA before release of APH.

FIG. 31B represents MCM9-deficient nuclei stained for DNA before release of APH.

FIG. 31C represents WT nuclei stained for BrdU before release of APH.

FIG. 31D represents MCM9-deficient nuclei stained for BrdU before release of APH.

FIG. 31E represents WT nuclei stained for DNA at t0.

FIG. 31F represents MCM9-deficient nuclei stained for DNA at t0.

FIG. 31G represents WT nuclei stained for BrdU at t0.

FIG. 31H represents MCM9-deficient nuclei stained for BrdU at t 0 h.

FIG. 31I represents WT nuclei stained for DNA at t 3 h.

FIG. 31J represents MCM9-deficient nuclei stained for DNA at t 3 h.

FIG. 31K represents WT nuclei stained for BrdU at t 3 h.

FIG. 31L represents MCM9-deficient nuclei stained for BrdU at t 3 h.

FIG. 31M represents WT nuclei stained for DNA at t 24 h.

FIG. 31N represents MCM9-deficient nuclei stained for DNA at t 24 h.

FIG. 31O represents WT nuclei stained for BrdU at t 24 h.

FIG. 31P represents MCM9-deficient nuclei stained for BrdU at t 24 h.

FIG. 31Q represents WT nuclei stained for DNA at t 48 h.

FIG. 31R represents MCM9-deficient nuclei stained for DNA at t 48 h.

FIG. 31S represents WT nuclei stained for BrdU at t 48 h.

FIG. 31T represents MCM9-deficient nuclei stained for BrdU at t 48 h.

Figure 32A:
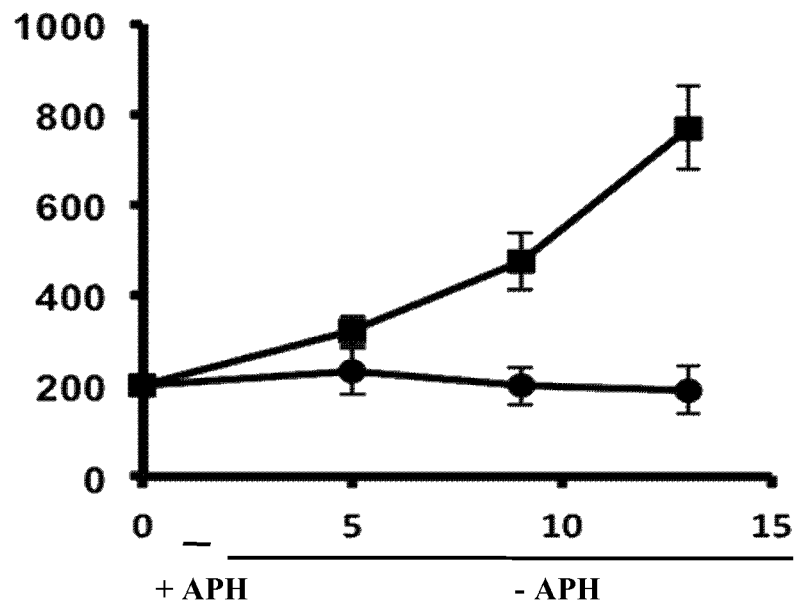

FIG. 32A represents growth curves of WT (curve with squares) and MCM8-deficient MEF cells (curve with circles) treated for 24 h with APH and then released without drug. X-axis represents time in days, Y axis represents cell number×$10^3$.

Figure 32B:
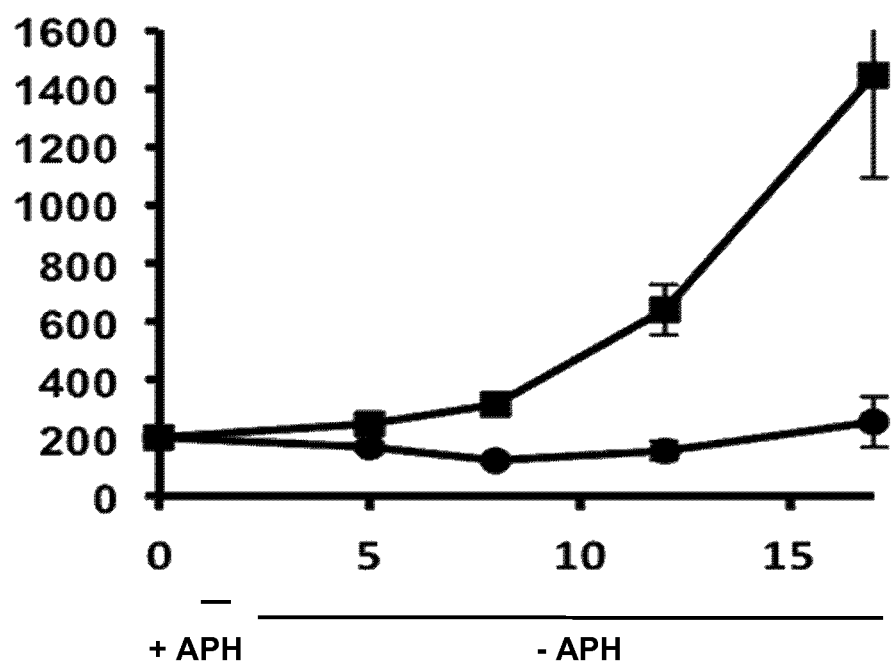

FIG. 32B represents growth curves of WT (curve with squares) and MCM9-deficient MEF cells (curve with circles) treated for 24 h with APH and then released without drug. X-axis represents time in days, Y axis represents cell number×$10^3$.

Figure 33:
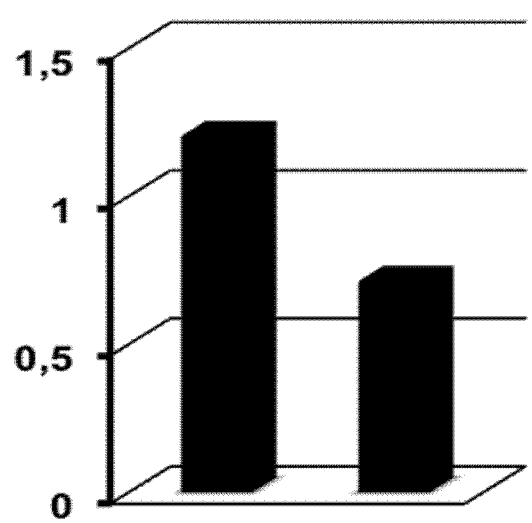

FIG. 33 represent a graph showing the quotient of replication origin distance in MCM9 deficient cells divided by WT cells. Light grey column represents the results without APH and dark grey column represents the results in the presence of APH.

Figure 34A:
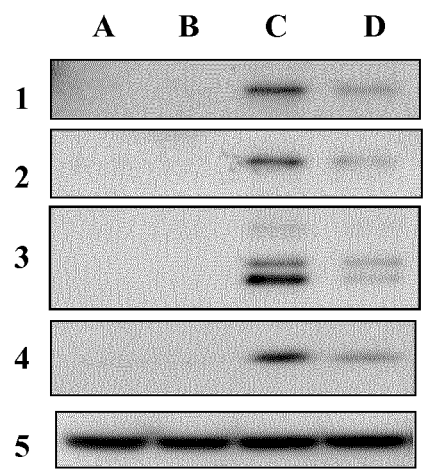
Figure 34B:
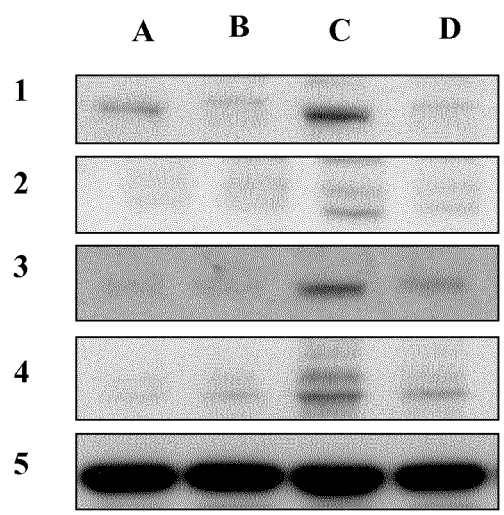

FIG. 34A-B: The MCM8/9 complex is overexpressed upon fork block and its absence cause recruiting defects of the HR-mediated DSB repair machinery FIG. 34A represents a western blot analysis of chromatin fractions of WT-(lanes A and C) and MCM9-deficient-(lanes B and D) MEF cells exposed (lanes C and D) or not (lanes A and B) for 24 h to APH for Rad51 (panel 1), Mre11 (panel 2), RPA32 (panel 3), γ-H2AX (panel 4) and H3 (panel 5) as loading control.

FIG. 34B represents a western blot analysis of WT-(lanes A and C) and MCM9-deficient-(lanes B and D) MEF cells exposed (lanes C and D) or not (lanes A and B) for 24 h to APH for MCM9 (panel 1), MCM8 (panel 2), Chk1-P (panel 3), Chk2 (panel 4) and GAPDH (panel 5) as loading control.

Figure 35:
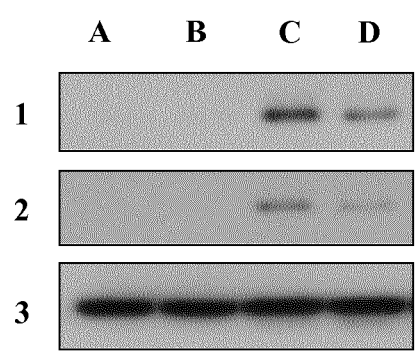

FIG. 35 represents a western blot analysis of chromatin fractions of WT-(lanes A and C) and MCM8-deficient-(lanes B and D) MEF cells exposed (lanes C and D) or not (lanes A and B) for 24 h to APH for Rad51 (panel 1), γ-H2AX (panel 2) and H3 (panel 3) as loading control.

EXAMPLE

Introduction

The Inventors generated mouse knock-out models of both MCM8 and MCM9 and found that both MCM8- and MCM9 deficient mice are viable, but sterile. Both knock-out animals have gonads of strongly reduced size. MCM8-deficient ovaries exhibit an early block of follicle development and, in MCM8-deficient testes, seminiferous tubules become apoptotic and spermatocytes fail to synapse homologous chromosomes. MCM9-deficient ovaries are completely devoid of oocytes and only few seminiferous tubules are functional and contain meiotic cells in testes. The Inventors show that the block in gametogenesis is due to persistent DNA damage in meiotic prophase I and failure to repair DSB by homologous recombination.

Both MCM8- and MCM9-deficient MEF cells survive, but are genetically instable, accumulating micronuclei, chromosomes breaks and a propensity to immortalize and to transform. Knock-out cells are defective in replication fork maintenance, dormant origin activation and die under mild fork blocking conditions. These cells are unable to activate properly HR-mediated fork-rescue and DSB repair mechanisms and exhibit a defect in checkpoint signalling. The rather similar phenotypes of both knock-outs is emphasized by the finding that MCM8 and MCM9 form a complex in vivo and that the stability of each protein is dependent on the presence of the other partner.

The Inventors studies reveal an essential role of MCM8 and MCM9 in the regulation of homologous recombination during both gametogenesis and mitotic DNA replication fork maintenance, DSB repair and genome stability.

Results

Figure 1A:
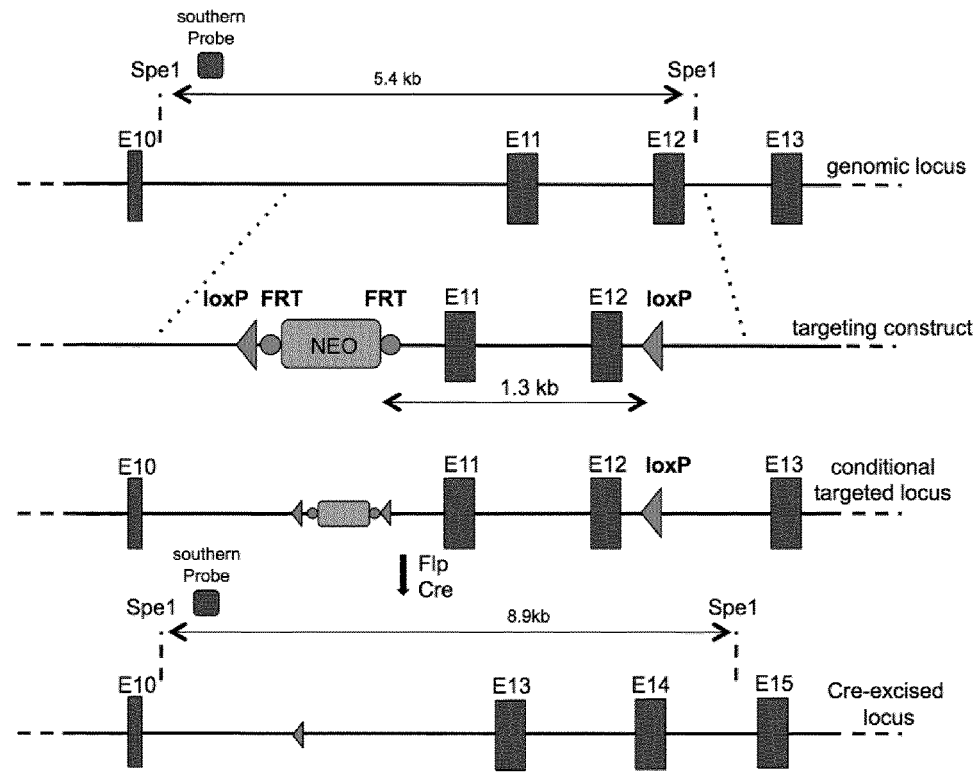
Figure 1B:
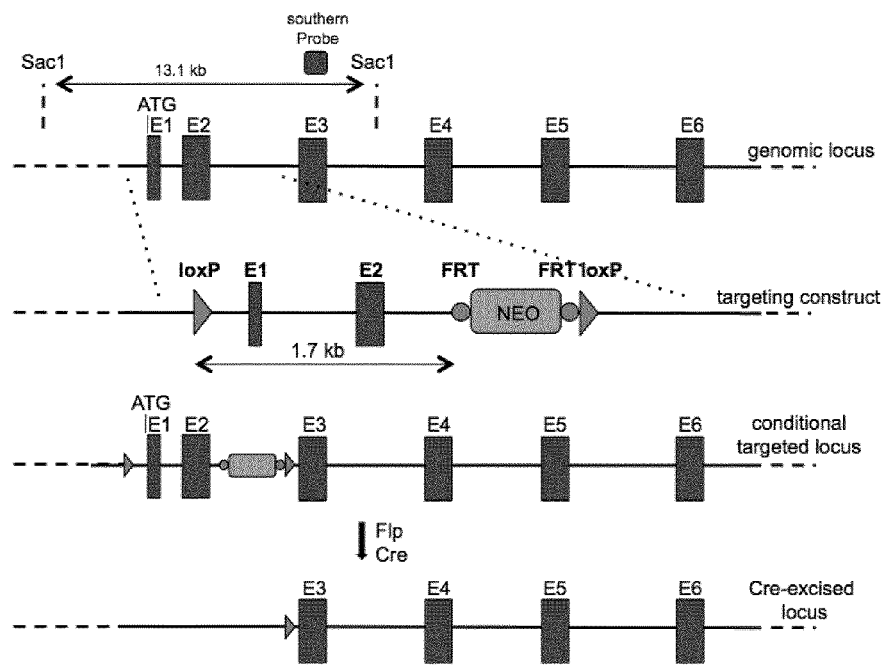
Figure 2A:
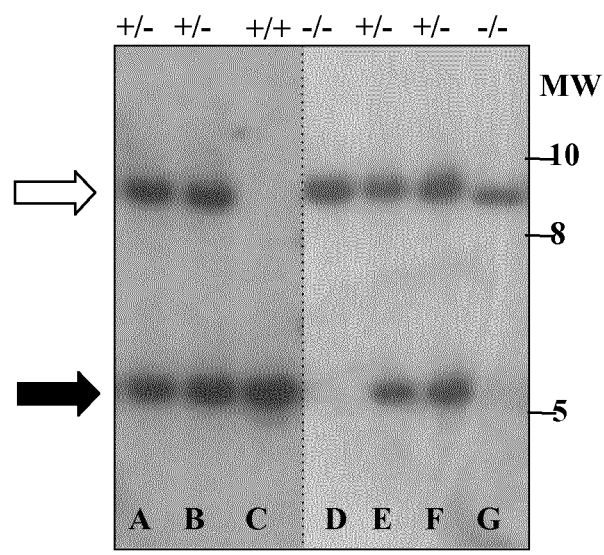
Figure 2B:
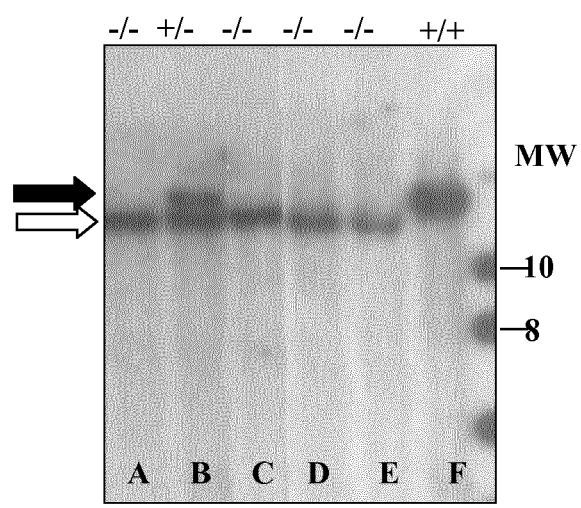
Figure 3:
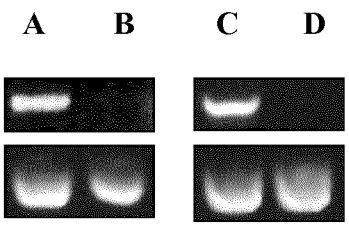
Figure 4A:
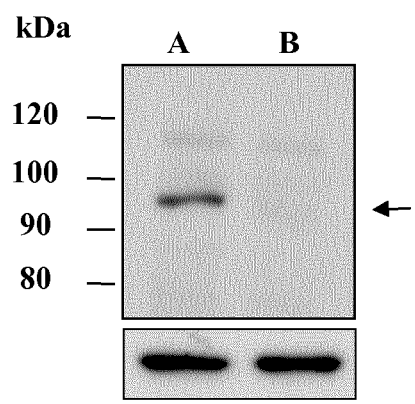
Figure 4B:
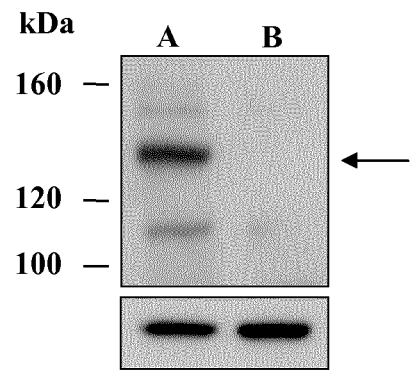
Figure 5:
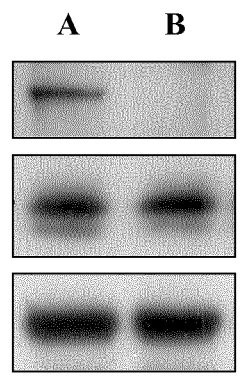

MCM8- and MCM9-Deficient Mice have Sterility Phenotypes with Totally or Nearly Absent Germ Cells Knock-out mice for MCM8 or MCM9 were performed as detailed in FIGS. 1A and B. For MCM8, the Inventors removed gene exons 11 and 12 that code for the N-terminal part of the MCM-family domain containing the ATP-binding Walker A site of the helicase as well as introduced an out-of frame mutation creating a premature STOP-codon in exon 13 (FIG. 1A). For MCM9, the two first exons of MCM9 were targeted, leaving intact the histone chaperone Asf1a[15] encoded in the opposite strand of the gene (FIG. 1B). The successful loss of both alleles in MCM8 (−/−) and MCM9 (−/−) mice was confirmed by southern blot (FIGS. 2A-MCM8 and 2B MCM9) and genomic PCR (data not shown), and the absence of detectable RNA by RT-PCR (FIG. 3). The Inventors generated specific antibodies that confirmed the lack of MCM8 or MCM9 proteins in the relevant knock-out mice (FIGS. 4A and 4B). The Inventors also checked that expression levels of Asf1a were similar in WT and MCM9-deficient cells (FIG. 5).

Both MCM8-deficient males and females as well as MCM9-deficient female mice repeatedly failed to yield any pregnancies when crossed with either WT or heterozygous+/− mice. Therefore, the Inventors inter-crossed heterozygous+/− mice to obtain MCM8 or MCM9 WT and KO mice from same litter.

Figure 6:
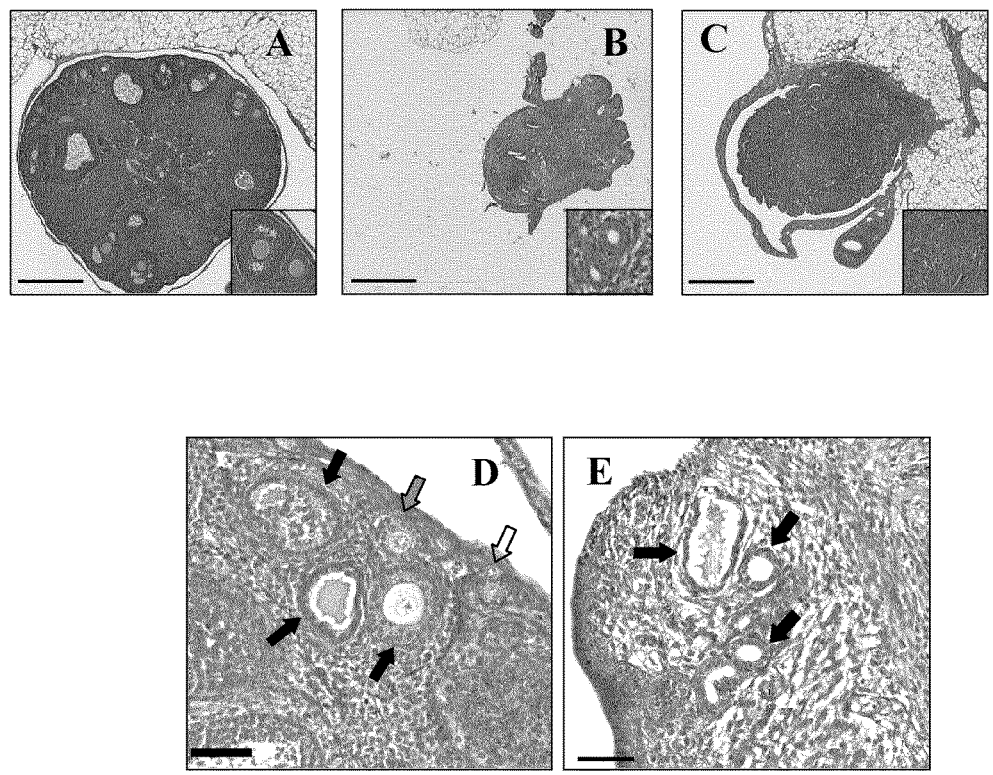
FIG. 6A represents Hematoxylin Eosin (HE)-stained histological sections of ovaries from WT adult females. bar: 500 μm.
FIG. 6B represents Hematoxylin Eosin (HE)-stained histological sections of ovaries from MCM8-deficient adult females. bar: 500 μm.
FIG. 6C represents Hematoxylin Eosin (HE)-stained histological sections of ovaries from MCM9-deficient adult females. bar: 500 μm.
FIG. 6D represents a detail of the histological analysis of adult WT ovaries shown in FIG. 6A. bar: 50 μm. Black arrows depict growing follicles, grey arrows depict primary- and white arrows depict primordial follicles.
FIG. 6E represents a detail of the histological analysis of adult MCM8-deficient ovaries shown in FIG. 6B. bar: 50 μm. Black arrows depict growing follicles.

Young adult (8-10 weeks) WT females exhibit abundant follicles at different stages of maturation. In contrast, MCM8-deficient adult ovaries were disorganized, strongly reduced in size and devoid of normal follicles. The Inventors observed few malformed primary follicles, but no follicles at later developmental stages (FIGS. 6A-C). Adult ovaries of MCM9-deficient females were completely devoid of follicles at any stage (FIG. 6C).

To further investigate when oogenesis was blocked, ovaries of newborn MCM8-deficient females were analyzed, and already contained smaller oocytes and cells with condensed nuclei, indicating apoptosis (FIGS. 7A-B). At day 15 pp, MCM8-deficient ovaries were strongly disorganized and contained only growth arrested primary follicles (FIGS. 7C-D).

Testes of young MCM8/9-deficient males were reduced in size already at day 15 pp, around the onset of meiotic engagement, compared to gonads of their WT littermates (FIGS. 8A-B). Adult (8-11 weeks) MCM8-deficient testes were reduced to less than half the size and weight of testes from control littermates (FIGS. 8C-D). Similarly, MCM9-deficient testes were strongly reduced in size compared to their WT-littermates (FIGS. 8C-D). Histological analysis revealed MCM8- and MCM9-deficient testes with abnormal seminiferous tubules, having smaller diameters as in WT testes. Whereas MCM8-deficient testes exposed only aberrant tubules, MCM9-deficient testes contained some tubules that were apparently still functional (FIGS. 9A-C). MCM9-deficient males were fertile, but had only 10% of the amount of functional spermatozoa found in WT litermates at an age of 6 to 8 weeks (data not shown).

Tubules of MCM8-deficient testes were completely devoid of postmeiotic cells such as round or elongated spermatids and spermatozoa (FIG. 1D, left panels). The most advanced tubule sections showed cells that are in zygonema as judged by morphological criteria (nuclear size and chromatin condensation). 68% of the tubules showed only a single layer of spermatogonia or the complete absence of germ cells (FIGS. 10A-C). A high number of cells exposing intensively eosin-stained, round nuclei was also observed, suggesting apoptosis. The Inventors carried out a TUNEL-assay that confirmed abundant apoptosis in MCM8-deficient testes (FIGS. 10D-E).

These results taken together, the sterility of MCM8- and MCM9-deficient female mice is explained by the absence of normally developing follicles (for MCM8) or the complete absence of follicles (MCM9) in the ovaries. In males, both knock-outs show defective growth of testes already at day 15 pp with exclusively (MCM8) or very abundant (MCM9) abnormal seminiferous tubules. MCM8-deficient testes have a complete deprivation of postmeiotic cells and significant apoptosis, explaining the sterility of MCM8-deficient males. This phenotype is somewhat alleviated in MCM9-deficient males that possess some seminiferous tubules that are early MCM8- and MCM9-Deficient Spermatocytes are Defective in Homologous Recombination-Mediated Double Strand Break Repair Next, the Inventors characterized which step in meiosis was affected by MCM8- or MCM9-deficiency. SYCP3, SYCP1 and γ-H2AX allow a classification of each meiotic nucleus to one of the main stages of meiotic prophase I. SYCP3 is an axial element of the synaptonemal complex (SC) at synapsis, when the pairing of homologous chromosomes occurs[16,17]. SYCP1 is also a protein of the SC but marks exclusively already synapsed axes of chromosomes[18,19]). γ-H2AX marks damaged DNA, when Spo11 induces double strand breaks (DSB), a prerequisite for homologous recombination to occur.[19] Later, DSBs are repaired by homologous recombination leading to crossingover events. At this stage, γ-H2AX remains exclusively localized on the so-called sex-body, the structure formed by the only partially homologous and thus not completely paired X- and Y-chromosomes.

At the earliest meiosis stage, in leptonema, SYCP3 becomes equally detected along individual chromosome axes in control- and MCM8-deficient nuclei. γ-H2AX is also recruited in both cases, showing that Spo11-mediated DSB formation occurs also in MCM8−/− cells (FIGS. 11A-H). However, γ-H2AX-staining was stronger in MCM8-deficient spermatocytes, suggesting an early defect in DNA repair. In the following zygonema stage (FIGS. 12A-H), homologous chromosomes begin to pair. In WT cells, SYCP3 signals of individual chromosomes joined and SYCP1 is recruited to synapsed areas. In contrast, MCM8-deficient nuclei have fragmented, small spots of SYCP1 staining (FIGS. 13A-J). At the pachynema stage, when crossing-overs are established and homologous chromosomes are fully synapsed, continuously stained by SYCP1 is observed in WT cells, as expected, but is never observed in MCM8-deficient nuclei (FIGS. 13A-J). The Inventors conclude that the successful pairing of the chromosomes was deficient in MCM8-deficient mice.

This result led us to further investigate whether homologous recombination (HR), the molecular step that give rise to crossing-overs, was defective. DMC1 is the meiotic homologue of Rad 51 and Rec A, involved in homologous recombination in eukaryotes and E. Coli respectively, and enables the DNA pairing strand exchange reaction. Mlh1 is another central protein in homologous recombination that localizes to late recombination nodules, when crossing-overs have been already established. The Inventors reproducibly detected a strong over recruitment of DMC1 to chromatin in MCM8-deficient mice (FIGS. 14A-J and FIGS. 15A-B). When the signal intensity in KO nuclei was electronically lowered in respect to the signals observed in WT nuclei, three times more DMC1 foci were observed in MCM8-deficient nuclei relative to WT nuclei at similar stages (FIGS. 14E-F). In contrast, Mlh1 was completely absent on chromosomes that remained always unpaired in testes from MCM8 KO mice, whereas one to two foci per chromosome pair were observed at pachynema in WT nuclei (data not shown). As both DMC1 and H2AX signals were over-recruited, these results suggested that the meiosis block in MCM8 deficient mice was at homologous recombination at the chromosome pairing stage, after tithe chromosome breaks, between the recruitment of DMC1 and the actual repair of DSBs.

In MCM9-deficient testes, few meiotic cells present were delayed in the progression of meiotic prophase I. Spermatocytes in the early leptonema and zygonema stages were five times overrepresented relative to WT testes. In addition, no spermatocytes in the late diplotene stage were present (FIGS. 16A-B). The average number of DMC1 in the early leptonema stage was half-reduced (FIGS. 16A-B) and their disappearance was delayed, resulting in four times more DMC1-foci at the pachytene stage, still localized on the paired autosomes (FIGS. 17A-J and data no shown). 48% of the few spermatocytes left proceed to the final diplonema stage with remaining DNA damage, as visualized by persistent γ-H2AX and RPA foci on chromosome axes (FIGS. 17A-J). The Inventors concluded that MCM9-, as MCM8-deficent mice, are defective in meiotic DSB repair by homologous recombination. This defect led to total (MCM8) or 90% depletion (MCM9) of spermatocytes.

MCM8 and MCM9 Form a Complex and Co-Regulate Each Other

Since MCM8- and MCM9-deficient mice showed similar severe defects in fertility and the repair of DSBs by homologous recombination, the Inventors next investigated whether both proteins could interacted with each other in-vivo. FIG. 18A shows that immunoprecipitation of MCM8 from testes extracts co-precipitated MCM9 and immunoprecipitation of MCM9 co-precipitated MCM8. MCM8 was found more engaged in a complex with MCM9, whereas a large part of MCM9 was in excess of MCM8. A similar result was obtained with human cells (FIG. 19A-D). Neither MCM8 nor MCM9 co-precipitated members of the MCM2-7 complex, as previously observed in Xenopus egg extracts,[4,5].

The Inventors next asked whether the cellular levels of MCM8 and MCM9 were also interdependent. As shown in FIG. 18B, the Inventors found that in KO MEF cells, when MCM8 or MCM9 is absent, MCM9 or MCM8 levels were strongly reduced. Importantly, the amounts of the other MCM2-7 proteins were not affected in knock-out MEF cells (FIG. 18B). By quantitative RT-PCR the Inventors found that the amount of mRNA of either MCM8/9 did not change in the absence of the partner (data not shown), indicating that it is the protein stability of MCM8 and MCM9 that is strongly reduced in the absence of the binding partner. The Inventors also found that MCM8 and MCM9 can form a complex in HeLa cells (FIG. 19A) and that MCM8 and MCM9 stabilize each other both by an Si RNA approach or an over-expression approach (FIG. 20). These data parallel the findings concerning the interdependent protein stability of the MCM2-7 proteins[20] and are in accordance with the existence of two independent MCM complexes, the MCM2-7 and a MCM8/9 complex.

MCM8/9-Deficient Cells Exhibit Growth Defects and Suffer from Genetic Instability Homologous recombination is also an important error-free mechanism used to repair DNA damage during the cell cycle. The Inventors therefore investigated whether mitotically cycling cells were affected by MCM8 or MCM9 deficiency. The Inventors first compared the growth of several independent couples of control- and MCM8- or MCM9-deficient MEF cells (a couple consisting always of cells originating from embryos from the same gestation). The Inventors always found that MCM8- and MCM9-deficient cells had a much slower groth rate than WT cells (FIGS. 21A-B). The profiles of G1- and S-phase were quite similar in WT and knock-out cells, although a reproducible accumulation of cells in G2/M (FIGS. 22A-D) was detected in KO cells. However, MCM8- as well as MCM9-deficient cells accumulated micronuclei (FIGS. 23A-C and FIG. 24), a phenotypic manifestation of unrepaired DNA breaks and a hallmark of genetic instability[21, 22]. Metaphase spreads of chromosomes revealed three (MCM8) and four (MCM9) times more broken or aberrant chromosomes than in WT cells (FIGS. 25A-C and FIG. 26).

The Inventors also observed that both MCM8- and MCM9-deficient MEF cells escaped senescence with a higher frequency as control cells (FIG. 27 and FIG. 28A-F) and resumed growth after crisis in an immortalized manner, another sign of genetic instability[23]. Furthermore, they often lost soon contact inhibition and formed colonies on culture plates (FIG. 28G-H).

These data show that MCM8 and MCM9 are not only essential during meiosis for the homologous recombination-mediated repair of DSBs, fertility and the integrity of reproductive organs, but also contribute in genome stability in mitotically cycling cells.

MCM8- and MCM9 Deficient Cells are Hypersensitive to Replication Fork Stress

Both knock-out mice were viable and MEF cells in culture proliferated, although slower and with genetic instability, suggesting that the core replication machinery was still functional in vivo. In *Xenopus* egg extracts, MCM8 and 9 were found essential for efficient DNA replication[4, 5]. However, in in-vitro systems derived from *Xenopus* eggs, DNA replication efficiency is at its maximum, as all potential DNA replication origins are activated, leading to an unusual short inter-origin space and an accelerated S phase (less than 20 min). A deficiency in DNA replication could be therefore rapidly detected. In somatic cells, S phase stands for 6-10 hrs, including during mouse early development (Wowlett and Bolton, 1985), J. Embryol. Exp. Morph, 87, 175; Ferreira and Carmon Forseca, 1997, J. Cell Sci, 11, 889). Therefore, defects in DNA replication can be compensated by induction of the store of dormant origins and/or a higher rate of replication. To investigate this possibility, and reveal possible DNA replication weaknesses in KO MEFs the Inventors first performed DNA fiber stretching[24], using a double pulse-labeling method, applying first a CldU pulse ("red" pulse), followed a second IdU pulse ("green" pulse), as in FIG. 29. Replication fork arrests can be detected by measuring the length of the second pulse, which becomes shorter if the fork is blocked or slowing down. FIG. 29 show that a higher proportion of collapsed forks is already present in MCM9 KO cells. To reveal whether MCM9 KO cells were more sensitive to replication stress, the Inventors treated MEF cells for 24 hrs with low concentration (1 μM) of aphidicolin (APH), an inhibitor of DNA polymerases that slows down or blocks replication forks.

First, the Inventors quantified the global efficiency of DNA replication by measuring the proportion of cells incorporating BrdU. Before exposure to APH, MCM9-deficient cells had a percentage of BrdU-positive nuclei smaller, but close to control cells (14% in KO cells, 20% in WT cells, FIG. 30, w/o), in agreement with the growth curve of the corresponding cells (FIG. 21B). After the APH treatment, the BrdU signal was strongly reduced in WT nuclei, but most cells were still labeled (FIGS. 31A-T), suggesting that most replication forks were functional but slowed down. In contrast, MCM9-deficient cells showed nearly no BrdU-labeled nuclei (FIG. 30, Oh, and FIG. 31H). The Inventors concluded that KO cells were highly sensitive to replication fork inhibition.

When cells were further released from APH treatment, control cells re-establish the original BrdU-intensity within the first 3 hours (FIG. 30, FIGS. 31A-T). In contrast, MCM9-deficient cells failed to restore normal labeling intensities, even after 24 hours (FIG. 30, FIGS. 31A-T), and it took 48 hours before the surviving population of KO cells had a percentage of BrdU-positive cells comparable to the situation before the APH treatment (FIG. 30). These results indicate that KO cells are unable to stabilize slowed-down or blocked replication forks and, in addition, are unable to activate new forks in order to compensate the fork loss during the APH treatment.). In addition, whereas WT cells resumed growth soon after the release from APH, MCM9- (as well as MCM8-), KO cells did not, died or stopped dividing (FIGS. 32A-B). The Inventors conclude that MCM9 KO cells are highly sensitive to replication stress, and unable to rescue arrested forks, resulting in growth arrest.

These results suggested that KO cells might not activate sufficient dormant origins to compensate for the fork collapse during APH treatment. To investigate this point, the Inventors used fiber stretching to measure the mean origin distances in WT- and KO. In the absence of APH, the mean origin distance in KO cells was slightly smaller than in WT cells (WT: 82.19 kb, KO: 68.31 kb). In the presence of APH, both cells activated more dormant origins in order to compensate slowed down or blocked forks, but KO cells are less efficient (FIG. 33). As a consequence, mitotic defects occur in KO cells after APH release, with completely fragmentized and broken chromosomes detected on metaphase chromosomes, explaining the growth arrest phenotypes observed.

MCM8 and MCM9 Control Homologous Recombination

When WT MEFs were treated by APH, a stronger expression of MCM9 and MCM8 was detected at the protein level, in agreement with an important role of the MCM8/9 complex in fork rescue and DNA damage response (FIGS. 34A-B). Rad51 is an essential protein of the homologous recombination pathway that is the main repair mechanisms of DSBs caused by replication fork arrest[25,12]. The Inventors found that MCM9-deficient cells have a severe defect in recruiting Rad51 to chromatin upon APH treatment (FIG. 34A), and a similar result was observed for MCM8 (FIG. 35).

These data together with the Inventors data previous results let us assume that DNA damage would be much higher in KO cells upon fork block. However, the Inventors unexpectedly observed that γ-H2AX was less recruited to chromatin in MCM9- and MCM8-deficient cells (FIGS. 34A-B and FIG. 35). As recruitment of γ-H2AX during replication stress depends on the activation of the S-phase checkpoint, the Inventors reasoned that the DNA damage might not be properly signaled in MCM8/9-deficient cells. Accumulation of ssDNA coated with RPA normally activates this checkpoint through phosphorylation of the Chk1 protein[26]. RPA-coated ssDNA and subsequent checkpoint activation is generated by the resection activity of MRE11, a crucial protein of HR recruited to collapsed replication forks early in the HR reaction ([27, 28, 29, 30] and for reviews [31, 32]). FIGS. 34A-B show that the recruitment of MRE11 to chromatin was as strongly reduced than Rad1 in KO cells, suggesting that resection of DSBs was less efficient. In agreement, less RPA accumulates on chromatin upon APH treatment (FIG. 34A). In further agreement, phosphorylation of Chk1 (and Chk2) was severely reduced in MCM9-deficient cells (FIG. 34B). These findings suggest that MCM9-deficient cells do not activate the S-phase checkpoint correctly due to failures to recruit proteins responsible for early steps in homologous recombination. This defect in checkpoint activation might also explain the observed defects in the activation of dormant origins.

Discussion

During gametogenesis, double strand breaks are introduced in the genome in order to recombine the genetic material. In mitotic division, when replication forks are blocked, they eventually collapse and produce DSB that should be repaired in order to restore genomic integrity and to finish replication. In both situations, homologous recombination is the mechanism used to repair the DSBs. Here, the Inventors report that MCM8- and MCM9-deficient mice are viable, but exhibit deteriorated and apoptotic gonads and are sterile due to recombination defects (with the exception of MCM9-deficient males which have 1% spermatozoids left). Moreover, MCM8/9 deficient cells are genetically unstable and hypersensitive to replication fork block.

In meiosis, these phenotypes are due to blocked DSB repair, failure of homologous chromosomes to synapse, with deficient recruitment of SYCP1 and Mlh1. spermatocytes. In agreement with the DNA repair failures, the Inventors also observed a strong accumulation of DMC1, the meiosis-specific Rad51 homolog, on MCM8-deficient meiotic chromosomes. DMC1 is normally recruited early to chromatin in distinct foci that disappear again during ongoing repair[33].

The Inventors further demonstrate that MCM8 and MCM9 form a yet unidentified complex in vivo and that this complex does not interact with the MCM2-7 complex. Furthermore, the absence of one binding-partner destabilizes the other, explaining the large similarities of the phenotypes in both knock-outs, and establishing a fundamental role of MCM8/MCM9 in meiotic DSB repair and fertility in vivo.

DNA damages features in fibroblasts accompany the deficiency in meiotic function of MCM8 or MCM9-deficient mice. Embryonic fibroblasts deficient for MCM8 or MCM9 die when exposed to fork-blocking agents. Upon fork block, MCM9-deficient cells do not recover functional replication forks.

Whereas in meiotic DSB repair, HR is exclusively employed for repair, mitotically cycling cells can use two fundamentally different DSB repair pathways, HR and non-homologous end joining (NHEJ)[34, 35]. Only HR can assure an error-free DSB repair. The Inventors did not detect any defects in NHEJ by analyzing V(D)J immunoglobin class switch recombination in MCM9-deficient mice[36], and (unpublished data, collaboration with J. P. de Villartay).

A main source of DNA damage is replication fork block during S-phase. 60 000 to 100 000 replication forks are activated during each cell cycle and potential blocks to their progressions are pausing sites that are prone to fork stalling due to their sequence, chromatin state or the presence of other chromatin-bound proteins. Normally, blocked forks activate the S-phase checkpoint that subsequently stabilizes these forks to avoid their collapse, and activates new forks through the firing of dormant origins (for review[37]). After extended times of fork block, like those induced by APH, forks eventually collapse, creating DSBs which are repaired by HR. MCM8/9-deficient cells are unable to survive the slowing down or block of replication forks. At low APH concentrations that slow down forks, KO cells nearly completely ceased to incorporate BrdU, and Rad51-recruitment to chromatin is inhibited. Rad51 is a crucial component recruited to both stabilize stalled forks and to repair fork-associated DNA damage through HR[12].

The activation of dormant origins is also reduced in KO cells during APH treatment. As Rad51, Mre11 is not properly recruited to chromatin upon fork block in the absence of MCM9. Mre11 executes the primary resection step at DSBs, producing ssDNA that is subsequently coated by RPA and later by Rad51 to enable strand invasion on the homologous sister chromatid. In agreement with the deficient recruitment of Mre11, the Inventors observe a strong reduction of RPA on chromatin in MCM9-deficient cells. As ssDNA/RPA complexes are the principal substrates that activate the S-phase checkpoint ([38, 39]), the Inventors accordingly observed that MCM9-deficient cells show a strong reduction of phosphorylated Chk1 upon fork block. Thus, MCM8/9 deficient cells suffer from an early block in homologous-recombination mediated DSB repair, and consequently they cannot repair the breaks and restart forks but also cannot process the breaks into checkpoint-activating intermediates.

MCM8 and MCM9 have been initially involved in DNA replication, but not found to form a complex for this function. Their role in meiotic recombination and DNA repair emphasizes the importance of the MCM8-MCM9 complex in linking DNA replication processes to homologous recombination processes.

Materials and Methods

Generation of MCM8 and MCM9−/− Mice and MEFs

MCM8: A targeting vector MEM1-HR was created for the insertion of two loxP sites flanking MCM8 exons 11 and 13, containing a long homology region of 6.4 kb and a short homology region of 1.7 kb and containing further the positive selection neomycin gene flanked by FRT sites and the DTA negative selection marker for the segregation of non-homologous recombined ES cell clones. Coding exons, junctions between the homology arms and selection cassettes, the cassettes itself and the junctions between the homology arms and the plasmid backbone were verified by sequencing. The targeting vector was transfected into ES cell line SV129/Pas and positive clones were selected, screened for correct recombination events by PCR and Southern blot and injected into C57BL/6J blastocysts. Blastocysts were re-implanted into OF1 pseudo-pregnant females and allowed to term.

High chimeric males were selected and mated with C57BL/6J Cre-deleter females to investigate whether the recombined ES cells have contributed to the germ layer and to excise the loxP-flanked region. MCM8 heterozygous knock-outs were identified by PCR and further confirmed by southern blot analysis. Heterozygous MCM8+/− animals were interbred to give homozygous MCM8−/− animals that were verified by PCR and Southern blot analysis (see also Supplementary FIG. 51).

MCM9: A targeting vector MEM2-HR was created for the insertion of two loxP sites flanking MCM9 exons 1 and 2, containing a long homology region of 5.4 kb and a short homology region of 1.6 kb, containing further the positive selection neomycin gene flanked by FRT sites and the DTA negative selection marker for the segregation of non-homologous recombined ES cell clones. ES cell lines, transfection-, screening- and breeding procedures were similar as for MCM8. Creation and verification of both knock-out models was conducted by GenOway, Lyon, France (www.genoway.com). Both heterozygous+/− animals were back-crossed for several generations to C57BL/6 mice. All experiments were conducted according to the CNRS guidelines and were approved by the regional ethics committee on live animals experimentation.

Primary MEFs were obtained by standard procedure from 13.5 days pc heterozygous females that were mated with heterozygous males. MEFs were cultivated in DMEM supplemented with 10% FBS and antibiotic-antimycotic (Gibco) and used at early passages.

Histology and Immunohistochemistry

Testes and ovaries were obtained from KO and WT animals (always originating from same litter) at indicated age. Organs dedicated for Haematoxylin-eosin (HE) stain were fixed in Bouin's fluid for 6 hours (small pieces) or over night at RT, organs dedicated for immunohistochemistry were fixed in 4% paraformaldehyde at RT and in both cases embedded in paraffin. HE stained sections were scanned using automated tissue slide scanning on a Hamamatsu NanoZoomer Digital Pathology system. Slides for immunohistochemistry were de-paraffinized and rehydrated according to standard procedures. TUNEL assay was performed with the Deadend Fluorometric TUNEL system (Promega) according to provider's manual.

Spermatocyte Nuclei Spreads

Spermatocyte nuclei spreads were prepared as described in Peters et al. (1997).

Immunofluorescence Assays

Immunofluorescence assays on meiotic spreads were prepared using blocking buffer (5% milk, 5% donkey serum in PBS) as described in Moens et al., 1997). Primary antibodies were incubated over night at RT in the following dilutions: α-SYCP3 1:500 (gift from P. de Boer), α-SYCP1 1:50 (gift from C. Heyting), α-DMC1 1:200 (Santa Cruz Biotechnology), α-phospho-H2AX 1:20'000 (Upstate Biotechnologies), α-Mlh1 1:50 (551091, BD Pharmigen). Secondary antibodies (goat anti-guinea pig Alexa Fluor 488 (Molecular Probes), donkey Cy3-conjugated anti-rabbit and donkey Cy5-conjugated anti-mouse antibodies (Jackson Immunoresearch Laboratories)) were incubated for 1 h at 37° C. Nuclei were visualized by staining with DAPI.

MEF cells were fixed for immunofluorescence in 4% paraformaldehyde/PBS for 10 min at 4° C. and subsequently extracted with 0.5% Triton X-100/PBS for 15 min at RT. After washing, cells were saturated with 5% BSA/PBS for 30 min. BrdU-immunodetection was performed as described in Ekkholm-Reed et al. (2004). Anti-BrdU antibody was purchased from BD Biosciences and Texas-red conjugated anti-mouse from Jackson Immuno Research Laboratories. DNA was stained with Hoechst. Slides were mounted with Moviol (Aldrich).

Digital images were captured using a cooled charge-coupled device (CDD) camera (Coolsnap HQ; Photometrics) attached to a Leica DM 6000B microscope and were analyzed using the Metamorph imaging software. After data acquisition, images were processed with either Metamorph for quantitative analysis ("Integrated Morphometry Analysis") or with Photoshop CS5.

Cell Culture and Microscopy

MEF cells were grown in DMEM supplemented with 10% FBS and antibiotic-antimycotic (Gibco) and used at early passages. Whenever WT and KO cells were compared, MEF WT/KO pairs always originated from same gestations (obtained by crossing heterozygous males and females). Furthermore, MEF WT/KO pairs originating from different gestating females were used in all repetitions of experiments. At least four independent WT/KO couples were used to analyze growth of MEF cells and at least two were used for the generation of growth curves. At least two different couples were used to evaluate micronuclei and chromosome aberrations in metaphase spreads. Cells were labeled with BrdU for 10 min at a concentration of 10 µM BrdU in DMEM. Metaphase spreads were prepared according to Eot-Houllier et al. (2008).

DNA Fibre Experiments.

For dual labelling of replication tracts, exponential cell cultures of wild-type or KO MEFs cells were pulse-labelled with 25 µM CldU for 20 min followed by 250 µM IdU for 20 min. For single labelling, exponential cell cultures were pulse-labelled with 25 µM BrdU for 20 min. Labelled cells were harvested and DNA fibre spreads prepared as previously described (Jackson and Pombo, 1998). For immuno-detection of CldU or BrdU-labeled tracts, acid-treated fibre spreads were incubated with rat anti-BrdU monoclonal antibody (Oxford Biotechnology) at a 1:1,000 dilution for 1 h at room temperature. Slides were then fixed with 4% paraformaldehyde and incubated with Cy3-conjugated donkey anti-rat immunoglobulin G (IgG) (Jackson Immuno Research Laboratories) at 4 µg/ml for 90 min at room temperature. IdU was detected using mouse anti-BrdU monoclonal antibody (1:1000; Becton Dickinson) overnight at 4° C. and AlexaFluor 488-conjugated goat anti-mouse IgG (1:500; Invitrogen) for 90 min. Fibers were examined using a Zeiss Apotome microscope coupled with a 63× immersion-oil objective. Measurements were recorded from fibres in well-spread (untangled) areas of the slides to prevent the possibility of recording labelled patches from bundles of fibres. The length of the labelled tracks was measured using AxioVision software and the distance in micrometers multiplied by 2.59 Kb. DNA fibres with collapsed forks were analysed as in Petermann et al. (2010). The distance between replication origins was performed as in Maya-Mendoza et al. (2007). Briefly, MEFs cells were transfected using FuGene (Roche) and biotin-dUTP (Roche) and incubated for 30 min. Cells were harvested and the DNA fibres stretched. Fibres were examined using a Zeiss Apotome microscope using, a ×40 lens, labelled tracks measured using the Axiovision software and converted to kilobase pairs using a conversion factor of 1 µm=2.59 kb (Jackson and Pombo, 1998). Measurements were recorded in randomly selected fields (selected at low power) from dispersed, untangled areas of the DNA spread. As the analysis of single, unbroken fibres is essential, routine quality control for spreading of different cell types under different experimental conditions was performed using direct DNA labelling with YOYO (Merrick et al. (2004) or BrdU immunolabelling of fibres from cells labelled with 10 µM BrdU for □24 h (Maya-Mendoza et al. (2007) Alternatively for on distance experiments, an anti-DNA antibody was used (Millipore) to distinguish single DNA fibres.

Chromatin Isolation, Immunoprecipitation and Antibodies

For chromatin isolation, MEF cells were harvested, washed with PBS, frozen at −80° C. or directly lysed in CSK buffer (150 mM NaCl, 10 mM HEPES pH 7.5, 300 mM Sucrose, 1 mM MgCl$_2$, 1 mM EDTA, 1 mM ATP.MgCl$_2$, 1 mM DTT, 0.2% Triton X-100, Phosphatase-inhibitors (Calbiochem), protease-inhibitors Leupeptin, Aprotinin and Pepstatin at a concentration of 10 µg/ml) for 10 min on ice in a volume of 1 µl buffer for 2000 cells. For whole cell extract ("WCE"), a sample of the lysate was mixed with two times Laemli SDS buffer and boiled. The lysate was centrifuged at 3'800 g for 5 min at 4° C., the pellet homogenized again in CSK buffer, extracted again for 5 min on ice and centrifuged again and finally solubilized in two times Laemli SDS buffer (1 µl buffer for 5000 cells).

For immnuoprecipitations, cells or testis-tissue were homogenized (using a douncer for tissue) in IP buffer (150 mM NaCl, 50 mM Tris pH 7.5, 5 mM EDTA, 0.3% NP40, 10% glycerol, Phosphatase-inhibitors (Calbiochem), protease-inhibitors Leupeptin, Aprotinin and Pepstatin at a concentration of 10 µg/ml) for 30 min on ice. A sample of the lysate was mixed with two times Laemli SDS buffer and boiled and served as "extract" sample. The lysate was centrifuged at 4° C. for 15 min at 16'000 g. The supernatant was split and incubated with the appropriate antibodies for 2 h at 4° C. on a turning wheel. 5 µl of ProtA-Agarose beads (Roche) were then added and incubated for another hour.

Beads were recovered and washed 6 times with IP buffer and tubes were changed after the first and before the last wash. Beads were finally boiled in three times Laemi SDS buffer.

The antibody against mouse MCM9 was generated by immunization of rabbits with a recombinant expressed and purified C-terminal part (aa 908-1290) of mouse MCM9. The antibody against mouse MCM8 was generated by immunization of rabbits with a recombinant expressed and purified N-terminal part (aa 1-200). The Asf1-antibody was a gift from G. Almouzni. Other antibodies used were purchased from as followed: MCM2: sc-9839, MCM5: sc-22780, MCM7: ab9972, Rad51: sc-8349, Mre11: NB100-142 Novus Biologicals, RPA32: ab76420, γ-H2AX: clone JBW301, Upstate, Phospho-Chk1: Cell Signalling, actin: A4700, Sigma, Histone H3: ab1792, GAPDH: Ambion.

RT-PCR and QPCR

The GeneElute Mamalian total RNA Miniprep Kit (Sigma) was used to prepare mRNA from tissue and MEF cells. The Superscript III Reverse Transcriptase Kit (Invitrogen) was used to synthesize cDNA from this RNA. To test for residual transcripts of MCM9 in MCM9-deficient testes tissue or MEF cells, 5'-primer ATGAATAGTGAGCAGGTCACCCTG (SEQ ID NO: 5) and 3'-primer TCATGGCTTTTTCCTCATCTCTTC (SEQ ID NO: 6) were used.

Primers for the actin control reaction were

```
                                    (SEQ ID NO : 7)
5'-GCCGGCTTACACTGCGCTTCTT
and (SEQ ID NO : 8)
3'-TTCTGGCCCATGCCCACCAT.
```

Quantitative PCR was performed on a Lightcycler 480 using the Lightcycler 480 SYBR Green I Master kit from Roche. Quantification data were normalized to the expression of the endogenous β-Actin gene within the log-linear phase of the amplification curve obtained for each primer set using the ΔΔCt method. All samples were prepared in 2 to 3 biological repeats.

Used primers were:

```
                                    (SEQ ID NO : 9)
MCM9 5'-AGACCGTGGGATACTTCCAA, (SEQ ID NO : 10)
MCM9 3'-GATGTCGGGATTACCAGGAA, (SEQ ID NO : 11)
MCM8 5'-GCTTGGGGAAGAGTCAGA, (SEQ ID NO : 12)
MCM8 3'-GGTATTTCCACAAACATACACACC
and actin primers as above.
```

Endogenous MCM8 and MCM9 Co-Immunoprecipitate in HeLa Cell Nuclear Extracts

HeLa nuclear extracts were prepared from classical Dignam protocol (J. D. Dignam et al., *Methods Enzymol.* 101, 582 (1983)). To perform MCM9 immunoprecipitation, 1 mg of nuclear extract was incubated 3H at 4° C. with 10 µg of anti-MCM9 antibody (rabbit polyclonal antibody directed against a C-terminus peptide of MCM9), in IP buffer (150 mM KCl, 20 mM Tris ph7.5, 0.05% NP-40, 0.1% Tween-20, 10% glycerol, (5 mM MgCl$_2$, 1 mM ATP, 1 mM DTT, protease inhibitors). For the immunoprecipitation control, 25 µg of rabbit IgG were incubated 3 h with the same amount of HeLa nuclear extract. The extracts were then incubated 1H at 4° C. with 10 µA of Protein A-Agarose beads (ROCHE). MCM9 immunoprecipitation and MCM8 co-immunoprecipitation were revealed by western blot using anti-MCM9 and anti-MCM8 antibodies (rabbit polyclonal directed against a C-terminus peptide of MCM8), respectively. Rabbit True Blot secondary antibodies (eBIOSCIENCE) were used for the western blot analysis. The input represents 20 µg of the HeLa nuclear extract used for the immunoprecipitation. The amount of IgG on the Ponceau red shows the same amount of antibody used in each condition.

MCM9 Co-Immunoprecipitates with FLAG-MCM8 in U2OS Cells

U2OS cells were transfected in 100 mm culture dishes for 48 h using 35 µl of lipofectamine (invitrogen), with 6 µg of pcDNA3-MCM9 and 6 µg of pcDNA3-FLAG-MCM8 or pcDNA3 empty vector for the Mock condition. Cells were then lysed in a lysis buffer (50 mM Tris-HCl ph 7.5, 250 mM NaCl, 5 mM EDTA, 0.5% NP-40, 1 mM DTT, 1 mM ATP, protease and phosphatase inhibitors) and IP were performed on 500 µg of total lysate. FLAG immunoprecipitation was performed with 10 µl of mouse anti-FLAG-M2-agarose beads (A2220, SIGMA), for 4H at 4° C. FLAG-MCM8 immunoprecipitation and MCM9 co-immunoprecipitation were revealed by western blot using anti-FLAG (M2, SIGMA) and anti-MCM9, respectively. Rabbit True Blot secondary antibodies were used for the western blot. The input represents 20 µg of the total lysate used for the immunoprecipitation. The amount of IgG on the Ponceau red shows the same amount of antibody used in each condition.

Endogenous MCM8 Co-Immunoprecipitates with MCM9-FLAG-HA in S3 HeLa Nuclear Extract S3 HeLa cells were stably transfected with poZ-MCM9-FLAG-HA viral plasmid (MCM9-FH), or with poZ-FLAG-HA empty vector (FH). S3 HeLa cell nuclear extracts were prepared from Dignam protocol. FLAG immunoprecipitation was performed with 10 µl of mouse anti-FLAG-M2-agarose beads (SIGMA, A2220), for 4H at 4° C. in the IP buffer previously described. MCM9-FH immunoprecipitation and MCM8 co-immunoprecipitation were revealed by western blot using anti-HA (HA.11 16B12, COVANCE) and anti-MCM8 antibody, respectively. Rabbit True Blot secondary antibodies were used for the western blot. The input represents 20 µg of the total lysate used for the immunoprecipitation. The amount of IgG on the Ponceau red shows the same amount of antibody used in each condition.

Exogenous MCM8 and MCM9 Stabilize Each Other in Cells

U2OS cells were transfected as previously described with pcDNA3-FLAG-MCM8 or HA-MCM8 and/or pcDNA3-MCM9 or only with pcDNA3 empty vector for the Mock condition. Cells were lysed in a lysis buffer (50 mM Tris-HCl pH 7.5, 100 mM NaCl, 5 mM EDTA, 1% Triton X-100, phosphatase and protease inhibitors) and 20 µg per lane of total lysate was used for WB. WB was performed using anti-MCM9, anti-FLAG or anti-HA antibodies and anti-Tubulin (Mouse, SIGMA) for the loading control.

Endogenous MCM8 and MCM9 Stabilize Each Other in Cells

HeLa cells were transfected for 48 h, in 6 wells culture dishes using 4 µl oligofectamine (Invitrogen) and 0.5 µM siGENOME Non-Targeting siRNA for the Mock condition (D-001206-14), 0.5 µM of ON-TARGET plus SMARTpool for human MCM8 (L-017291-00:

GGCAAUACAUCAGGUGUUA; (SEQ ID NO: 13)

GAACAUGUGAUUGCAAUAA; (SEQ ID NO: 14)

UGAUGGAGUUCUCACUUAA, (SEQ ID NO: 15)

GAAAGUACAUUGGCUAUGC, (SEQ ID NO: 16))

or 0.5 µM of siGENOME SMARTpool for human MCM9 (M-017615-01:

GAAGAUGACUUAGUGGAUA; (SEQ ID NO: 17)

GAAAGCAAAUUACAUCCAA; (SEQ ID NO: 18)

GAAUAGCGAUCAAGUUACA; (SEQ ID NO: 19)

AGUCAUAUGUUUCGGAAUA, (SEQ ID NO: 20)

from DHARMACON. Cells were lysed in a lysis buffer containing 1% Triton-X100 as previously described and 20 µg per lane of total lysate was used for WB. WB was performed using anti-MCM9, anti-MCM8 and anti-Tubulin antibodies for the loading control.

BIBLIOGRAPHY

1 Donovan, S., et al. (1997) *Proc Natl Acad Sci USA* 94, 5611-5616.
2 Maiorano, et al. (2000) *J Biol Chem* 275, 8426-8431.
3 Liu, Y., et al. (2009). *BMC Evol Biol* 9, 60
4 Maiorano, D., et al. (2005) *Cell* 120, 315-328
5 Lutzmann, M. & Mechali, M. (2008) *Mol Cell* 31, 190-200,
6 Volkening, M. & Hoffmann, I. (2005) *Mol Cell Biol* 25, 1560-1568,
7 Gozuacik, D. et al. (2003) *Nucleic Acids Res* 31, 570-579 (2003).
8 Blanton, H. L. et al. *PLoS Genet.* 1, e40,
9 He, C. et al. (2009) *Nat Genet.* 41, 724-728,
10 Stolk, L. et al. (2009) *Nat Genet.* 41, 645-647,
11 Arnaudeau, C., Lundin, C. & Helleday, T. DNA. *J Mol Biol* 307, 1235-1245, (2001)
12 Petermann, E., et al. *Mol Cell* 37, 492-502, (2010).
13 Pittman, D. L. et al. *Mol Cell* 1, 697-705, (1998).
14 Handel, M. A. & Schimenti, J. C. *Nat Rev Genet.* 11, (2010).
15 Groth, A. et al. *Mol Cell* 17, 301-311, (2005).
16 Dobson, M. J., et al. *J Cell Sci* 107 (Pt 10), 2749-2760 (1994).
17 Schalk, J. A. et al. *Chromosoma* 107, 540-548 (1998).
18 de Vries, F. A. et al. *Genes Dev* 19, 1376-1389, (2005).
19 Keeney, S., Giroux, C. N. & Kleckner, N. *Cell* 88, 375-384, (1997).
20 Chuang, C. H., Wallace, M. D., Abratte, C., Southard, T. & Schimenti, J. C. *PLoS Genet.* 6, (2010).
21 Naim, V. & Rosselli, F. *Cell Cycle* 8, 2907-2911, (2009).
22 Chan, K. L., et al. *Nat Cell Biol* 11, 753-760, (2009).
23 Wang, J. et al. *EMBO Rep* 10, 1272-1278, (2009).
24 Maya-Mendoza, A., et al. *EMBO J* 26, 2719-2731, (2007).
25 Hashimoto, Y., et al. *Nat Struct Mol Biol* 17, 1305-1311, (2010).
26 Byun, T. S., et al. *Genes Dev* 19, 1040-1052, (2005).
37 Wang, Y. et al. *Genes Dev* 14, 927-939 (2000).
28 Grenon, M., et al. *Nat Cell Biol* 3, 844-847, (2001).
29 Lisby, M., et al. *Cell* 118, 699-713, (2004).
30 Jazayeri, A. et al. *Nat Cell Biol* 8, 37-45, (2006).
31 Harrison, J. C. & Haber, J. E. *Annu Rev Genet.* 40, 209-235, (2006).
32 Bernstein, K. A. & Rothstein, R. *Cell* 137, 807-810, (2009).
33 Moens, P. B. et al. *J Cell Sci* 115, 1611-1622 (2002).
34 Khanna, K. K. & Jackson, S. P. *Nat Genet.* 27, 247-254, (2001).
35 Shrivastav, M., De Haro, L. P. & Nickoloff, J. A. *Cell Res* 18, 134-147, (2008).
36 de Villartay, J. P., Fischer, A. & Durandy, A. *Nat Rev Immunol* 3, 962-972, (2003).
37 Blow, J. J., Ge, X. Q. & Jackson, D. A. *Trends Biochem Sci*, (2011).
38 Zou, L. & Elledge, S. J. *Science* 300, 1542-1548, (2003).
39 Choi, J. H. et al. *Proc Natl Acad Sci USA* 107, 13660-13665, (2010).

The invention claimed is:

1. A recombinant protein complex comprising MCM8 and MCM9 proteins, said complex being devoid of nucleic acid molecules, wherein:
   said MCM8 consists of the amino acid sequence consisting of SEQ ID NO: 1 or 3, and
   said MCM9 consists of the amino acid sequence consisting of SEQ ID NO: 2 or 4,
   said MCM8 and MCM9 proteins being produced in an in vitro production system selected from the group consisting of: bacteria, yeast, insect cells, Wheat germ lysate and *E. coli* free cell extract.

2. A pharmaceutical composition comprising as active substance a recombinant complex comprising MCM8 and MCM9 proteins, said complex being devoid of nucleic acid molecules, said MCM8 and MCM9 proteins being two distinct proteins, in association with a pharmaceutically acceptable carrier, wherein:
   said MCM8 consists of the amino acid sequence consisting of SEQ ID NO: 1 or 3, and
   said MCM9 consists of the amino acid sequence consisting of SEQ ID NO: 2 or 4,
   said MCM8 and MCM9 proteins being produced in an in vitro production system selected from the group consisting of: bacteria, yeast, insect cells, Wheat germ lysate and *E. coli* free cell extract.

3. The recombinant protein complex according to claim 1, consisting of MCM8 and MCM9 proteins.

4. A method for the in vitro recombination of DNA or for the in vitro DNA repair, comprising a step of contacting a DNA molecule to be recombined or repaired with a recombinant complex comprising MCM8 and MCM9 proteins, said complex being devoid of nucleic acid molecules, said MCM8 and MCM9 proteins being two distinct proteins, wherein:
   said MCM8 consists of the amino acid sequence consisting of SEQ ID NO: 1 or 3, and
   said MCM9 consists of the amino acid sequence consisting of SEQ ID NO: 2 or 4.

* * * * *

UNITED STATES PATENT AND TRADEMARK OFFICE
CERTIFICATE OF CORRECTION

PATENT NO. : 9,624,278 B2
APPLICATION NO. : 14/240959
DATED : April 18, 2017
INVENTOR(S) : Marcel Mechali et al.

It is certified that error appears in the above-identified patent and that said Letters Patent is hereby corrected as shown below:

In Column 21, Line 65:
"after tithe chromosome breaks".

Should be replaced with:
--after the chromosome breaks--.

Signed and Sealed this
Twelfth Day of September, 2017

Joseph Matal
*Performing the Functions and Duties of the
Under Secretary of Commerce for Intellectual Property and
Director of the United States Patent and Trademark Office*